US007053196B2

(12) United States Patent
D'Elia et al.

(10) Patent No.: US 7,053,196 B2
(45) Date of Patent: May 30, 2006

(54) ***KETOGULONIGENIUM* ENDOGENOUS PLASMIDS**

(75) Inventors: John D'Elia, Champaign, IL (US); Steven F Stoddard, Decatur, IL (US)

(73) Assignee: Archer-Daniels-Midland Company, Decature, IL (US)

(*) Notice: Subject to any disclaimer, the term of this patent is extended or adjusted under 35 U.S.C. 154(b) by 466 days.

(21) Appl. No.: 10/261,942

(22) Filed: Oct. 2, 2002

(65) Prior Publication Data

US 2003/0087440 A1 May 8, 2003

Related U.S. Application Data

(62) Division of application No. 09/826,191, filed on Apr. 5, 2001, now abandoned.

(60) Provisional application No. 60/194,627, filed on Apr. 5, 2000.

(51) Int. Cl.
*C07H 21/04* (2006.01)
*C12N 15/70* (2006.01)
*C12N 15/74* (2006.01)

(52) U.S. Cl. .................. 536/23.1; 435/320.1; 435/243; 435/252.3; 435/252.33; 435/252.8

(58) Field of Classification Search ............. 435/320.1, 435/243, 252.1, 252.3; 536/23.1, 24.1
See application file for complete search history.

(56) References Cited

U.S. PATENT DOCUMENTS

| | | | |
|---|---|---|---|
| 2,421,611 | A | 6/1947 | Gray |
| 3,043,749 | A | 7/1962 | Huang |
| 3,234,105 | A | 2/1966 | Motizuki et al. |
| 3,907,639 | A | 9/1975 | Makover et al. |
| 3,912,592 | A | 10/1975 | Makover et al. |
| 4,876,195 | A | 10/1989 | Shirafuji et al. |
| 4,877,735 | A | 10/1989 | Nogami et al. |
| 4,892,823 | A | 1/1990 | Imai et al. |
| 4,933,289 | A | 6/1990 | Imai et al. |
| 4,935,359 | A | 6/1990 | Yin et al. |
| 4,945,048 | A | 7/1990 | Uchihori et al. |
| 4,960,695 | A | 10/1990 | Hoshino et al. |
| 4,994,382 | A | 2/1991 | Ameyama et al. |
| 5,082,785 | A | 1/1992 | Manning et al. |
| 5,312,741 | A | 5/1994 | Hoshino et al. |
| 5,344,768 | A | 9/1994 | Urakami |
| 5,399,496 | A | 3/1995 | Fujiwara et al. |
| 5,437,989 | A | 8/1995 | Asakura et al. |
| 5,474,924 | A | 12/1995 | Nogami et al. |
| 5,541,108 | A | 7/1996 | Fujiwara et al. |
| 5,580,782 | A | 12/1996 | Beppu et al. |
| 5,834,231 | A | 11/1998 | Stoddard et al. |
| 5,989,891 | A | 11/1999 | Liaw et al. |
| 6,127,156 | A | 10/2000 | Hoshino et al. |
| 6,127,174 | A | 10/2000 | Tonouchi et al. |
| 6,316,231 | B1 | 11/2001 | Stoddard et al. |
| 6,319,699 | B1 | 11/2001 | Stoddard et al. |
| 6,503,748 | B1 | 1/2003 | Schmidt et al. |
| 6,506,583 | B1 | 1/2003 | Stoddard et al. |
| 6,511,820 | B1 | 1/2003 | Stoddard et al. |
| 6,541,239 | B1 | 4/2003 | Stoddard et al. |
| 6,562,584 | B1 | 5/2003 | Stoddard et al. |
| 2002/0039761 | A1 | 4/2002 | D'Elia |

FOREIGN PATENT DOCUMENTS

| | | | |
|---|---|---|---|
| CN | 1.081.470 | A | 2/1994 |
| EP | 0 206 471 | B1 | 12/1986 |
| EP | 0 213 591 | B1 | 3/1987 |
| EP | 0 221 707 | B1 | 5/1987 |
| EP | 0 276 832 | A2 | 8/1988 |
| EP | 0 278 447 | B1 | 8/1988 |
| EP | 0 276 832 | A3 | 7/1989 |
| EP | 0 381 027 | A3 | 5/1990 |
| EP | 0 381 027 | A1 | 8/1990 |
| EP | 0 448 969 | A2 | 10/1991 |
| EP | 0 448 969 | A3 | 1/1992 |
| EP | 0 518 136 | A2 | 12/1992 |
| EP | 0 518 136 | A3 | 3/1994 |
| EP | 0 832 974 | A2 | 4/1998 |
| EP | 0 832 974 | A3 | 4/1998 |
| EP | 1 076 094 | A2 | 2/2001 |
| JP | 41-159 | | 1/1966 |
| JP | 41-160 | | 1/1966 |
| JP | 41-5907 | | 3/1966 |
| JP | 59-113896 | | 6/1984 |
| JP | 3-294281 | | 12/1991 |
| JP | 7-67673 | | 3/1995 |
| JP | 7-250671 | | 10/1995 |
| JP | 8-245702 | | 9/1996 |
| SU | 526660 | | 10/1976 |
| WO | WO 98/17819 | A1 | 4/1998 |
| WO | WO 98/17819 | A3 | 4/1998 |

(Continued)

OTHER PUBLICATIONS

Everett et al. Pendred syndrome is caused by mutations in a putative sulphate transporter gene (PDS). Nature Genetics 17: 411-422, 1997.*

Scott et al. The pendred syndrome gene encodes a chloride-iodide trasnport protein. Nature Genetics 21: 440-443, 1999.*

Altschul, S.F., et al., "Gapped BLAST and PSI-BLAST: a new generation of protein database search programs," *Nucl. Acids Res.* 25:3389-3402, Oxford University Press (1997).

(Continued)

*Primary Examiner*—James Ketter
*Assistant Examiner*—David A. Lambertson
(74) *Attorney, Agent, or Firm*—Kilpatrick & Lockhart Nicholson Graham LLP

(57) ABSTRACT

The present invention relates, in general, to a genus of bacteria known as *Ketogulonigenium*. The present invention further relates to transformed *Ketogulonigenium*, and methods of transforming *Ketogulonigenium*. The present invention also relates to nucleic acid molecules, and vectors.

24 Claims, 34 Drawing Sheets

FOREIGN PATENT DOCUMENTS

| | | | |
|---|---|---|---|
| WO | WO 98/33885 | A1 | 8/1998 |
| WO | WO 98/33885 | A3 | 8/1998 |
| WO | WO 00/15827 | A1 | 3/2000 |
| WO | WO 00/15827 | A3 | 7/2000 |

OTHER PUBLICATIONS

Delic, V., et al., "Microbial Reactions for the Synthesis of Vitamin C (L-Ascorbic Acid)," in *Biotechnology of Vitamins, Pigments and Growth Factors*, Vandamme, E.J., ed., Elsevier Applied Science (London & New York) pp. 299-336 (1989).

Helinski, D.R., et al., "Replication Control and Other Stable Maintenance Mechanisms of Plasmids," in *Escherichia coli and Salmonella: Cellular and Molecular Biology*, Ch. 122, vol. 2, 2nd edition, Neidhardt, F.C., ed., pp. 2295-2324, ASM Press (1996).

Lonsdale, D.M., et al., "pFC1 to pFC7: A Novel Family of Combinatorial Cloning Vectors," *Plant Biol. Reporter* 13:343-345, Transaction Periodicals Consortium (1995).

Pearson, W.L., and Lipman, D.J., "Improved tools for biological sequence comparision," *Proc. Natl. Acad. Sci. USA* 85:2444-2448, National Academy of Sciences of the USA (1988).

Sugisawa, H., et al., "Microbial Production of 2-Keto-L-Gulonic Acid from L-Sorbose and D-Sorbitol by *Gluconobacter melanogenus," Agric. Biol. Chem.* 54:1201-1209, Japan Society for Bioscience, Biotechnology, and Agrochemistry (1990).

Follettie, M.T., "DNA Technology for *Corynebacterium glutamicum*: Isolation and Characterization of Amino Acid Biosynthetic Genes," Ph.D. Thesis, Massachusetts Institute of Technology (1989).

Kleslich, K., "Biotransformations," *Biotechnology, A Comprehensive Treatise in 8 Volumes*, Deerfield Beach, Florida 6A:436-437, Verlag Chemie, (1984).

Martin, C.K.A., and Perlman, D., "Conversion of L-Sorbose to 2-Keto-L-gulonic Acid by Mixtures of Immobilized Cells of Gluconobacter melanogenus IFO 3293 and Pseudomonas Species," *Eur. J. Appl. Microbiol.* 3:91-95, Springer-Verlag (1976).

"The Genetic Improvement of Product Formation," in *Molecular Biology and Biotechnology*, Walker, J.M., and Gingold, E.B., eds., Royal Society of Chemistry, London, Great Britain, pp. 15-20, The Royal Society of Chemistry (1988).

Tsukada, Y., and Perlman, D., "The Fermentation of L-Sorbose by Gluconobacter melanogenus. I. General Characteristics of the Fermentation," *Biotechnology and Bioengineering XIV*: 799-810, John Wiley & Sons, Inc. (1972).

Urbance, J.M., et al., "Taxonomic characterization of *Ketogulonigenium vulgare* gen. nov., sp. nov. and *Ketogulonigenium robustum* sp. nov., which oxidize L-sorbose to 2-keto-L-gulonic acid," *Int. J. Systematic Evol. Microbial.* 51:1059-1070, International Union of Microbiological Societies (May 2001).

Vandamme, E.J., "Production of Vitamins, Coenzymes and Related Biochemicals by Biotechnological Processes," *J. Chem. Tech. Biotechnol.* 53:313-327, Elsevier Applied Science (1992).

Yin, G.-L., et al., "Studies on the Production of Vitamin C Precursor 2-Keto-L-Gluconic Acid from L-Sorbose by Fermentation. I. Isolation, Screening and Identification of 2-Keto-L-Gluconic Acid Producing Bacteria," *Acta Microbiologica Sinica 20* (3): 246-251, Weishengwu Xuebao (1980).

Yin, G.-L., et al., "Studies on Production of Vitamin C Precursor 2-Keto-L-Gluconic Acid From L-Sorbose By Fermentation," *Acta Microbiologica Sinica 21* (2): 185-191, Weishengwu Xuebao (1981).

* cited by examiner

SEQ ID NO:1

```
   1 GCCATTTCTG CGCTGCACTT CGCTAAGGGT TCAAGGGAAA CGCAGGGTTC
  51 CCTTGCCCAC ACAAACGCGC AGCGTTTGTA TAAGTGGGCA CTTCGTGTTT
 101 GACACGCTAT CCACTACGCG GCACAAATTC AACTCTTGTA ACGAGGAAGG
 151 GCGGTAGAAT GGCGCGCACC ATCGACCAGC AGATCGCAGA TGCGCAAGCG
 201 AAGCTGGCGC GGCTCAAAAC CCGTCAGAAA GCCAGCGACA CCCGCCGAAA
 251 GATCATCGTC GGCGCCATCG TCACCACCGA GGCCCTGAAA GACCCCAAGA
 301 TTTCCAAATG GCTGGCATCT ACCCTGCGCA AGAACGCAAC CCGGGACGTG
 351 GACCAGAAGG AAATCGCCGG GCTGCTGGCC GACCTCGATG CCAGGGCGCA
 401 AAGCGCCGGG GCGGGTGAGG CATGAGCGGC AGCACCGATC CGTTTCTGGT
 451 TCTGGTCGAT GATATTGGCG CGCTGCGCCG CCAGATCGAG AACCTGCAAC
 501 GCACCAGCCT CGACAGGGAC GAGGCCGAAC ATCTCAACGC GACCATCGCC
 551 CAGAGCCTCG ACAACATGGC GCAAACCGGA AAACGGCTGG AACAGCGCCT
 601 TGAGGGCCAG TTGCAGCTCG CCACCGCCAA AACCCACAGG GACGCCATAG
 651 AAGCCGCTCA GGGGGCCGCC AGAGCGGCTA TCAGGGAATC CCATGCCGAG
 701 ATCCTCCAAA CGGCCAGGAG CCTCTCACAG GCCGCAGGAG AGGCCCGCAG
 751 AGAGGCGTGG CGCTGGTTCG GCGGGTTCTG GGTCTGGCTG GCCTCGATCG
 801 GGGCCGCAGG GGCGCTTGTC GGCGCGCTGG CCGTGTTCTG GCTCCAGGGC
 851 CGCGCCGATG CCAAAGCCTT CGGACAGTAT CCCAGCATCT ACTGCACCAC
 901 CGCAGGCGGG GCATTCGCCG ATCAGCGCGA CGGAAGCCGA TACTGCATCT
 951 TCATGATTTC ACCGCCGACA CAGCCAGACG GGGAATGACG GCTTACGCGC
1001 CGGGCTGGAT CGAGACTTTC AGCCCGAGCG CCTTAGCGAC CTTCATCACC
1051 GTGGACAGCG TAGGGTTCCC ATCCCCGGAT AGCGCCTTGT TCAGCCCCAC
1101 CCGGCTCATG CCAACCTCAC GGGCCAGCGC GGTCATGTTC CGTGCGCGGG
1151 CAACCACTCC AAGGGCGCGG GCAACATAGG CGGGATCGTC GCCGCCATCT
1201 TCCATGACCG CTTCGAGATA GGCCGCAATA TCTTCCTCGG TCTTGAGGTA
1251 GTCGGCGGAA TCGTAGCGGG CGAATTTTTC TTCCGGCATC GCTTAGCCCT
1301 TCCACTCTGC GGCCAGCACC TTGGCCTGTT TGATGTCTTT GCTCTGCGTG
1351 GACTTGTCGC CGCCACAAAG CAGGATCACG AGAACCGGCC CGCGCTGGAT
```

FIGURE 1A

1401 GAAATACACC CGGTAGCCCG GCCCGTAGTT GATCCGCAGT TCCGAAACAC

1451 CCTCTCCGAC CGGCTCCACA TCGCCGGGGT TCCCCGCCGC AAGGCGGTCC

1501 AGTCTGGCAG TGATGCGCGC AACCGCCCTG CGATCCCGCA AACCGGAAAG

1551 CCAGGTATCG AAGGTTCCGC TTCGGATTAA CTCGATCATT CGACAACTAT

1601 AGTTATCATG TGGGTGTCTG ACAACCAGAG TTATCACTTC CTTGTTCTAA

1651 GCAAATCCGA GGCCAGCCAC GGGCGTAGCC GGAGCATCAT CCCTCCCCCG

1701 CACCCCCACC CGTCACGCGC ACACATGCGC GGAATCGTCC ACTCGGCCCA

1751 CAAGGGGCCT TGCATCCGAT GGCAAGCAAA AACTACCCAG TCCGTCCGTA

1801 GGCGGGGGGT CGCCAGCCCT GTGGGTGGGC GCTTCCCCCC GGCCCGCAAG

1851 CGGGCCCGGA ATGGGCATTT TTTGCCTGCC CTAAGATCAT AAGAAGGGCA

1901 AAAAAAACAT CGTTTCAAAA CAGCGTGTTA CCACCCCCCT ATAGGACACC

1951 AGAGTCCGGG GTAGAGGACT CTGGTGTCCT CTTAGGCCAT TTATGTCCAA

2001 GAATGTGACA GCCAGCCGAG CGGAGGTAGA GGACTCTGGT GTCCTATGCT

2051 TAGGCCATTT ATGTCCAAAA ACTTGACAAG GGCCACATTC CTGCCAAATC

2101 TGTCCAGAAT TTGGAAAAAT TCGCCGGATA GTAGACAGTG GCAAAGCCTC

2151 CCCCCATTCC CGCAAAGCGC CCGCTCGGCA CTTGGGTTCA AACTGACCGG

2201 GAAGCCCACG AGGCGTGGGC GATACTGGCA AAAAAGCCTG CTGCCAGCGC

2251 TGTGATGCAC ATTCTGTGCG CCAACCTCGG TGAGCATAAT GCCGTGGTCA

2301 TCAGCCAGGA CACCATCGCC AAGCTGTGCG GCCTTTCCAC ACGGTCCGTC

2351 AGGCGCGCCA TCGTCGATCT GGCCGAAGGC CGATGGATCG AGGTTCGCCA

2401 ACTTGGCGCG ACCAGCCAGA CCAATGCCTA TGTCGTCAAC GACCGGGTGG

2451 CATGGCAGGG ATCACGGGAC GGACTGCGCT ACAGCCTGTT TAGTGCGGCT

2501 ATAGTCGTGT CCGAGGAGGA GCAACCCGAC CGCGCTGAAC TCGACCAGCA

2551 AGCCCCCCTG CGACACCTGC CACGCATCAG CGAGGGGCAG ATACCCACCG

2601 GCCCCGGCCT GCCGCCACCT TCGCAACCGT TTCTAAAAGA CATGGAGCCA

2651 GACTTGCCCA CCATTGACCG GGCAACATCA CCCAACTTTG ACCAGCAGGA

2701 ACAGGGGTGA AAAAGGTGGA CAAACTTTCC ATACGCGAGG CGGTAAAACA

2751 CTTCGATGTT TCCCGGCCAA CCCTGCAAAA AGCCCTTAAA TCTGGCAAGA

2801 TTTCAGGTGT TCAGGATGGA CAAGGAACGT GGACAATAGA CCCCTCAGAG

2851 ATGGCAAGAG TTTACCAGCC AAGGCAAGAT GAGGTGGTAA AGGATGGTGG

FIGURE 1B

| | | | | | |
|---|---|---|---|---|---|
| 2901 | CCAAGAACAT | GAAAATTTGT | CCGCCAAGAA | CACCCCTTTA | CATGGTCAAG |
| 2951 | TTGAGGTTCT | GAAAGAGCGG | CTTGCAGATG | CTGAAAAACG | GGTGGCGATA |
| 3001 | GCCGAGGCAC | TGGCCGAAGA | ACGTGGAAAA | CACATCGAGG | ATCTACGCCG |
| 3051 | GATGCTGCCT | GCACCGGAAG | CCGGTCAGCC | CCGCCGCCGC | TGGTGGCCAT |
| 3101 | GGTAAGGTCA | GCTATGCGGG | ACCAAGCCGC | AGCTCGCAAG | TGCGGCAACA |
| 3151 | GAATCAGACC | CGCTTCGGAC | AGAGAGCTCA | AGCTGGTGGA | AAACCGCCTG |
| 3201 | TGAAGCTGCT | GGGTGGCAGC | CGCTTTACTC | AGCGAAGCAG | CCATTCGGGC |
| 3251 | GGATCGCAGC | GAGATTGCCC | CATCCAGTCC | TAAGGGCCGT | GTAAACAGCA |
| 3301 | CTTAGTGCAG | CAGCATCGCA | GGCGCGGAAA | TCTGCCTGCC | CTTCCTCGCC |
| 3351 | ACCTCTGAGG | CGTCAGCGAT | CTGCCCCAAA | CCTGCCTGCC | ACTTTGGCGC |
| 3401 | AGCATGTTGC | TTGAGAACAC | GGAGCTGCCG | ATCTCTGCGC | TAAGCAGAAT |
| 3451 | TTCCTGATAA | TACGCACAGA | TGCAAATAAT | ATTGCGGCAT | CAATGCGTTT |
| 3501 | CCGTTTACCC | CTAGGCAGTT | GCCTCATCAT | GCTGTCGTTC | GCTGTCCAAG |
| 3551 | CCGCAACGAC | CTGCGACCGA | ACCTTCACTG | CATCTTACTT | TCGGCCCCTG |
| 3601 | CGTTCGCCCG | TGACCGCAGC | GCGGCCCAAA | GCGCGACCGC | CGCCAAGGCG |
| 3651 | GGTAGGAACA | GCCCCATTGC | CATCGGGAAC | GGGCTGTCGG | TCCCGGCCAA |
| 3701 | GGCCACGCAG | GTCGAAATCG | TGAAGGCCAT | CCCGAACTGC | ACCGCACCCA |
| 3751 | AGAGTGCCGA | TCCAGTTCCG | GCGGCCTCGG | TCGCGGCGGC | CATGGCAAGC |
| 3801 | GAGGTCGCAT | TGGCCGAAAG | CAGCCCGACC | ATGCCGATCG | CGATCCAGAG |
| 3851 | CGGAATGATA | AACATCCATA | CCGAACCCGT | GGCAGAGGCC | AGGACGGCTG |
| 3901 | CCAGCGCCGC | AAGACCATAG | AACGGCAGTC | CCCGGTTCAG | CATGTCCCGG |
| 3951 | GGCGTAAAGC | GGTCCAGGAG | GCGGCTGTTG | ATCTGCGCGA | AGACAAACAG |
| 4001 | CGCGGCTGCG | ATGAGCGCAA | ATATCAACCC | GTAGTTGAGT | GCGCTCATAC |
| 4051 | CGAAGAAGCC | CTGGAACACC | CCGGACGATC | CGGTGATGAA | GGCGAACATC |
| 4101 | CCGCCCTGGA | CCAACCCTGC | CACCAGCACG | GGGGCAAGGT | AGGCGGGCTG |
| 4151 | TCTGACAAGC | CGCAGGCCGT | TCCTTGTCGC | GCTTCGGAAG | GGCTGCGCGA |
| 4201 | CACGGCGCTC | TGGCGACAGC | GTCTCGGGCA | CCACCAGTTT | CGACAGGATG |
| 4251 | AGGGCAGGCA | GACCGACCAG | CACCATTGTC | ACGAAGATCG | ACCGCCAGCC |
| 4301 | GAAGGCCTCG | AGCAGCAGGC | TGCCAAGTGT | CGGCGCGATG | ACCGGACCTA |
| 4351 | TGGTCATCAG | CATCACCAGC | AAGGTCATCA | CCTTGGCCGC | CTTTTGCCCC |

FIGURE 1C

4401 GAGTAGAGAT CGGCGACGAT GGCCCTGCTG ACGACCATCC CCACGCAGGC

4451 CCCGATCGCC TGCAAAAAGC GCAGCGCGTT GAAGACAACG ATATTGTCGA

4501 CCAGCGGCAG CGCAATTGAT GTGACGGTGA AGATGAAGAC GCCGATCAGA

4551 AGCGGCCGCT TGCGCCCGTA TCCATCGGTC AGCGGCCCGA CGATCAGCTG

4601 CCCGAGGCAA AGGCCCAGAA AGAACAGCGA CAGTGAAAGC TCGGTCGCCG

4651 CATGGCTGGT ATTCAGATCC TCGGCGAGAA TGCCGATGGC CGAGAGATAC

4701 ATGTCGGTCG CCAGTGGCGG AAAGATCGAC AAAAGGGCGA GCACGGCGAT

4751 CAAGGCACCG GCTCGGGCAG GGATGAGGGG GCGGTCCAGC ATGATATCCT

4801 CTTGGCGGGA TGGTGCGATT CCATTTGTAG ATCGCAGTCT ACTAATGTAA

4851 AATTATACTC AAGTCTATAA TTCAAGTCGC TTGGCCGGAA TCGCAGGAGA

4901 AGACAGGAAT GCAGGAGGTA CGGAGCGGAC CGGGACGGCC AAAAGACCCC

4951 GTGGTTGCCG AAGCGATCCG CAAGGCGGCC CTGCGGCTGG TGCGCGAAAG

5001 GGGATACCGG AACGTAAGCA TCGGCGCGAT CGCGCAAGCC GCTGGAGTGG

5051 CGCGGCAAAC GCTTTACAAT CGCTGGCACG CGAAGGCCGA CCTCATCCTT

5101 GATGCCGTTT TCGAAGAGAC CGGGCGGCGC GCCGACGATC AATTACCGCT

5151 GGAAACAGGG GACGCGTCCC GTGATCGGCT GGAACGGCTT CTTATAGGTG

5201 TGTTCAATCA CCTCCGGGCG GATGGCGATA CACTGCGCGC ATTGATCGCC

5251 GCCGCGCAGG AGGACAGCGA GTTTCGTGAG GCCTTCCGGG AACGGTTCGT

5301 CGCACCGCGG GAAACCATCG TCACCGACAT TCTGGCCGAA GCCCTGCGCC

5351 GTGGCGAGCT TTCCCGGGAA GCCGACCCGG ATACCTTGTC GACCATGATC

5401 CACGGCGCAT TCTGGTATCG CCTCCTGAAC GGACGCGAGC TCGATCATGA

5451 ACTCGCCCGA TCAATAGCGC GGAGCGTGTT TCCCTGAGCC AAGACGAAAC

5501 GGAAACGGAC CCAAATCATC GGAATGTATA AAGTCGCGCA TCGTTACCAT

5551 CCTGAGGGGG TGATCGCTGC GGAGCGAGAC GAATGGCAGC TACCGGGAAT

5601 GCGGCCACGC CGCATTGGTC GAGGTCGGCC AGGGCAAAGG GCTGGCCTTC

5651 ACCTATACAA GCGACAGGCC TGCCATGCGG CGCCCTGCCC AAGTGTCAGC

5701 GATGGGCTCA AACCGTCGAT AGGCCAGCCC CGGCCCGCTC GTTCCATCGC

5751 GGGCTGTAGG GTCGGGGCTG GCCGGATCAG TGAGTAAGCC CGCCATCCCG

5801 GTCGTGGTCA CGGGCTTCTC GCTCCCGCAA CCGTTCCTGC TGCCGCTCTT

5851 GCTCCTTCAG GCGTTCGGCC TCCTGCACCC GCTGGCGTTC CTCGGCCTCC

FIGURE 1D

5901 CGGCTTTCCT GCAACCGCGC TGCCGCCTCG GCCAGCGTGC CCCGGTCGAT

5951 CCCCTGCGCC GCCTCCCGTA GCCGCTCGGC CAGGCTGCGG GAGGATTCCG

6001 GTTCCGGGGT TTGTCCAGGT GCAGCTATGG CATCGGACGC GGTGCGGCTC

6051 TGGCGGGCCT CCCATGCCTC GCGCAACCGC GCGGCCAGGT CCTGCCTCCC

6101 CTCCCGGCCA TCCCGATCCG CAGCGCCGGC ATAAGCCAGA CCCTGCGCCG

6151 CCCCCTCTTG CGTCAACGGC CCGAGGCGAT CCACAGCTCG CCCGATCCAG

6201 TCGCGCACCT GACCGGCCAG AACCTCCGCC ACACGCGCAA CCTCGGCCGC

6251 CTGCGCCTTG ACCTCGCGCC ACACCCGGAC GGCCCCGACC TCGATACCGC

6301 GTTCCTTCAT CTGCCACGCC CCGGCAGACA GTTGCGGCAA CGGATCCCGG

6351 TCCAGTTCCA CCGCCCGCAC CGTTTGACGC AGCGCCTCGG CCTCGTCGCC

6401 GCGATCATGC GCCGCGCTGG CCCGCTCCTG CGCCTCGATC CGCTGCGCCT

6451 CTAGCGTCCG GTGGTCGATC CGTTCCTCAT GGCCGCATCG CTCAAGGGCG

6501 CGGTTGCTGT CCCGCGCCCA TGCCTCACGC CATCCTTCCA GCATCTCGAC

6551 CGCGTTCCAG TCCCGGTTCT TCGCCCCGAA CCCCTCGGGG CCGATTTCGC

6601 GGGTGGTCAG CAGGATATGG GCATGGTGGT TGCGATCATC GCCGGTCCGT

6651 CCCGGCGCAT GAAGGGCAAT GTCGGCCACC ATGCCACGGG CCACGAACTC

6701 GCGCTGGCAG AATTCGCGCA CCAGCTCCAC GCGCTGTCCG TGGTCCAGCT

6751 CGGCGGGCAG AGCCACCCGG ATTTCGCGGG CGACCTGCGA ATTCTTCCGG

6801 GTCTCTGCCG CCTCGACCGC GTTCCACAGC GCCTCCCGGT CCTGCACCCA

6851 TGCGGGGGCG TTGGCAGGGG CGAGGGTTTC GACGTGATCG ACACCGCCAC

6901 GCGCACGGTA ATCGAAGGTC AGCCCGGTGC GGTGATCCTC GATCCGTTCG

6951 CCCACGCGGT AGGCCGCAGC CGCCGTGGCG CTACGACCGG AAGAGCGAGA

7001 TATCATCGTG GCCCGAAGGT GATAGATCG

FIGURE 1E

SEQ ID NO:2

```
   1 GCGTCTGTGC GCATACTATC CTCCGTGTTC ATCAGGCTCA CGCCTGATCT
  51 GATTAGGGCT CTTGTCTCTG CTTGTATCGT CGCCAAACTA TACTTTAAGC
 101 AGCGTCTAGA GCCTGATGAA CGATCTAAGA AGCCCGCCCC CTGAAAGGCG
 151 GGCTTTTTTG ATCTGTGCCA GATGTTGTTA CATCGGCGCT CAAAAATCAA
 201 GTTTTTTCTT GACTTTCAAT AATTTGCATT ATGCACATTA TTATCGTTTG
 251 ATAATAAGAG CCAGAACAGC ACAGAATAGT TGTGCGATAG CTATGAATAA
 301 TAGCAGATCC ATCCCTGTTT CCTTTCTTAC TAAATACAAT GCGAAACTGC
 351 TCGCATCTGT TTTATTTAGT TGAATCGGAA ACTCCAAATC GGCCGGATTC
 401 AAAAAAAATA TAGACTATCT TTAAAGTAGC AACGCCGCCG CTCGCGCGAC
 451 GGCATTGCGG GAAATGCGAT AGCAACAAAA CCACTTATTG TCGTATATCC
 501 CCACTTTCAA GCGAAGCGCC CCGCGAAGCG ATCAAAAAAG AAAGAAAGAA
 551 GGGGGCGCTG CCCCCGTCAT GCGCAAGCGC ATGACTCCCC CGCCCCTCAC
 601 TCACCAAAGC AGCAGCTACG AAGCAGGACG GGATCGGCGT TTGTGCATCA
 651 CGTGCTCGCA TCACCAACAC AAATAGACGT ATCCCCATGA ATGGGGCCCC
 701 ACGTCGATTT GTGTTGGCGC TACTGCGCGC GCAATGCCCT GCAGCCTCAC
 751 CCGACCGGCT CCGAAGCAGC AGCTTTTAAG ACAGTGAGTG ACACAAGAAA
 801 ACATGCGCAA GCGCATGTGT GCATCGCGTG CGCGCGATGC ACGGGAAGGT
 851 TGCCTTCGTT GTATATAATA ATATAGCCTG CACGCTGTGC GCACAGCGTG
 901 CATGAGAGGC AAAAACATGT CAAAAATGTT GACTACTGCA CAAGTTGCAC
 951 AGCGCTTTGG ACTGTCACGA TCGACAGTTA GCAGAGCGCT TAAAAACGGC
1001 GACTTGCGTG GCATCCGCGA CAATAGAGGC GTGTGGAAAA TTGCCGAAGA
1051 TGATGCGCAT AAATGGCGCA GCGACGCCGT GCATGAACAG CGTGCGCACA
1101 GCGTGCATGA CAGTGCATTA CGCACACGTG CTGAAGTTGC GGAAGCTCGT
1151 GCAACAGCGC TAGAAATGCA CGTGTCTGAC TTGCAAAGCG AGCGTGACGA
1201 CTTGCGAAAG CAGCGCGACG AGCTGCAAGC GAAGTTAGAC GGTCGGCCCG
1251 TCGAAACTGT CAGTATCAGC CAGCTTTTCG GGCGCCTTTT TCGGCGCTGA
1301 CATGGCGCGT AGAAGCGCGA CAGTCTCAGC TTTCGTTCGC TTCATCTGCG
1351 GCATGATCTT CACAGCATCA GTGCGTGCTG CGCGTGTCTC TTCGACCTCT
```

FIGURE 2A

1401 TTTCTAGAGC CGAGCCGCAA TGCAATCTGA ATAGATCTGC GTATTCGCGG

1451 CAAGCTTTTA CGCACTTCTG AAATCGCTTC ATCGAGCGAC TTCAAGCGCT

1501 CTACAAGAAT GCCGCGCAAG CCAGAAACTC GCTTGCGCTC AGCCCTGACG

1551 GCTTCGACAG CGACAGACTT TTGACGCTCA AAATCGACTT GTGCAGCATC

1601 GAGCTTTGCA CGCTCTGCAT CGAGCTGCTC GCGTTGTGTT TTAAGCTCTG

1651 TGCGCTCTGT CTCGACAGCT TTAAAAGCCT CAGTTTCTAA GCGATCCGGC

1701 GCGCCGTCCG ACTTCTCACG CTTAGGCTCT AGCTTGATGT TATTCCGACG

1751 CTCGAAAAAC GCAGCAAACT CGCTTTGCAG CGCAATACCG ACCGCGCGCG

1801 GCGCGCTATA GTTTGGCGCT GCCCCAGAAT GCCGCCGCTG GATCTCTTCG

1851 CGATGTTTAT CGGCCAGCTC GCGACCAAAT TTTGTGGCGC TCGACCACAT

1901 TTCGCCAGGC TGATCCGGCG GCGTTCTTTT CGTGCGCTTT TCATAAACTG

1951 GCGAAGCAAA AACATCGACG ATGCTCTCGC CCGCCTCGTC TCTGTCTAGC

2001 CTCGCTGCAA AGACAGCGTT ACCGCCGTGC GTTTCGTTTA TAAACTCCAC

2051 TGCTTGGCGC ACCATGGCGC GCTGCAGCTC TTCTTTGCTT CTGTTGGTTC

2101 TTCTCTCGTC AAGAAGCTCA GGCGGAAACC GCACTATAAA GTGCAGAACA

2151 GGCTTCTTCG CCGCTTTGTT TTGCCTAACG CCTTTTGTGT GCGCGTCATA

2201 TGCCGACCGA AGGTCTAGCG TCTTATAAAC GAGCGGAGAG GCATCTCTTA

2251 CGACGCGTTT CGCACTTGTT TTGTCTTGTC GTTTCGCGTG CTTTTCGGCT

2301 GCTGACAATC CAGCCATATC TAACGCACTA CATCTCACCG CTGCTTTCAT

2351 TTTCAATCCC TCATATATTA CCTTTTCTGT TGTTTTTGCG AAAAACGCAA

2401 AACTCGCTTT GCGTTTTTTG TTCGGCACCT GCGGCACCTC CAAAAAACAC

2451 GCTTGCTCTC CGAGGGTCTG GCAGGAGCCT AAGAGGGGGC ATTCTGCCCC

2501 TGATCGACCC CATTGAGGCT CGATCTAAAC AGACCCCCCA CAGGGGCGTC

2551 TGTGGGCCGC TAGTGCGGCC TTCCGCCATC TTCGAGCCAT CTGATCTCTG

2601 CAATTAGAGA TGCATGGCGC ATCTCCCATT CCAGCTCAGA TATCCCGTAT

2651 CTGTCGATGA CGGTGTCATA CAATTCGTCG AGCCTTGCTT CGCGCTCTTC

2701 TTTTGTCATG CCAGTTGCAT CGCGTTCTTC CATCTCCTCG TTCTCCTCTA

2751 TGATGAAATC ATTTTCGTCC TCGTCGTTTG GCCCGCTTTC TGCTGCCTTG

2801 ACCGCAACAG CGCCTCCGCG CTCTGCGGCC TCGAGCAAGT TCACGCGTTT

2851 AGCGCGCACT TGCTTCCACC CTTCATTGTC CCACTCCGCG ACAATTTCAG

FIGURE 2B

2901 GGCCGCTTTG CTCTGCTGCA TCAACTTCAG CCATAGCTTC ATCGTCATCC

2951 AGCTCGACCA AACCGCATTC TTCTTTCAAG CCTTGGCTCC ACACCAATTG

3001 CCGCCTACGC TTGCCGCTCG TTGCATTGAA ATATTCGAGC CAAAGCCCGT

3051 CATCGCCCGC CTGAAGTAGC TGCCTTGGCG TGCGTCCTTT GCGTTTTCCG

3101 CTCTTCGAGC TTGAAAGCGT CAACTCTTCG GCAGCGCCCC ACTTCGCTAC

3151 GTAGTCGCCC GCATTGGCAG CCCCGCGAAC GTCAAACGCC GCATCGTTGC

3201 CCCACATGCC ATACCCCTTC AGACATGCAC GCCACGCATC GCCTAGACGT

3251 TGCATCAGAT GCAGCGCTTC GCTTTCATCG CCAGCTCTTA GCAAGACAAT

3301 TTCGTGAAAG TGCGGGTGCC ACCCATTTGC ATAGCTATGA GTAATTTCAG

3351 TTGATGTGAC TGACCCAACA AATGGTAAAT CGCGCCACTC GCGGCGCTGA

3401 CGCAACCGCT GTTTCGCCTT CTTCATGTTT TGGAGAAGAT CAAAAAGCGA

3451 ATCACCTGCT TTGTGCTGGG CTGTCAGAGT TATGAGCACC GGCACAAACC

3501 CGTTGTCGCG CGCCCACGCG AGCAAGTGAT TCATTTCAGA ACGGCGAATT

3551 TGCGCGATGC GAGCGCTACA AACTGCGCAG CCCCACACAT TCCGGCACTG

3601 TGCTAGACCT GAAAAGAATG CCCGACGCCC GCCATCCTCG CCCACGTTTT

3651 GCACGTTTAG CTCAACTGTC GGAGACACTT TTACGTGCCG ACATTTCGCA

3701 ACTTGGTGGG GCTTGTTTTT GTTCAGATTC AACAGAATCC GAGCGGCTGA

3751 ACGCAGATCT GCATAAAGCT GCCGCCTACT GAATAACCTG TTGTTTTCTT

3801 TGTTTTTTTC ATTCGGTTGA CCCCCATTCT GGTCAACCGA TTTACGGTAT

3851 ATACCAAGGG GGGTCTGCCG ACCCCCTGAA AAAGCGTCAT CGCCGCGCGC

3901 CTGCGCACCC GCGTTCTTCT TCGATTTCTG AACTGAATGT GATGCTAGTT

3951 TGTGAGACAT GGCCGCAAAC CCCGACGGGT GCGGCGACTA TTCTCTTGAT

4001 TTTCT

FIGURE 2C

SEQ ID NO:3

1 CACTTTCGCC ACAAGATCAG GCGCATGATC TTTCTCAGCG TTCAACACAC
51 ATTTGAGCTC CTGCGCCTGA TCGTCAGTAA GGTAATATCG TTCTTGCATC
101 AATTTCTCCT TAGTTGGATT GGTTGCACTG GATCTTTGCC CTGACAGCCT
151 CATGCCTCGA GGCCTCGGCG ATGTCGTGGT GCATTGTATT CTCGCGGCAC
201 TGCATCGACT TCTTCTCGGT TTCCTTTTGT TCGCACTGGG TACATGGATG
251 TCGTTGCTGG TCACACACAC CAGAGCACAC CTACAGCTCT CCCATGCGAC
301 CGCCTTGGCC GCACCGAGAT ACATCGCCTT GTGTGGTTCG CGACTTCGGC
351 AGCAATCGCC GTGGCAGCTG GATTGGAGCA TCATCAGGCA AGGGCTTCGC
401 TGACAGCGTT CGTCGTGAAC GCCTAGGGGC TGTAAACCTA AAACTGCCCC
451 CATTGACCGC CGCCAGAAGA ATGATCCATG TCTAGGGTGC CCCATGAATT
501 ACCCGCGATA TCCGGTGTGC CGTCGCCTGC AACAGTAGGC AGACCGCTAG
551 CAGGATTGAT CGAGTGTATG CCACCAAATG TGCCCCCTGA AATATCCAGG
601 GTGCTCAATT CATCCATTGT ATGCGCTCCA GAGGTTGGGA TTGTGCTAAA
651 GGATTGAACA GTATGGTCTG GAGTACCCCA CCAGTTCAGA TTCAAAAAAC
701 TTCCTATCAT TTTGAACATG ATTGGCTTCC TTTTCGATTA AGTTTTCAAC
751 AAACAGAATT AATCTACGGG CCAGTTGTGT GCAGAAGAGC GACGGCAAAT
801 TGCTGTTATA GTATTTACGA AAATGGTCGC CAAAAAATAT CTGTCGATCA
851 AGTGTTTTCT GTAACCATCT GAACTTTTTG ATAAATATCA AGGTGTGAGT
901 GGTTTATGCG ATGCTTTACA TCTGACATCT GGTAACCGCC CCTGTTTTCT
951 CAGGGTGTAG AATGCAGATG ACACTGAAAA TACAATGAAG TGAATGAGAG
1001 CCGTTGCCCT GCCCAGCCAA GGCGAAGATT TCATTATCCG CTGAGCAAAT
1051 CTTGTACCAA AGAGGGCTTG CGTTCAATGA GGGCCAGTAG GACTTGAGCT
1101 GGCCCTTGAG GCATACGGCG CTTTTGCTCC CAGTTGAGAA GAGTGCCCTT
1151 CGCCACGCCG ATACTACGTG CAAACTCCGT TTGAGATAGG CCGGTCTGGG
1201 CGCGAATGCG CGCGACATCT ATCTCAGGCA AGCTGATCTC ATGCACAGCG
1251 GCACCGGCCT TTTGCCCAGT CGAAAAGGCG CGAGCTTCTT CCAAGCCCTG
1301 CATGATACTG TCGAACGCGC TCATTGTTTG TTGCTCCAAA TGGCGATGAT
1351 CTCTTTGCTC ATTTCGACCG CGGCCGCCTG TTCTGTCGGG GTTAGGTTCG

FIGURE 3A

1401 CCTTTTCGTT CTTGGCGAAA ACGGTGATCA GAAATATCGG CATGTGGCGG

1451 CCGCCAAACA CGTAGATCGT TCTGAACCCC CCACTCTTGC CGGCCCCTGC

1501 CCTAGGAATG CGGACCTTTC TCAATCCACC ACCCAAAGCG ATGCCGGCCT

1551 CTGGATTTTC TGCAATCCAA GCAATTGCAG CGTCACGTTC CGCATCGGTC

1601 ATGATCGATC GTGAGCGGCG CTGGAACTCT GGCAGTTCAA CTACGGTCTG

1651 CAGGCTTGTC ATTTAGGTAT ACTTCAATGG CGCATAAGTC AATGGCGCAC

1701 TACGGCTTCT TGAGCTGCTC AAGGAGCGCA ACAGCGTGTT CGAGGGTTTC

1751 ACCGAGGCCC CAACCGTTGG CATCTGCTAT TCTGTAAAAA GATTCTATCG

1801 TTTCAGGCGT CGCCTTAATG TTGAACTGCG CGTTTCGGCC AGTCCTACGG

1851 CGCCGCTGCG GCTTGGAAAC AGGGGGCGAT TTAGGCTCCC TGCTCACGAA

1901 GCCAGACGCC TCTGCCGCTT GTTCAGTGCT GCGGTCTTTA GGTGCTATCT

1951 TCGGAGCAGG CGCGAAGCTG CTAAGATCGT TTAGTGCATC ACCAAAACCA

2001 AGGTTTGCGC GTTGCTTGCT CATCACTGAT CCTCTTGGCT ACGCTTCAGC

2051 TTTCCAACCA CTTCGCCCGC AAATTGCCGC GCGTTCTCGA TTGCCTTATC

2101 GACGTTGCTG ACCTGCGACG GATCAAGGTC AGACAAGGTT CCGCCATAGT

2151 CGAACAAGTC ACGATAGGCC GCACGCTCGA CAATCGATGT TTCGCATATA

2201 TCGATGCCAC CGCTCATGAG CTGCTCGTGA ACGTTTTTCA GGGCGCGTGA

2251 GCGAACCGCG GCACTTGTTC GGGTCAGCAC AACGCAGTGC GGTATGGCAC

2301 GCCGCGCCAT CTTCGCTTGG TTGCTGATCA ATCGAATGGT TTTTGCGCCA

2351 CCTCTCGCAT CCATAGACGA GCCCTGTATC GGGATCAGTA CCAGGTCTGA

2401 CATACCGATA GCGTTTGCGA CCATCAGGCT CGCAGTCCCC TCTAAGTCGA

2451 CGATCACGAA TTGAGACGTG CCGGATGCCG CCTCAATCTG GTCAACAATG

2501 CCGTCTTCTG TCACGCCGCT TACGATGGAA ATATTTTCAG GCTTTCCGGG

2551 TAGGCTCGCC CATTGGGAGA TCCAGCGTTC TGGATCGGCG TCGATGATTG

2601 TGACGCTTGC CCCGCCCTCC GAAAGCTGCG TGGCCAAGAT CAAGGCTGAT

2651 GTTGTCTTCC CAGCCCCACC CTTTGGATTG GCGAATGATA TGACAGGCAT

2701 GTGTGATCGT CTCCGCGCTT TTAGGTACAA TATCAGATAG CTAACAGATA

2751 TCCATATATA AGTTACAGTA TCTAGTAGCT ATCGGATATC ATACAATACT

2801 AAAATGGTAC TATTTGGTAT CATATGCCAA ATATCTTGAC TTCATGACCA

2851 CTTGGTTCTG CGGCAGGTCC GACGAAAGAG CCCGGCGAGG ACGCTTACTT

FIGURE 3B

2901 TTTCTTTGGC TGCCATTTTT TTGCGAGCTT TAAAACGTTA CGACGGAGCT
2951 CATCGCCATC GGGGATATGT GGGTCGAATG GACCTTCTAC CCATTGGGTG
3001 AGTTCCTCGT GTTCAGGGTG TGCGGCGTCG CCGATTGCCT CGATGAAGTT
3051 TTCATATCCG GGCAGGCCGC CGACGTCCTC AGGCGGACAT CTACCGACAA
3101 CATCGACAAG CCGTGGGTAG AGGTTTTCGG GAATCGGATC GTCGACGCTC
3151 TCCGTCTCAA TCAGATGAAC CCAGTAATCT CCGAAATCGT AAACATATCG
3201 GATCGGGTCC GCTACGGCAG TGTTGATGAT GTCAGCTAGG ATGTCCGCTT
3251 CGGAGGTATC CTCGTAGACG CGGATCAGTG CGAAATTGGC CTTGAGCGCG
3301 GCCTTGTCCT TCAACTTGTC CCGTTCAATC ACTTTGCGCG CACTGGCGCT
3351 GTTTTTGCCG TGGTGGCCCG GCCCGTCATA TTCGATGATG GCGCGCACAA
3401 AGCCGTCCTT GCTCCAAATC ACGAAATCCG CGCGCTTTGC GACAAGGCCC
3451 CGCCACAGAT TGCCTTGAGC TTGGATGAAG GCACCGTATG GCACCTGCGG
3501 CGAGAGAATA AGATCAGGTC TGTTCTCGTG CCGCCAGCGG TTAAGCAGGT
3551 TATAGAGCCG AAATTCACTC TTATTCATCA ATTGCTTGCT GCTGTAGAGC
3601 GATTTTCGCC CTTCAACGAA CCAGTAGACA CCCCCGACAA GGGCGATGAC
3651 CACCAGAAAT CCAATTATCA TTGTGAAATT AATGTCGGTC ATGACTGCAC
3701 TCCCTCAAGG CCGAAGTCAG AGATTGCATC TTGACGCAGA GCGACGAGTT
3751 CAACGCCGTC GATGCGGTTT TGGGTGGCGG TAGCCGGGCT GGCGCGGATA
3801 CGCCTACCGT TGGCACGGTT TCTAGGCGAC ATACTGAGGC AAACCGGATT
3851 TCCAGTGGGC TGCGTGCTTT GTTGTAAGCG CGCCATTTCA TCCCCCCGAG
3901 GGCAGGGGAA CGGCTCACAA CTTCCAAAGG CCCCGAAAAA TTCTCGCGAT
3951 GACCCCACCA CGGGATTTGT GCAACACAAT CGGCGCGCGG GACAGGCTCA
4001 TATCAACTTG GATAAGCGCC GCGTTTTTTG CAAAATGCGA GAAAGTGCTT
4051 ATCCGCATCT TTCACGTTGA TGGCCTTGTC ATGCACCCAA GAACGCCACT
4101 CTTCTTCAAG GGAGTAAACA TCCCACCCAG GAGCAAGTTC ACGGGCAGTA
4151 TCGCGTGTGT CGGGATCGTT GAACGGCAAG GCCTGAAAAG TGGTTGATGC
4201 TATAGTTTCC ACCACCTTGG GTCGGAAGAC AGCGTTCTCT CCTTCGATAC
4251 TCATGCTGTA GTCAGGGAAG TGGTCGTGCG CGGTGTCATC CTCAATGATC
4301 TTCGAAAGCA GGCGACGGAA CTCTTTTTTA GTTGAGCCGG AACCGCACTT
4351 GTTTCGCAAG AGCTCCAAGC TACACATCCA TTTTGACTGC GCGCCACAAT

FIGURE 3C

4401 GCTTTCGCCC TATCTCATAC AACCGCCTTT CGAGGGGCTT TCTGAGCAGG

4451 AAATACCCCC GGCTTAGAGT GAGGACATGG TTGTTCTCGA TCGCATCAAA

4501 GACCCAGTCA GAGAGCGTTA TTTCGACATC AAGCATTCGG CCGTCGCGGG

4551 TTACGCGCAC GATCTCGGCT GATTCAATCA GGCCAAATAC CTTGAAGTAT

4601 TCTTTCCCAC CTTGACGAAT ATTCGTTTCA ATTTGGGTTC CCTGCAGCCG

4651 CCGAAGGGCA TCTTTGAGCA GCTGATAACC CTGACCGGAT GTCTGACGGT

4701 TCGTTGCCAC AAGCAGATCA TAAGCCTTGA AACGCATCGA TCTACTTATT

4751 TTCTGCCCCT CATTAATGGC CGCCATGCAC TGGCTGATGC AGTAGATCAG

4801 CACATCACGG TCATGAACGG TAGCAAGGCC ATAGCGTGAA GGGGAAACCT

4851 CGATCCAATT GTCGTTGTTC TGATAGCGGC GTGGCTTCAT GTCCGGCTTT

4901 GTAGACAGGG TGAACATAGG GTGCTCCATC GAAGCCATAT CCCCCTTGGG

4951 AACCGCATCA ACGATGTCGC AAACGAAAAG GTCTTTTTGT GGATGACGAT

5001 CCGGCAAAAG CGGTGATCGT AGGTTCGTCA TTTCACACAC TCCCGCGCCA

5051 AGTAAAAATT CGTCATTTCA CACACCGTAC AAGACTATCG TCATTTCACA

5101 CACCACTCGT CAAGGCTCGT CATTTCACAC ACCCAAGGAG GCTGTGGATA

5151 ACTCGAGCCG CTATCGTCAT TTCACACACC ATCTTTCGTC ATTTCACACA

5201 CCATCTTTCG TCATTTCACA CACCAGGTGT TATTTTTTTT ATAGTTATAT

5251 CAATTGATTA CGAGCTGTTT TCGGAGCTGT AACTCTATTC TAACTCTATT

5301 CTAACTCTCA TAGCTTGCCA AAATGGCACC TCATATCCCG GATATCCGGT

5351 TTCATTATGA AACCAATCAA CAACATTTAC GGTGTTTTTT GAGGAGCAAC

5401 ACTGTCCCAA CGCAGGTTCA AACCGATCAC GCCGAATCTG CAAAGAAAGG

5451 GGCAGTGCTA TGTTCATTTG GTCACTCGAG GATCACCCGA ACCACAGGTA

5501 AGCCCTCACA TGCTATGTTG ATACCTCCAG GGAAGTAGCA AAGGTCCTCA

5551 CGACCACCAC CTGCAGGATC TCCATCAGCG AAGACAACTG TCGCATTGAA

5601 CGCTGGCGCC GGCTTGTACG TACTCGGTAT GGGTGAGAAG TCAGGCATAC

5651 CTGGGAGAAC ACGACGAAGG ACACCGTGGT TCTCGAGGAT CCCGTAGAAG

5701 ATATCGGGCG TCCCATTATC CACATAAGCC GCACCATAGC GATCCTCCCC

5751 GTAGAGATAC TCACGGAAAG TTTGCATATG CCGCCAGCGA GAGCGAAAAA

5801 GGGGAACCCG AATAGCGAGA TCCTGATCGC CCAACCAAAT GTCAGCCATG

5851 ATGAACATGG AATATTGATT GTTCCACGAC GACAAAGCCG CAAATTCCAT

FIGURE 3D

5901 GAACCGTCTG ACCGCATGCA GGTCAGAGCG CTTTGGCTCC ATACGATGAA

5951 GAGGGTTTAC ATCTCGTTCA ACACTGCGAC GATCCGCCTT CTTCACCGCG

6001 CTCACAAATG GACTGCGATG TAATCGGCCC TCAAGGTAGC CTTCAAGCTG

6051 TTCCGCATAG GCCTCATCAC GCTTAGAGAC ACTCTCCAAG AGGCAGTCAG

6101 AAACGACCTG ACGCCAGTAC CCATTCCCAC GCGCTGTGTC GTGACCTATG

6151 ACGGGCCTCT GATTGTATCG CAGGGAGAGG TGCGTAACCG GAGACTCGAA

6201 GCTCTGAGAC CATTCCCAGA GGCTCTGAGC CATGGGATCC CACGAAGGAA

6251 GGTCCGTCTC TGGTTGCTCT ATCTCGCCAA AACCTAAATC CTGCAGCTGC

6301 ACATTCGCAG GATAGACTTT GAACATCGTT CGCACCTTGC CGAGGTCATG

6351 AACAAAGCCC GCGATAAAAG CCGCAAGATC GCCCGCCTCT GAGGGGACGG

6401 CCTTACTGAA CTCACTGTTG AAGAAATCTA CCGCAAGCCC AGCTGTTTCC

6451 AGGGAGTGAT AGAATAGCCC ACCGGCTGTG CGGTGGTGAT GTGTAGATGA

6501 AGCTGGGAGG CACAGCATAT AGTCGTGGCC TCCGCGCAAC ATTTGCCTCA

6551 CCAAGAGTGT TTCTTTGTGA GAGAGGAAGG GGAGTTTTTT GAGCTGCTCC

6601 TTGATCAGCT GCTCATAGCT TCCAAACGTC ACATGCGGGT GCAATATCCG

6651 GAACTGAGCG TTGCGCAGGT AGCGCCCGTA AGACAGGATG ATGCGATCGT

6701 CATAAAACAT TGGCGGTTTC CTCAATCGAT ATTTGCTCTT AGTTGGTAGG

6751 TGCCCGTATG GGCGCGGCAC AGGTTTCTCA GCTGTGCCAG GCGGTCAGTG

6801 CGATAGCGGA TCCAGGCGAA GTTGGCCTCG CACAGAAGCA GTTCTCTACG

6851 GATGGCGTCT GGAAAGCGCG CGAAGATCCG ATCGCTGTAT TTGTACTTTC

6901 CTGACATGCG GATCTGTTCG GTTGGGGTGA ACTTGTCACC TCCCATCCGG

6951 TAGCGGGCCT TGCCTTGGAA TTTGACCCAG TAAATGCGCG GGCCCAATGT

7001 GTCCTCGCGG ATTCGAACGA CAATGCCCAA ATTCAGCGCC TCGGCGCCCG

7051 CGTCCATTTT GCGATAGGCC TTCAGGGCTT CGACAGCCCG ATCCTGCCAA

7101 TAGCGCGCCC ATCCTTCCAA GTCATAACCC ATCGCTGGAA TGGATCGCAA

7151 AAGCTCAGGC TCCCAATCGG AGTCGAAATC ATGAAAGCGC ACTTCGTGCG

7201 AACAGCTCTC TTGGGGGTGT TCTTCAGACA TGCTGTGCTC CGACCAAATG

7251 GCGCGCCGAC CAAAACAAGA AGGTTGGGTT CAATGCCGGG ATGTTTCTGT

7301 CTGCGTTCAG ATAAAGCCCA TGTTTCCTAA TGTGACGGGA TGGTAGCTCC

7351 GTCACATTAG GGGGCGACGC ATTTTGCGCG GCACATGGCG CGGAGAGCCC

FIGURE 3E

7401 GCAGGCAGGC GGCTGGACGG ACGAAAATGG GCAGGGGCCG CGCTGAGATC

7451 CCTTGAAAGC CCATGGGCCT AATGAATGGC GCTCACACAG CCTGTCATGC

7501 GTGTACTTTA CGGGGAGGTC TCGCGATGAG GTGAGCGCCC GCGGTCTCTC

7551 GTCTTGGTCG TGTCTGACCG TATGTGTCCG TCGAATAAAC GTCATGATGA

7601 GGTCCTGAGA TAAGAACGAA CAGGATCGTT GACGGAGGGC ATCCGTCTGA

7651 CTGTCGTCTG ATGTTGATGG AAAGTCGCCG GCTCTAGGCG GCCGGTCTCA

7701 ATTTGGTGGT GAGCAGCTCT TTGCGCTGGG GGGCATTACG ATGCAGATCA

7751 GCCGTCCAGT TTAAATCGGG AGGGGTGAGG GAGGTCGGGG CGGCCGTGCA

7801 CAAGACAATG GCATCCGAAA GCCGGTCAAT CATTGGGCGT ATTTGTCCTA

7851 CCCATCTGTG CCAATTCATA GCAAAAATCC CGAACCATCC GTTTCGTCAC

7901 ACCTATTGGC TAGGGGGAGG TGGGGATGGC CGTCAATGAA AAATATCAGG

7951 GATTGAGTTT TATAATTAAC TGAAATTGCT AAATATTTTT GGAAGGAATA

8001 TTCCTTCCGT AGCTCGTCTA CTCATTTATC CCTTTTCGAA AAAAGACTTA

8051 ACAGCGGGCC AACTGTTTCG CATGATGCGG ACAAGAAAAA TTGGCTATCA

8101 TGGGAGTGTT CGGGTGGCGC GTGGGACTAA GACAGCCAAA AGCAAAAATG

8151 CTGATCCAAT TGTAGCAGAA TGCTTAAAAC TGATTCGCGA AGACAGTGGG

8201 TATGAGAGAG ATGAATTCGC CGAACTTCTA GGGGTGCAGC ATAAAACGTA

8251 TCGCAACTAC GAAGGCTGTA TATATCCGCT ACCGTTAAAA GTGGTAAAGA

8301 CGATACGTGA GAAGTTGGGC TATGATCTTG CGGATCCTGA TCTGACTTCA

8351 GACGCGATCA TCACCAAAAT TGCAGAGCAG CGACACGATG TTGCAGCCGC

8401 TCCTGATCTT GCCGCGACAG AGCAAGTAGC GAAGGGCGTT AGTTGCCCTC

8451 AGAGGATACG TACCTGCCTT CAAGCTTTCC GGCAGGAACT CATTGGTGTC

8501 CAGAGCAAGC GCAAGCATGA TATTCGAGAC GCAGTTTTTG TCGGAGCAGC

8551 TGCATTGTTT GCTTTCTGCT TGGTGGTACT ACGCACTGAA CCGCAAAATA

8601 TAAGGTTAGA GTCTATCTAT ACCCTTATGC TATCCGTGTC CTTCTTGGTT

8651 GCGGCGTCAA TTGTCCCGTT TCAGGCTATA CATATGATCC AAGCCGCCTA

8701 TCGGTCGCGA CGTTGACCAA CAATACTAGC CCTCCCCGTA TGCCCGTCTC

8751 ACAGGGAGGG CCAAAGCTAC CTTGGCGAAC GACTGTCAGT GCACGAAACG

8801 GGTGATTAAA CGCAAAGTGC TGACTTTTTT TCCCCCGATA CCGATGGTTC

8851 ATCAAAGATA TATCGACTGA GCAGATCGGT GTCCGGGGCA CGCGTGTGCA

FIGURE 3F

8901 TTGCTTCTAG GCCAGAAACT GTGAAGTTCT CTTCCACGTC GGATTCCGGC

8951 ACAAGGAGGT AATGCCAGGG CTTCTCACCG CTCTTTGCAC CGGCTTGCGT

9001 CGCAATATGG CACCACAGGC TTGCCGCATC TGCTTTACGC AGAACCTCGG

9051 TGGCGGTCAT TTCCGATTGG CGTTTTACCT CGATGATCAG CTTGCCTGTA

9101 TCGGTTTCGA CAACGAAATC GGGCTGATAC GGCGCACCGT GATTATCGAA

9151 AATTTTGAAC TGGTTGGGGC CAGGTTTCAT CCAAAGGCGG ACCGAGCTGT

9201 CTTTTTCAAG GATGATCGCC AGCTTGCGTT CTGGATTAGA GTCGAACTTC

9251 GCATACTGAT AGCAGCCCTT CACGAAGCCA GTGAAGATAT ACTTCCGGAT

9301 CTCCTGCTTT TGATCTGGCG GTGTTTTGAA ATCCCGGATG AAGCTCGTAC

9351 CGGCGGTATC GAAGGTCTGC GGACGCAGCT CGCCGAATGC AGAGGTCAGA

9401 GAAACACGGT AGTTCGTGTG CTCACGCCAC ATATTCTGCT TTATTTGCGA

9451 GAAAATGCTT TCGGCCATCG CCTTCGCATG CCCCCGGACG ACACTGCGAG

9501 TTTGCTCATC GTCGTCCGCG AAGCGGTTGC GGGTTTGGGT GACTGCCTGC

9551 CCAGCCAGAT CATACAAGAT GGCAGCATGG GCGTCATAGT CGATCTCAGG

9601 GTAGTCGATC AGCCGCGCGA CGATGTAATT CTCCAGCCGG TTTGCGGTGT

9651 CCCCCTTATC CTCGCTGGAA ATACGCGATG TCTTCTCTGT ACGCAGAGCT

9701 TGGATCATGA GCTCATTGGA CAACGGCTGG AAGTTCCAGC TCTTCATGTC

9751 CAGGTCGAAG CGCTTGAAGC CGAAGGAAAC TTGTTGCTGC GGAGTGATCG

9801 TGAGAGCAGG GATCGCAAGG GTCCGCTCCA CGAAATTCTT GCACAGCTCC

9851 TGAGCGACCG CGACGGCCTT TTCCTTCGTG ATGCTGGGAA GGAAACCTTC

9901 TTCGGGTTTC TGTGCTGCAA TGGCTGCTTC CGCGATGCGT TCGATCACCT

9951 TGGGGTCGTT GAGATCGCGG ATCGAGGACA CTTCCTTGCT GAGCTGGGGG

10001 ATCACAACAC TGAGCACCGT GCGGGCGACC TTCAGCTCTT CAGGCGTGCT

10051 GAAGCTGAAA GGCGCTTGGG TCGGTGCCGC AGACGTCGGC TTGGCGACTA

10101 GCTGCACAGG CGCGTCCGAA GCTTTTTCGT CATCCGCGAC GACGACTGTC

10151 GGCTCTGTCT TGGCCTCTGC CTGAGCAAGC ATCTGGTCGA GGATGGAGGG

10201 TGCCGAGACC GAAACAGGCT TCGAGGGCGG CACGTCACCA CCCTCACCAA

10251 TCGTCACCTG CTTCAGCTTG CGCGTGACGC CGTTCTCTTC CTTGGCTTTC

10301 TCGATCAGCT CGTTGAAGCG TTCGTGGGCA ATCACGGTCA GCGTGTCAAC

10351 CACTTCGACG CCGGTTCGCT TGCCATAGGG CAGGCGCAGA CCGCGACCGA

FIGURE 3G

10401 GCGTCTGTTC GGTTAGGATG TCCGAGGCCG AGGCGCGCAG CGGAACGATG

10451 GTGAACAGGT TCGAGACGTC CCAGCCTTCC TTCAGCTTGT TGACGTGGAT

10501 GACGATGTCC GTGTCGCCGG CCTTCTCGAT ATTCAGCAAA CGCTGTGCGT

10551 TCTCGTCGCT TTCCTCGCCG GTCAGCTTGG AGTGGATCTC GGCCACGCGC

10601 CCCTTGTAGC GTCCGCCGAA GAACTCGTCC GACTGGACGA ACTCATTCAC

10651 CTGCCGGGCA TGGGTCGTGT CCTGGGTAAC AACCAGCATG AAGGGCCGCA

10701 CCACCTTCAC GTCATTCTGG CGGGCATAGG TTTCCAGCGC CACCTTGACG

10751 TGCTCGTGGT AGTGGATGCC GTCTTCCAGC TTGATCCGTT CCAGCGTGTC

10801 TTCGTCGACG GTCTTCGGGT TGAAGTTCGC GCGGGTGCCG ACAGCCGGTT

10851 CCTTAACATA GCCGTCTTCC ATCGCGTCCG GCAGATCGTA GCGGTAGACG

10901 ACGTTCTTGA AGGGCTGCGA GCGCGCGCCA ACGGTCTTCG GGGTCGCCGT

10951 CACCTCAAGG CCGAGGATCG GTTTCAGCTC GGCAATCGCC CGCGCCCCGG

11001 CCGAACCGCG ATAGCGGTGC GCCTCGTCCA TCAGCAGGAC CAGGTCATCC

11051 AGTTCGGAGA GGTAGGAGAA GTAGCTCTCG CCGATATATT CCTGAAGGCG

11101 CTTGATCCGG GGGGCGTTGC CGCCGCGTGC TTCGGAGTTG ATCTTCGAGA

11151 CGTTGAAGAT GTTGATGATC GCGCCTTCTT GGCCGAAGAG GTCGGTGCCA

11201 CGCACACCGC GGCCTTCCTC GTAGTTCTCG GCGTTGACGA TCAGCGGCGC

11251 GTTATGGGCA AAGACTTCGA TGCCACGGAA GACGTATTTC GGGCTCGACG

11301 GCTGGAAGTC GGACAGCAGC TTTTCATAGA TCGTCAGGTT CGGGGCCAGA

11351 ACGAAGAAGT TCCGGCTTTT GCCGATCATG TAGAGGTAGC TGATGAAGGC

11401 GCCCATCAGG CGCGTCTTGC CCACGCCGGT CGCCAGCGCA AAGCAGACGC

11451 TCGGGAAGTC GCGCTCGAAC TCCTCGAAGG TCGCGTCGGC CAGGTCGCCA

11501 TAGACCTCGC GCACGGCGGC GCGGGCCATG TCGATATCGG CTTCCTTCGC

11551 GGGGCCGACG AGGTCGACGA TGTCATCGAG CCGCCGCAGC GCCTCGGCCT

11601 GCGGCTTGCG CAGCGACAGG CGTTGGTTGA TCTGAAGGAC GGCGCGTTTC

11651 GGGTCGGTCG TCTGCATGGC TCAGTTCTCC TCTGCGCCAA ACAGATCGGG

11701 TGTGTCTGCG GCTTTGGCCT TGGCCGATTT CTTCGGCGCG GGGGTGTCTT

11751 CGATGTCGTC CGGCTCATCC TCTGCCATCG GCAGGGCGTT GATCTTCAAG

11801 GAATAGTCAT CCTGCCCCCA TTCGCAGCGG TCAAGCACCA CGCGCGGGAT

11851 CTTCTTCAGG GTCAGGTTGC TCAGGCTTTC GCCCTGGGCC TCATAGGCCA

FIGURE 3H

11901 TGCAGCAGAT CAGCAGGCTG CGGTCCTCGC CCACCTCGTC CGAGATGGCG

11951 CGGAGCTGTT CGATGGTCAG GCTGGCCGTT GTCACATAGA TGAAGGCGTT

12001 CTCCGAAGCC TGACCGTGCA TCCAGTAGGC CTCGGTTGAG GGCGCGTAGA

12051 CATAGTTGAA ATGCTTGCAC ATGGCCTCGG CCAGCATCTC GGCATTGTAG

12101 TCCTTGGAGA TGACCCAGTT GCCCCAGACA TCCTTCTGAA GCAGAGATGG

12151 CGCAAGACGG AAGAAACGGT AGCCGCCGCC GCCTCTCCAG TTTGTGGCCT

12201 CGGTCACGCC GCCCTTATCG GTGCCGTTGA TGACTTTTTG CAGCCGAGGC

12251 GCGACATGGG TTTTGGCATG GTCCCCCAGC TCGACCATGA TCCAGCGGCG

12301 GCCCATCTTG TGGGCCACTG CACCTGTCGT GCCAGAACCA GCGAACGAGT

12351 CTATGACAAG GTCGCCCGGT TGAGTTCCTA TCTGTATAAT ACGCTCCAGC

12401 AGTTTTTCTG GCTTCGGTGT AGCGAACGTA GCGTCTCCCA AACCAAGAAG

12451 CGTGCGCAGG TCATTGGTTG CTTCACGGGT TGTACCAGCT TCTTCACCGA

12501 ACCAAATGCT CTCAGGTACG CGGCCTTCTT GATCGCAGAG ATAGATCTTC

12551 CGAAGAACAC GCGTGTCCTC GTTTAAGAAT GTAATTTCCC CGGTCTCTAC

12601 TTTGCTGGCA AAGGTCTCCT TTGACCACCT CCACCCTTTC TCTGGCGGCG

12651 GAATGATCTT CCCAGAAGGG GTAGTAACAT CGAACATGAG ATTTTCTCTG

12701 TAGTTCGGAC TACGTACATC TCCTGCTCGC CAAGGTCCTT TTGGATCTTT

12751 GTCTGGATTA TTATAGTTTT TGTTGTGCTC AGGCTTTCTG GGCAGAAGGT

12801 TGCGCGAGAA CGCCTCTGTT TTCCGATATG CTAGAACGTA ATTATGATGG

12851 AGACTGACGG TCTTGGCGTC ATTTTTCCCT TGAACGCTAT GCTGCCAGAT

12901 GATCGAGCCG AAGAAGTTCG ATCGGCCGAA AATCTCGTCG CACATAACCT

12951 TGAGGTAATG CACTTCGTTG TCGTCAATTG TCATCCAAAT GGAGCCGTCT

13001 TCAGAAAGTA GGTTCCGAAG AATTTCTAAC CGATCTCGCA TCATTGTCAG

13051 CCAAAGCGAG TGCTCCAGCC CGTCATCATA ATGCTCGAAG GCCGACCCGG

13101 TGTTATAGGG CGGGTCGATG AAGATGCACT TAACCTTGCC CCGCACGGCA

13151 GGGTCGGTTT CCAGCGCCTT GAGTGCCAGC AGGTTGTCGC CGTGGATCAG

13201 CATGTTGTCG AAGATGTCGC CCTCGCGCCG CGTGCTGGCG TGATGCGAGA

13251 ATTCCGGTTC TTCGATCAGA ATGCGGGGCT CAAGCCGCGG GCGGTTGTTC

13301 TTGCCGATCC AGGTCAGTTC AAGTTTGGTT TTGGCGGCCA TCAGGCAAGG

13351 GTCCATCTTA CAGTGAATAG GGTCGTCATT TCGGGGGTCA GGTTCAGCTG

FIGURE 3I

13401 ATCTGCGATG TCATCAAGCA TCCGCTCGCG CTCAGCGTCG ATTTCGCGCA
13451 GGCGGGTGTA AAGCTGGTGC TGAAGGTCAT CCACCTGCCG CTGCAAGGCC
13501 TTGGCCTCGC GTTGCAGGGT GACCTTTTCT TCCAGCCCGA TCGTGGCACG
13551 GGCCAGTTTC TTCTTCTCGG TCGCTTCCTT GTTCAGCGCC TTGATCTGCT
13601 GGTCGAAGGA CACCTTGGCA TCCTCGCGCC AGGCATCGAG CCGCTCTTCC
13651 TCCTCGTTGA GGAAGGAGCT GAGCCGATCC TGTGCCATGC CGATGATCGC
13701 GGTCTGGCGC GCGTTCAGGG TTTGGGTCAG GTCGCTTTCC GGCAGGGTGT
13751 CCGCGCCAAG GCCCTCGGTC GTCGCCGGGA CATAGAGCAT CCGAGAGGCC
13801 GTTTCCGGGT CGATGGCTGT TCCGCCGTCG CTGAAGGCTG CGAAGACCAG
13851 CTCGTCATAG ACCTTGGCTG GGGTTTTCAG TCGGACCCGC GCCACGCGCA
13901 TCCAGCCCGA CTGCCCCCTG AGCTGGGCCA CGTCGCCCAT GTTGCCCTGA
13951 TAGGCGCTAT AGTCGAGGCG CAGCATGGCA GGGACCAGAT CGCGCGACTT
14001 GGCCTTCTGG ACCAGCTGAT CGGCCAGCCC CTCGTCGCCA AGGCGGAAGA
14051 AACGCCAGCC GCGCTCGTCA GCCTCGGGCC ATTCGCTGGA CCAGGTTTCG
14101 CCCCCGTAAT CGAAGCGCTG CGCATGGTCG TCGTGGAAGC GGGCCTCCGG
14151 CAGCTCGGCC CGCGCGACAC CAAGGAGGGC GCGCTTGAAG TCACCGATGG
14201 CGGAATGCAC GGCGTCTTTC CGGCCAAGAA GCCGCTCGAT CACCTTGTCG
14251 TCCATCTCGG CCAGCAGCTG ATCTCGGACG TTCTTCTTCG CCTCGTCGAT
14301 CTCGACGCTG AACTCTTCCT GAAGGCGGTC GAAGGCGGCG TCGATCTGGT
14351 CCGTGGTGCG GCAGGACTGG ACGATGTCGA GGATGCGCCG CTCGATGTCG
14401 ACGCCGGATT CAATGACGCC CAGAACCTCG TCGGAGGAGC CGAACACACC
14451 CTCGAAAAGC TTGAACTTCT GTTCCAGAAG CTGGTGGATG CGCGCTTCAG
14501 CGTGGTTCTT CCGGTTCAGG AAGTTGATGA CGGTCACGTC GATCTTCTGG
14551 CCGTAGCGAT GGCACCGGCC AATGCGCTGT TCGACCCGCT GCGGGTTCCA
14601 GGGCAGGTCG TAATTGATCA GCAGGGAGCA GAACTGGAGG TTGATGCCCT
14651 CGGCGCCGGA CTCGGTCGCG ATCAGAATGG TGCGATCGTT GCGGAAGGCA
14701 TCGACGATGG CGGCCTTCAT ATCGGCGGTC TTGGAGCCCG AGACCACATT
14751 GGTGTCGCCG TGCTTGTCGA GCCAAGCCTT GTAGAGCGCT TTGCTGTCTG
14801 CGTCCGAGTT GGAGCCATTG AGGACGACGG TCTGTCCCTC GAAGCCGCTT
14851 TGTTCGAGCA GATCGCGCAG ATAGGTTTGC GTCCGCACGG ATTCCGTGAA

FIGURE 3J

14901 GATCACGGCC TTGCGCTGGC CGCCCTTGGA GACGATCTCG TCGAGCACGT

14951 TCGGCAGGCA GTCCAGGAGC GCCTTGCCTT TTGCGTTGTC CGAGATGGAT

15001 GCGGCCAGAT CGCGGTACTG GGTGAGCCGC TTGATTTCCG CTTCGAGCTG

15051 AGCGGGATCG ACGCGCTCAG CATCTTCGGT GTCGTCTTCG ATCGCGTCGG

15101 CTTCCGAACC GGAATCCGCC TCGCGCCAGT CCTCGGCTTC GTCGCTGAAA

15151 CCATCAAGGT CATCGAGCGT GTCTGCCCCG ACAACACGCT TCGCCTCAAG

15201 CCTGCGGATC ATCTTGTCGA GGGTCTGCAT CACGGCGAAG GAGGAAGATC

15251 CGAGGATCTT GCGCAGCATG AGCGTCACAA GATGACGCCC GTTCTGCCCC

15301 AAGGCGATGG TGCTGGGGTC TTGGAGATAC TCGGAAACCT TTTCGTAGAG

15351 ATCGGTTTCC AGTCGACCAG GCGTGAAGTC GAAGGTCTTG GGGAGACGGT

15401 TGGTATAGTT GATCAGGCCA GCGCGTTGGA CTTGGCGGCG CAGGGTTCGT

15451 TTGCAGATAG GCTCAAGACG TTTCGCGAGC AGGGCCTGAG AGGTCAGGCC

15501 TTCTCGTCCG CCAAACTCGC TTCGGAAGGC TTGTTCTGAA CCGAAGTAGG

15551 TTTCGTCGAT GATGCTGATG AGTCCGTACA GCTCCATCAG GTTGTTCTGA

15601 AGCGGAGTCG CCGTCAGAAG GAGTTTCTGA CGCCCAGCCA GTGCCTTTCG

15651 CAGAACCGAA GCCCGAGAGT TTTCGGCGGC CTTGTAGACG TTACGCAGCT

15701 TATGAGCTTC GTCGAATACC ACGAGGCTCC AAGGCGTGCG TCGCAGAGTG

15751 TCTGCAATTC GTGCGGCGTA CTCGTAGGAG ACGATGATAA TGCCTTCTCC

15801 GCGCCCTACC GGGTGCGGAG TGCCTTCGTT CTCAAGGTCT TTGACGCGCT

15851 TGGCATCAAG AATGAACGAT GGCAGCGAGA ATTTTTCACG CAGCTCGGTC

15901 GCCCACTGCT TGCGCAGAGA AGCAGGGACG ATGAGGAGAA TGTTTCTCTC

15951 ACGTTCCCAC CAGCGCTGGC TAATGACCAG CGCAGCTTCG ATTGTCTTCC

16001 CCAAGCCTAC TTCATCGGCC AGAAGAACGC CCTTCGACAA TGGTGAGCGT

16051 AGGGCAAATG TCGCAGCATC CACTTGGTGA GGGTTGAGGT CCACCTTGGC

16101 TGCCGAGAGG GACTGCGTCA GAGCGTCTTC TTCCTGAATG CCTTCGGATG

16151 TCAGGTGGTG CGCAAAGAAC TTTGATTGAT ATTCAGAAAA CTGGAAGAGC

16201 AATAGGTCAG GCTCCAAGGC ATATTAGTTA AGGGAAGGTT GTTCTAAATG

16251 CTGTCAAGTT ATGGCCTGCG GCTTGATCGG CCAGCACGAA GGACTCCCTT

16301 CTGCCCAGGA TATTGGGCCT TCTCGTTATC ACGCCACTGA AATGTCACCT

16351 GTACTGCGAT ACCATGCTTG TCGGCTATTC TGGAAACTTC CTTCCAAGCC

FIGURE 3K

16401 TCCTGGGCTG ATTGCCCTTG GATAGAGATG CCGAGGTCAG GGTAATATCG

16451 GAATCCTTCC TCTTCGTAGC ACGCCGTCTT GGTAGGAATC TGTATGGCCT

16501 CAGCTAGGTG ATCTCCGGAT AGGCCCTTAG CCTTAAGAGA ACTCACTGCG

16551 CCGAGAAGAA TTGCTGCCCA GTTTGGCTTG TCGATCTTCT TGTGATCAAC

16601 CTCCGCAGAT AAGACTTTTG TAAATGAAAG GCCTGGAGTG GATTTGAACT

16651 CCATGAAGCT GCTGATTTCC GACGTGGGAT CAATGCTGAT CTCGATGTCA

16701 CGCTCTAGGT CAAGCGCTGC CATCTTCTCC CGTACCAGCA GCATGATCGT

16751 TTCTGATGGG GTTTCTGTCC CCATCCAAGT CGAGATGCAC TTCAGATCGA

16801 CAAAAGTTGG GTCGTTCAGT CTGACTACGG GCATAGGCGT CATCCTTCTA

16851 TATTCATATA GAATATGTTA CATATTCAAT ATTATGGTGT CAATGCTAGC

16901 GTTTGATTGG CAACCTGTCC TAAAACGGTC GTTTTTGGGC ATAGTGGGAT

16951 GAAGTGGTCA AAATATAGGC CTTGATAATT TTGAACATGC GGCTACTTTT

17001 GGACAGGGTT TTTTGACACG GAGGGCCATA CATTGACAGA GCAAGGCCGT

17051 GTTTTTGCCT ATGTACGTGT CTCGACACTC GGGCAGACAG TCGCTGGACA

17101 GATGCAGGAA ATTGCGGCGG CTGGCTTTCA GCCCCCAGCG TATCGTGTCG

17151 TTTCGGAAAC CATCTCTGGC AGTGTCCCGG CGATGCGGCG ACCAGAGTTC

17201 GCGCGCCTAG TTGATCGCTT GGAACCTGGC GACATTCTAG TCGTGTCGAA

17251 GCTTGACCGT CTCGGACGCG ACGCAATCGA CGTTACGGAG ACAGTCGCTG

17301 CGCTCTCGCA GATACCTGTC CGAGTTCATT GCCTCGCTTT AGGTGGCACG

17351 GATTTGACTA GCTCGTCTGG ACAGTTGACG ATGAACGTCC TCAGCGCCGT

17401 TGCGCAATTT GAGCGCGATT TACTCCGTGA GCGGACCAGT GCAGGCCTTG

17451 CAGCTGCAAA AGCCAAGGGA AAACGACTAG GTCGTCCTAA AGTGCTGACC

17501 GAGGATAACG AGAGCGAAGC ACGAGCGGCT CTCGCCAGAG GGGAAACTGT

17551 TTCTGGGATT GCAAAGCGTT TCAACGTCAG TCGGGCGACG ATCGGCCGCC

17601 TAAGAGATAG TTAGGCTATC TTGCCTATGT CGTCGTGACG AGTCCTCCAA

17651 ATACACGGAT GGCTTCACGC TCCCATGCAC GATTAAACCA AGTAACATGG

17701 CGGCTTACTT GGTCCTTAAT CTCAGGGCAT CCCATGATGT CCGCTGCCTT

17751 GTAAGCATAC CGCAAGAAAT TTCGGCGTTT TCCAAGATGG GTATAACGCG

17801 CCAGGCTTTC TCGCTTGAAT ACTTCAAACG ACGGTACGTT TTTCGCCTTT

17851 GCGGCGATCA TCTTGGCATG AATGCCCCGG CGCATTTTTC CTCGGTAGGC

FIGURE 3L

17901 ATCGAGTGAC GAAGGTCGGA TCTTCGTTTT CTGCCCGTCG AAGGTGAAAC

17951 CCAAATACTG GATAGGTGTG GCAGAGGCCA ACAGTCCGTC CTTGAAGTCG

18001 GCAGTGTCTG TTTTGTCGAT GGACATGGAA AGGCAAAAAT CTGCCAGCAT

18051 TTTCTCTACT ACTGCAACCA CATGATGCAC CTTCGCGCCT AGAGGCAGAG

18101 TGACCGCGAT GTCATCAGAG TATCTTCGGT AAGATCCCCC TGCCCTAGAG

18151 CACCAAGCGA TCATTTCACG GTCAAAAGTT CGAAGATAGA TATTTGCATA

18201 CAGGCCGGAC ACCGGGGTGC CCTGCGGGAT ACCGAACGTC TGGTCATGCT

18251 TCCGAATGAG GCCATCCTTT CGGCCTCGGA CATGATCCGA AAAGTCTGAA

18301 GGTGAGCATA TCCTTCCGTG CCCATTTCGC TTTCGACCAA GAAGTTTGTC

18351 TAGATCTTCA GTCTCAACCC ATGAGTAGCG GGTCACGTTT TTCCAAACGC

18401 TTGCATGGTG CCCTTCCAGT CTTGTTTCGC CTATCAAATC GGCGATCTCA

18451 TCGCGGAGCA AGGTGTGATC GAGACAGTCA AAGAATCCGG AAATGTCCAT

18501 TGCGAAGACC GTGCAATCTC CACGAGACTT AATCTCGTCG AACAACGCCT

18551 TTGCATGGTG AATATTAGTG CCGCCCCCAC GGCGATAGGC TAGCACGGAG

18601 TCTGATGTGC CGTCGCGCCA TAGCGCCCGC TCGTACATTC TATTGAGATG

18651 TCCCGCGTAG GCTTGCAGGT AGGCTGCATC CTCATGACTG GCGAAGCGGA

18701 TCGGTCGCTC TTTCACTTTT ACCTCACGGG CGCCATCCTT GTTCCTGACA

18751 TACCTTCTGT TGACGTCAGT AAACCCAAGT AAAGGTAGAA ATCTGTGAGG

18801 CTTATCTTCG ACCGAGAAGT CAAACGACAG CTCCCGATCG ACTAACGGAA

18851 GATCGAAATG CTTGTATTTG CGTTCCTTGG ATATGGCCGG AAGCACAAAG

18901 TCGTCGGTTG ATGGATCAAA CTCGTTTTCA GACGGCAGGT AAAACCCGGG

18951 CATAGCGACT CCGTTCGTCA AATGCCCGGG CTATTGAACC TAGCTCCCAT

19001 CAACAGGCAC CGAGGTGCCC TCCGGTACGA GAAAACCTGG CGTGGTATGT

19051 TGTAACCACG ATGTGCGAAG GATGCGCCAT GACCGAAATC ACGACCACCC

19101 GGTGCCGCTG GGCGCGGGTA GCGCTTGCGG GCCTTAACAC TGGTCATCCG

19151 GGTCCACGCC CCGGGGCAAA ATATCAATTA GGTGCTACCT AATTGAATGC

19201 AAGGGGACGC ACCAAGAATA AAAGGACTTT TTCAGCTTTA GTGGCGCCTT

19251 ATAGTGGTCA TCTGGAACCA GGACAAAGAG ACAACCTTCT AGGTAAGATC

19301 CTCGTAAGTT CGTATCAGTT ACGGTGTCAG ATAGTAGCAG ATAACGCACG

19351 GCGTTCTGCT GGCGGAGGGC GAGAGAAATC TGGTTCGCTG TGAGCGGTAT

FIGURE 3M

19401 TTCTTGCCCA CAACGCGGCC CTTATTCCAG TCTAGTACAG GCTTGGCAGC

19451 CAATTGCCGC GACTGGCATA GCATCGTGCT CCTTGATTAC ATGCTAAAGA

19501 GGTACTTTGA GGTCTTAGCG GTCATTCGAC GATTTTGCTC AGATAACAGC

19551 GTAAGTAAAC GCTGCCCCAA GTTTCAGGAT CTAGCGCCCA ACGATCTTAT

19601 CACAAGAGAC CATGTTAATG CGTCTATTAC ATTAGGATGG TTCAAAGTTG

19651 GGTTCGGGAT CATCTGGTAT TGGGGTTCCA AAGACCAATT CGTGC

FIGURE 3N

SEQ ID NO:4

1 GCGTGGCCCT TCCCGCCGAG CTGGACGCCG AAGCCCAAGC CCGGCTTGTC
51 CGCACCTGGG CACGGGACCA CCTGGCCGCC GCCGGCATCG TCGCGGACAT
101 CGCCATTCAC GAGCCGAGCC GCGAAGGCGA CGACCGCAAC ACCCATGCCC
151 ACATCATGAC CACCCTGCGG CGTTTCGACG GGGCAACCGT GGACGGATGG
201 GCGAAGGGTG CCGCCCGCGA CCTGAACGAC AAGGCGTTCC TCGAGAACCT
251 GCGGGCATCG TGGGAGACCG CCCAGAACGC CGCACTGGAG GCCGCCGGGT
301 CAACCGCACG GGTTGACCAC CGCACCCTTG CCGCACAGCA TGAGGACGCC
351 TTGGCCGCAG GTGATGACTT ACTGGCCGCC GTCCTCAACC GCCCCCCGGA
401 ACCTCACCTG GGCGTGTCGG CCCAAGCGAT TGACCGCCGG GCCGGGCGTC
451 CGGTCAGCAA CCGGGGCCGG GCCTTGGCGG AGGTCAGGGA GACCCGCACC
501 CGGCTCATGA CGGCATACGA CACGGCACGG AGGGCCGCCG TGTTCATCGC
551 AACGACCACC GCCGGGCTTG TTGACCGGGT GTCCGGTGCC CGGTCAGAGA
601 CCGGACACCC CATTGCCCGA ATGTTCGGCC TTGGCCGTCA TGCGGCAACT
651 GTTGCCGACA CCGTGCCAGA ACCGTCCCGC CCATCGCCGG ACGACGATAC
701 CCCGTCCCCG TCCTGACCCG CCTCAAACCG TGCCGATGCA GCGGCCTCTT
751 TAAGCCCACT CTGTGCCTCT TCGGCGGCCC TGTGCTGTCT GGCCATCCAG
801 AAATCCAGAA TGGCCGCACC ACGCATGGCT TCGGCCTCGG CGTCCCGTGC
851 CTCGTCCAGA CCTGCCCGGA CCACCACCGC CTCAGCGGTT CCGTGCATGT
901 CCAGATGTGC GGCCACCATG TCCAACACGG CGGCCCTGAC TTCCTCGGGC
951 GACACCTCGG CCCCCATCCA ATCGTGGCCG AACTTCTCGG CCACGATGCG
1001 TGACACCGCC GCCTTGCAGA AGGTCCGGGC ATACTGCTCC AGACCGTATG
1051 CAGCCTTGTC CTCGACCGTC CGAGCGTCAG GCGCCTTGAT GACCCTCTGA
1101 ACTGCCATTG ATGCCCCTTT CTCGACTTCG ATTAGTGCCG CAATTTGCTC
1151 GACCATGCTA CGAACCCAAT GGACGGTCCC CAGCAGACGC CACGCCCCAT
1201 TCCGTGCCAG ACCTGCGGCC CCGGCCTTCT TGTCCGATTT GGGCGAAAAC
1251 CGGAACTCAA CCCGCACAAG ATGCGGGTCC GCGTCCTCGA TGGCCAACTT
1301 GCCGTCCGCC ACCCGTTCAA GGTCTTTCTG ATAAACCTTC ACGGACGCCT
1351 CACCCTTGCC CCAATAGAAG GTCCGGCCCG TGTCGCTCTC GATGACACGC

FIGURE 4A

1401 GGGGCCGCCA TCTTGGACGC CTTGGACATG CGGCGGGCAT AGTCCAGCAA

1451 GGCGTCCATC AAACCCTCTT GGCTATGGTC CATCGACACG TCAGCACGAG

1501 CCAGCAGGGA GGGACCAAAG GCGTTCAGGG CCTGCGGGGC CAGCAGCGCA

1551 CAACGACCAT CACCACCGGG TATTTCAAGG CTCGGCATGT TTCTGGCATG

1601 CCCTGCCCGC ACCGTAGCCC GGCGTTCCTC ATCAATGGGT GAGTCCGCGT

1651 AATGCAAGGC ACCCGCGAAA CCGTCCGTCC CGTTGCCCAC GCGTTGAGTG

1701 TGCAGACCAG CCAGCACAGA CCAGAGACAA AAGGCATCCC GTGCCTCTCT

1751 TGCCTCTTCC TCGCCCATCC TGTCCTCGTA GTGAATGACA CGCATGGCCT

1801 CAACGCGTTC AGTGCCCGTT AAGCGGGCAG CCTCGGCAAC CTCCGACGGG

1851 TCAGCCCTGC GGCGTTCGCC CTTGCCGTTC CGCCCGTTAG GCAACGTGAT

1901 TGTGAGCCAG TCGAAAAACC ACGCCGTTTG CAGCCATTTT TCCATGACCG

1951 GGCTGGTTTT CTTGCCCTTC CTTCGCTTCT CCGAAGGTGG GGGGCACTTT

2001 GGGGCACAAA CCGCCGGTTT TACGCCGTTC GGGGCCTGCT TTTCACATTG

2051 AAAATCAGGT GTTTGCCCCG AACTACCCCC CCTGTTAGCA TGTGGGGGGT

2101 TTTGGGCCTT GCGGCGGACC TCATCGAGAG CCGCGACCGC CTGCTGTGAA

2151 AGGGTTTTAC CGCCGTGGAC CATCATCGCG TCTCCCGTTG AGGGTGGACG

2201 CGGTCTCAAG CATGTTGATT CTTGCGAATG ACATGGCTAT ATCTCTCCAA

2251 AGTTCTGAGG ACGACGCGGG GACCGCGAAA TCACAGCGTT CGTCCAGGTT

2301 AAGGGCTCCG GTTAATCCCG GAGCCTTTCC ATTTCATATG AACGACATCC

2351 GGAAAAATCA ACATATTGAT GCCGCTGGAC GATGTGCGGC CAAGATGTGC

2401 TGCAGTATTC CCGGCGGGCG GAACCGTTCC GATATTTGAA GTCTCCACGC

2451 TTCCGCCCGC CTAATGTCGT TCTGTCGTTG AACTTTCATA AAGGTGAAAC

2501 CCTGCTGGTT TCCCCCGGCG GCGAAGCCGC CTCCCCCTTC CTGCCTCACA

2551 AAAAAAGGGA AAAGGCCCGT TTCAACCGAT CGACGCAATC TCCTTTCACG

2601 GTATCCAGAT ACCTTTTCTG GTGAAGCCAT CCGAAACAAA GGCCGCGAGT

2651 CGTCACACCT GGGCTTGACC GACGCGAATC ACTCGGACAG TGTCCGGTCA

2701 TGGACCACAT GCTGACCCCA AAACAGGCGG CGGCCCGTGC GGGCTGCGGG

2751 CGTTCCTCTA TCATGAGGGC GTTAAAGTCC CAATCTTTGC CCGCTATACG

2801 CGATAATGAG AACCGCTGGC AGATTGACCC GGACGCCCTT GACCGTTGGG

2851 CCGGTCACAG GCCGGACAAT GACCGGTCTA TGACCGAACA CGGACCGGCC

FIGURE 4B

2901 ACACCTTCGG ACACCCAAAC GGACACCCCG GAGACCTTGG CACGGCTCGC
2951 CGTTGCCGAG GCCCGGTTGA GTGATGCCCT GTCCCGCGTC GAAGATTTGC
3001 AGAGAGAACG GGATGAATGG CGGGCACAGG CACAAGCCTT GACCCGTCAG
3051 CCCGGTTGGC TGGACCGCCT ACTGGGTCGA ACCTGACCCC CCATCGTCAC
3101 CTTTGGCCTC ACCAGCGGAT TGCTTGTGAA CCAAGGCCAG CAGTTCCTTG
3151 ACCTGTTCCA CGCTACCCGC TTCGGCTTCA ATATCGCCCA TCTTGACGCG
3201 GACCTTTCGG CCTTGTCTCG CAGCCACCCA TCCACCGATA GCACCAATCA
3251 CAGCCGGACC GAGGGTTGTG GCCATCATCG TGAACTCACC CAAAAAAGTG
3301 ATGCCACCAG AGCCAGCCGA GTCCCTGATG AACGCTCGCT CCGAATATTT
3351 TATGTCCTGT TCTTTCAGGA TGGTGCGGAA CTCCCCGGCA TCTTCTTTCG
3401 GGAAAACCGC GATTTCTAAA TCACTCATGG AATGCTCCTT TTGCCCATGA
3451 GGTAATAATG CCCTGCCAAT GAGCACCGAG CAAATCAGCC GGGTTGCTCT
3501 TTCGAAACGG TCTCGGGCTT TGGAAGTGTC CACCCCTCGA ACAGTGCCCG
3551 GTCTCTCTCT GGCATCGAGG CAATCGCCAT CCGCAGCACC TTGACCCATT
3601 GAGGATCTTT TGCAGCTTGC CCGATAACCG CACCGCCCAG GACGATTTTC
3651 CGCCGTGCGT CCTTTTTTCG GTCCTCTGCC CGAAGTTTTG CCCCGGCTTG
3701 TCGTATCTGG GCCTCTGCCC TCGCCTTGGC CTCTTTGGCC CGCTCTAACT
3751 GCCTTTCTAC TGAAGTTCTT GCCATTTTCC GTCCTCCTTC ATAGGGCCTA
3801 TATGAACGGA GAGGGAACGA AGCAAGAAGT TCTCAAGAAC CCGAAGGGCG
3851 CACTTACACA AACTCTGGGG AGTTTGTTTC GGGCGCCCTA CCGGGGGTCA
3901 TCTCGCCGAT GGGGCGTCTC CGACGGTAAA AAGAGGAGGG GCCGCCGTGG
3951 CGATATATCA CCTGTCCGCG TCCATTATCG GGCGAAGCGA TGGCCGGTCA
4001 GCCGTTGCCG CGTCAGCATA TCGGGCCGGG GCCGACATGA CCGACCCGGA
4051 CACCGGGACG CGGCACGACT ACACCCGAAA GCGAGGCGTC CGGGCAACCT
4101 TCATGGAGTT GCCCGAAGGT GCCCCCGATT GGGCCACCGA CCGCCCGAGC
4151 CTCTGGAACG CCGTCCACGC GAAGGAGACG CGGAAGAACT CGCGGCTTTC
4201 GCGTGAGATC C

FIGURE 4C

SEQ ID NO:5

1 GGGCCTTGCA TCCGATGGCA AGCAAAAACT ACCCAGTCCG TCCGTAGGCG
51 GGGGGTCGCC AGCCCTGTGG GTGGGCGCTT CCCCCCGGCC CGCAAGCGGG
101 CCCGGAATGG GCATTTTTTG CCTGCCCTAA GATCATAAGA AGGGCAAAAA
151 AAACATCGTT TCAAAACAGC GTGTTACCAC CCCCCTATAG GACACCAGAG
201 TCCGGGGTAG AGGACTCTGG TGTCCTCTTA GGCCATTTAT GTCCAAGAAT
251 GTGACAGCCA GCCGAGCGGA GGTAGAGGAC TCTGGTGTCC TATGCTTAGG
301 CCATTTATGT CCAAAAACTT GACAAGGGCC ACATTCCTGC CAAATCTGTC
351 CAGAATTTGG AAAAATTCGC CGGATAGTAG ACAGTGGCAA AGCCTCCCCC
401 CATTCCCGCA AAGCGCCCGC TCGGCACTTG GGTTCAAACT GACCGGGAAG
451 CCCACGAGGC GTGGGCGATA CTGGCAAAAA AGCCTGCTGC CAGCGCTGTG
501 ATGCACATTC TGTGCGCCAA CCTCGGTGAG CATAATGCCG TGGTCATCAG
551 CCAGGACACC ATCGCCAAGC TGTGCGGCCT TTCCACACGG TCCGTCAGGC
601 GCGCCATCGT CGATCTGGCC GAAGGCCGAT GGATCGAGGT TCGCCAACTT
651 GGCGCGACCA GCCAGACCAA TGCCTATGTC GTCAACGACC GGGTGGCATG
701 GCAGGGATCA CGGGACGGAC TGCGCTACAG CCTGTTTAGT GCGGCTATAG
751 TCGTGTCCGA GGAGGAGCAA CCCGACCGCG CTGAACTCGA CCAGCAAGCC
801 CCCCTGCGAC ACCTGCCACG CATCAGCGAG GGGCAGATAC CCACCGGCCC
851 CGGCCTGCCG CCACCTTCGC AACCGTTTCT AAAAGACATG GAGCCAGACT
901 TGCCCACCAT TGACCGGGCA ACATCACCCA ACTTTGACCA GCAGGAACAG
951 GGGTGAAAAA GGTGGACAAA CTTTCCATAC GCGAGGCGGT AAAACACTTC
1001 GATGTTTCCC GGCCAACCCT GCAAAAAGCC CTTAAATCTG GCAAGATTTC
1051 AGGTGTTCAG GATGGACAAG GAACGTGGAC AATAGACCCC TCAGAGATGG
1101 CAAGAGTTTA CCAGCCAAGG CAAGATGAGG TGGTAAAGGA TGGTGGCCAA
1151 GAACATGAAA ATTTGTCCGC CAAGAACACC CCTTTACATG GTCAAGTTGA
1201 GGTTCTGAAA GAGCGGCTTG CAGATGCTGA AAAACGGGTG GCGATAGCCG
1251 AGGCACTGGC CGAAGAACGT GGAAAACACA TCGAGGATCT ACGCCGGATG
1301 CTGCCTGCAC CGGAAGCCGG TCAGCCCCGC CGCCGCTGGT GGCCATGGTA
1351 AGGTCAGCTA TGCGGGACCA AGCCGCAGCT CGCAAGTGCG GCAACAGAAT

FIGURE 5A

1401 CAGACCCGCT TCGGACAGAG AGCTCAAGCT GGTGGAAAAC CGCCTGTGAA

1451 GCTGCT

FIGURE 5B

SEQ ID NO:6

1 CACCATGGCG CGCTGCAGCT CTTCTTTGCT TCTGTTGGTT CTTCTCTCGT

51 CAAGAAGCTC AGGCGGAAAC CGCACTATAA AGTGCAGAAC AGGCTTCTTC

101 GCCGCTTTGT TTTGCCTAAC GCCTTTTGTG TGCGCGTCAT ATGCCGACCG

151 AAGGTCTAGC GTCTTATAAA CGAGCGGAGA GGCATCTCTT ACGACGCGTT

201 TCGCACTTGT TTTGTCTTGT CGTTTCGCGT GCTTTTCGGC TGCTGACAAT

251 CCAGCCATAT CTAACGCACT ACATCTCACC GCTGCTTTCA TTTTCAATCC

301 CTCATATATT ACCTTTTCTG TTGTTTTTGC GAAAAACGCA AAACTCGCTT

351 TGCGTTTTTT GTTCGGCACC TGCGGCACCT CCAAAAAACA CGCTTGCTCT

401 CCGAGGGTCT GGCAGGAGCC TAAGAGGGGG CATTCTGCCC CTGATCGACC

451 CCATTGAGGC TCGATCTAAA CAGACCCCCC ACAGGGGCGT CTGTGGGCCG

501 CTAGTGCGGC CTTCCGCCAT CTTCGAGCCA TCTGATCTCT GCAATTAGAG

551 ATGCATGGCG CATCTCCCAT TCCAGCTCAG ATATCCCGTA TCTGTCGATG

601 ACGGTGTCAT ACAATTCGTC GAGCCTTGCT TCGCGCTCTT CTTTTGTCAT

651 GCCAGTTGCA TCGCGTTCTT CCATCTCCTC GTTCTCCTCT ATGATGAAAT

701 CATTTTCGTC CTCGTCGTTT GGCCCGCTTT CTGCTGCCTT GACCGCAACA

751 GCGCCTCCGC GCTCTGCGGC CTCGAGCAAG TTCACGCGTT TAGCGCGCAC

801 TTGCTTCCAC CCTTCATTGT CCCACTCCGC GACAATTTCA GGGCCGCTTT

851 GCTCTGCTGC ATCAACTTCA GCCATAGCTT CATCGTCATC CAGCTCGACC

901 AAACCGCATT CTTCTTTCAA GCCTTGGCTC CACACCAATT GCCGCCTACG

951 CTTGCCGCTC GTTGCATTGA AATATTCGAG CCAAAGCCCG TCATCGCCCG

1001 CCTGAAGTAG CTGCCTTGGC GTGCGTCCTT TGCGTTTTCC GCTCTTCGAG

1051 CTTGAAAGCG TCAACTCTTC GGCAGCGCCC CACTTCGCTA CGTAGTCGCC

1101 CGCATTGGCA GCCCCGCGAA CGTCAAACGC CGCATCGTTG CCCCACATGC

1151 CATACCCCTT CAGACATGCA CGCCACGCAT CGCCTAGACG TTGCATCAGA

1201 TGCAGCGCTT CGCTTTCATC GCCAGCTCTT AGCAAGACAA TTTCGTGAAA

1251 GTGCGGGTGC CACCCATTTG CATAGCTATG AGTAATTTCA GTTGATGTGA

1301 CTGACCCAAC AAATGGTAAA TCGCGCCACT CGCGGCGCTG ACGCAACCGC

1351 TGTTTCGCCT TCTTCATGTT TTGGAGAAGA TCAAAAAGCG AATCACCTGC

FIGURE 6A

```
1401  TTTGTGCTGG GCTGTCAGAG TTATGAGCAC CGGCACAAAC CCGTTGTCGC
1451  GCGCCCACGC GAGCAAGTGA TTCATTTCAG AACGGCGAAT TTGCGCGATG
1501  CGAGCGCTAC AAACTGCGCA GCCCCACACA TTCCGGCACT GTGCTAGACC
1551  TGAAAAGAAT GCCCGACGCC CGCCATCCTC GCCCACGTTT TGCACGTTTA
1601  GCTCAACTGT CGGAGACACT TTTACGTGCC GACATTTCGC AACTTGGTGG
1651  GGCTTGTTTT TGTTCAGATT CAACAGAATC CGAGCGGCTG AACGCAGATC
1701  TGCATAAAGC TGCCGCCTAC TGAATAACCT GTTGTTTTCT TTGTTTTTTT
1751  CATTCGGTTG ACCCCCATTC TGGTCAACCG ATTTACGGTA TATACCAAGG
1801  GGGGTCTGCC GACCCCCTGA AAAAGCGTCA TCGCCGCGCG CCTGCGCACC
1851  CGCGTTCTTC TTCGATTTCT GAACTGAATG TGATGCTAGT TTGTGAGACA
1901  TGGCCGCAAA CCCCGACGGG TGCGGCGACT ATTCTCTTGA TTTTCTGCGT
1951  CTGTGCGCAT ACTATCCTCC GTGTTCATCA GGCTCACGCC TGATCTGATT
2001  AGGGCTCTTG TCTCTGCTTG TATCGTCGCC AAACTATACT TTAAGCAGCG
2051  TCTAGAGCCT GATGAACGAT CTAAGAAGCC CGCCCCCTGA AAGGCGGGCT
2101  TTTTTGATCT GTGCCAGATG TTGTTACATC GGCGCTCAAA AATCAAGTTT
2151  TTTCTTGACT TTCAATAATT TGCATTATGC ACATTATTAT CGTTTGATAA
2201  TAAGAGCCAG AACAGCACAG AATAGTTGTG CGATAGCTAT GAATAATAGC
2251  AGATCCATCC CTGTTTCCTT TCTTACTAAA TACAATGCGA AACTGCTCGC
2301  ATCTGTTTTA TTTAGTTGAA TCGGAAACTC CAAATCGGCC GGATTCAAAA
2351  AAAATATAGA CTATCTTTAA AGTAGCAACG CCGCCGCTCG CGCGACGGCA
2401  T
```

FIGURE 6B

SEQ ID No:7

```
   1  AGAGAATAAG ATCAGGTCTG TTCTCGTGCC GCCAGCGGTT AAGCAGGTTA
  51  TAGAGCCGAA ATTCACTCTT ATTCATCAAT TGCTTGCTGC TGTAGAGCGA
 101  TTTTCGCCCT TCAACGAACC AGTAGACACC CCCGACAAGG GCGATGACCA
 151  CCAGAAATCC AATTATCATT GTGAAATTAA TGTCGGTCAT GACTGCACTC
 201  CCTCAAGGCC GAAGTCAGAG ATTGCATCTT GACGCAGAGC GACGAGTTCA
 251  ACGCCGTCGA TGCGGTTTTG GGTGGCGGTA GCCGGGCTGG CGCGGATACG
 301  CCTACCGTTG GCACGGTTTC TAGGCGACAT ACTGAGGCAA ACCGGATTTC
 351  CAGTGGGCTG CGTGCTTTGT TGTAAGCGCG CCATTTCATC CCCCCGAGGG
 401  CAGGGGAACG GCTCACAACT TCCAAAGGCC CCGAAAAATT CTCGCGATGA
 451  CCCCACCACG GGATTTGTGC AACACAATCG GCGCGCGGGA CAGGCTCATA
 501  TCAACTTGGA TAAGCGCCGC GTTTTTTGCA AAATGCGAGA AAGTGCTTAT
 551  CCGCATCTTT CACGTTGATG GCCTTGTCAT GCACCCAAGA ACGCCACTCT
 601  TCTTCAAGGG AGTAAACATC CCACCCAGGA GCAAGTTCAC GGGCAGTATC
 651  GCGTGTGTCG GGATCGTTGA ACGGCAAGGC CTGAAAAGTG GTTGATGCTA
 701  TAGTTTCCAC CACCTTGGGT CGGAAGACAG CGTTCTCTCC TTCGATACTC
 751  ATGCTGTAGT CAGGGAAGTG GTCGTGCGCG GTGTCATCCT CAATGATCTT
 801  CGAAAGCAGG CGACGGAACT CTTTTTTAGT TGAGCCGGAA CCGCACTTGT
 851  TTCGCAAGAG CTCCAAGCTA CACATCCATT TTGACTGCGC GCCACAATGC
 901  TTTCGCCCTA TCTCATACAA CCGCCTTTCG AGGGGCTTTC TGAGCAGGAA
 951  ATACCCCCGG CTTAGAGTGA GGACATGGTT GTTCTCGATC GCATCAAAGA
1001  CCCAGTCAGA GAGCGTTATT TCGACATCAA GCATTCGGCC GTCGCGGGTT
1051  ACGCGCACGA TCTCGGCTGA TTCAATCAGG CCAAATACCT TGAAGTATTC
1101  TTTCCCACCT TGACGAATAT TCGTTTCAAT TTGGGTTCCC TGCAGCCGCC
1151  GAAGGGCATC TTTGAGCAGC TGATAACCCT GACCGGATGT CTGACGGTTC
1201  GTTGCCACAA GCAGATCATA AGCCTTGAAA CGCATCGATC TACTTATTTT
1251  CTGCCCCTCA TTAATGGCCG CCATGCACTG GCTGATGCAG TAGATCAGCA
1301  CATCACGGTC ATGAACGGTA GCAAGGCCAT AGCGTGAAGG GGAAACCTCG
1351  ATCCAATTGT CGTTGTTCTG ATAGCGGCGT GGCTTCATGT CCGGCTTTGT
1401  AGACAGGGTG AACATAGGGT GCTCCATCGA AGCCATATCC CCCTTGGGAA
```

FIGURE 7A

```
1451  CCGCATCAAC GATGTCGCAA ACGAAAAGGT CTTTTTGTGG ATGACGATCC
1501  GGCAAAAGCG GTGATCGTAG GTTCGTCATT TCACACACTC CCGCGCCAAG
1551  TAAAAATTCG TCATTTCACA CACCGTACAA GACTATCGTC ATTTCACACA
1601  CCACTCGTCA AGGCTCGTCA TTTCACACAC CCAAGGAGGC TGTGGATAAC
1651  TCGAGCCGCT ATCGTCATTT CACACACCAT CTTTCGTCAT TTCACACACC
1701  ATCTTTCGTC ATTTCACACA CCAGGTGTTA TTTTTTTTAT AGTTATATCA
1751  ATTGATTACG AGCTGTTTTC GGAGCTGTAA CTCTATTCTA ACTCTATTCT
1801  AACTCTCATA GCTTGCCAAA ATGGCACCTC ATATCCCGGA TATCCGGTTT
1851  CATTATGAAA CCAATCAACA ACATTTACGG TGTTTTTTGA GGAGCAACAC
1901  TGTCCCAACG CAGGTTCAAA CCGATCACGC CGAATCTGCA AAGAAAGGGG
1951  CAGTGCTATG TTCATTTGGT CACTCGAGGA TCACCCGAAC CACAGGTAAG
2001  CCCTCACATG CTATGTTGAT ACCTCCAGG
```

FIGURE 7B

SEQ ID NO:8

```
  1  MHILCANLGE HNAVVISQDT IAKLCGLSTR SVRRAIVDLA EGRWIEVRQL
 51  GATSQTNAYV VNDRVAWQGS RDGLRYSLFS AAIVVSEEEQ PDRAELDQQA
101  PLRHLPRISE GQIPTGPGLP PPSQPFLKDM EPDLPTIDRA TSPNFDQQEQ
151  G*
```

FIGURE 8

SEQ ID NO:9

1 MSHKLASHSV QKSKKNAGAQ ARGDDAFSGG RQTPLGIYRK SVDQNGGQPN

51 EKNKENNRLF SRRQLYADLR SAARILLNLN KNKPHQVAKC RHVKVSPTVE

101 LNVQNVGEDG GRRAFFSGLA QCRNVWGCAV CSARIAQIRR SEMNHLLAWA

151 RDNGFVPVLI TLTAQHKAGD SLFDLLQNMK KAKQRLRQRR EWRDLPFVGS

201 VTSTEITHSY ANGWHPHFHE IVLLRAGDES EALHLMQRLG DAWRACLKGY

251 GMWGNDAAFD VRGAANAGDY VAKWGAAEEL TLSSSKSGKR KGRTPRQLLQ

301 AGDDGLWLEY FNATSGKRRR QLVWSQGLKE ECGLVELDDD EAMAEVDAAE

351 QSGPEIVAEW DNEGWKQVRA KRVNLLEAAE RGGAVAVKAA ESGPNDEDEN

401 DFIIEENEEM EERDATGMTK EEREARLDEL YDTVIDRYGI SELEWEMRHA

451 SLIAEIRWLE DGGRPH*

FIGURE 9

SEQ ID NO:10

| | | | | | |
|---|---|---|---|---|---|
| 1 | MTNLRSPLLP | DRHPQKDLFV | CDIVDAVPKG | DMASMEHPMF | TLSTKPDMKP |
| 51 | RRYQNNDNWI | EVSPSRYGLA | TVHDRDVLIY | CISQCMAAIN | EGQKISRSMR |
| 101 | FKAYDLLVAT | NRQTSGQGYQ | LLKDALRRLQ | GTQIETNIRQ | GGKEYFKVFG |
| 151 | LIESAEIVRV | TRDGRMLDVE | ITLSDWVFDA | IENNHVLTLS | RGYFLLRKPL |
| 201 | ERRLYEIGRK | HCGAQSKWMC | SLELLRNKCG | SGSTKKEFRR | LLSKIIEDDT |
| 251 | AHDHFPDYSM | SIEGENAVFR | PKVVETIAST | TFQALPFNDP | DTRDTARELA |
| 301 | PGWDVYSLEE | EWRSWVHDKA | INVKDADKHF | LAFCKKRGAY | PS* |

FIGURE 10

*KETOGULONIGENIUM* ENDOGENOUS PLASMIDS

CROSS-REFERENCE TO RELATED APPLICATIONS

This non-provisional application is a divisional application of U.S. application Ser. No. 09/826,191, filed Apr. 5, 2001, now abandoned, which claims the benefit of U.S. provisional Application No. 60/194,627, filed Apr. 5, 2000, the contents of each of which are incorporated herein by reference.

BACKGROUND OF THE INVENTION

1. Field of the Invention

The present invention relates, in general, to a novel genus of bacteria known as *Ketogulonigenium.* The present invention further relates to transformed *Ketogulonigenium,* and methods of transforming *Ketogulonigenium.* The present invention also relates to nucleic acid molecules, and vectors.

2. Background Art

The exploitation of microorganisms to synthesize vitamin C or its chemical pathway intermediates has both economic and ecological advantages. One key intermediate in vitamin C synthesis is 2-keto-L-gulonic acid (2-KLG), which is easily converted chemically to L-ascorbic acid (vitamin C) by esterification followed by lactonization (Delic, V. et al., "Microbial reactions for the synthesis of vitamin C (L-ascorbic acid," in *Biotechnology of Vitamins, Pigments and Growth Factors,* Vandamme, E. J., ed., Elsevier Applied Science (London & New York) pp. 299–336 (1989)). Members of a number of bacterial genera have been identified that produce 2-KLG from the oxidation of L-sorbose or sorbitol. Such 2-KLG producing genera include the acidogenic, alpha-proteobacteria *Gluconobacter* and *Acetobacter,* the gamma-proteobacteria *Pseudomonas, Escherichia, Klebsiella, Serratia* and *Xanthmonas* and the Gram positive *Bacillus, Micrococcus* and *Pseudogluconobacter* (Imai, K. et al., U.S. Pat. No. 4,933,289 (1990), Sugisawa, H. et al., "Microbial production of 2-keto-L-gulonic acid from L-sorbose and D-sorbitol by *Gluconobacter melanogenus,*" *Agric. Biol. Chem.* 54:1201–1209 (1990), Yin, G. et al., U.S. Pat. No. 4,935,359 (1990), Shirafuji, et al., U.S. Pat. No. 4,876,195 (1989) and Nogami, I. et al., U.S. Pat. No. 5,474,924 (1995)).

To aid in increasing the yield of bacterial products, attempts have been made to exploit endogenous plasmids within microorganism strains. (Beppu, T. et al., U.S. Pat. No. 5,580,782 (1996), Fujiwara, A. et al., U.S. Pat. No. 5,399, 496 (1995); Tonouchi et al, U.S. Pat. No. 6,127,174 (2000), Hoshino, T. et at., U.S. Pat. No. 6,127,156 (2000)).

BRIEF SUMMARY OF THE INVENTION

One aspect of the present invention provides an isolated or purified nucleic acid molecule comprising a polynucleotide having a nucleotide sequence at least 95% identical to a nucleotide sequence of a *Ketogulonigenium* plasmid replicon found on the endogenous plasmid contained in NRRL Deposit No. B-21627 and at least one exogenous nucleotide sequence.

Further embodiments of the invention include an isolated or purified nucleic acid molecule comprising a polynucleotide having a nucleotide sequence at least 90% identical, and more preferably at least 95%, 97%, 98% or 99% identical, to any of the above nucleotide sequences, or a polynucleotide which hybridizes under stringent hybridization conditions to a polynucleotide having a nucleotide sequence as in the above. The polynucleotide which hybridizes does not hybridize under stringent hybridization conditions to a polynucleotide having a nucleotide sequence consisting of only A residues or of only T residues.

The present invention relates, in general, to a novel genus of bacteria known as *Ketogulonigenium.* The present invention further relates to *Ketogulonigenium* comprising a transgene (recombinant DNA), comprising an endogenous plasmid. The invention also relates to a method for transforming *Ketogulonigenium* comprising conjugative transfer of a vector from *E. coli* to *Ketogulonigenium,* and to a method for transforming *Ketogulonigenium* comprising electroporation.

The invention provides a nucleic acid molecule comprising a nucleotide sequence at least 95% identical to a *Ketogulonigenium* endogenous plasmid contained in NRRL Deposit No. B-21627. The invention also provides a nucleic acid molecule comprising a polynucleotide having a sequence at least 95% identical to a *Ketogulonigenium* replicon found on an endogenous plasmid contained in NRRL Deposit No. B-21627. The invention further provides a vector comprising a nucleic acid molecule comprising a nucleotide sequence of a *Ketogulonigenium* replicon found on an endogenous plasmid contained in NRRL Deposit No. B-21627.

Further advantages of the present invention will be clear from the description that follows.

BRIEF DESCRIPTION OF THE FIGURES

FIGS. 1A–1E show the nucleotide (SEQ ID NO:1) sequence of an endogenous plasmid, determined by sequencing of the endogenous plasmid (pADMX6L1), contained in NRRL Deposit No. B-21627. The nucleotide has a sequence of about 7029 nucleic acid residues.

FIGS. 2A–2C show the nucleotide (SEQ ID NO:2) sequence of an endogenous plasmid, determined by sequencing of the endogenous plasmid (pADMX6L2), contained in NRRL Deposit No. B-21627. The nucleotide has a sequence of about 4005 nucleic acid residues.

FIGS. 3A–3N show the nucleotide (SEQ ID NO:3) sequence of an endogenous plasmid, determined by sequencing of the endogenous plasmid (pADMX6L3), contained in NRRL Deposit No. B-21627. The nucleotide has a sequence of about 19,695 nucleic acid residues.

FIGS. 4A–4C show the nucleotide (SEQ ID NO:4) sequence of an endogenous plasmid, determined by sequencing of the endogenous plasmid (pADMX6L4), contained in NRRL Deposit No. B-21627. The nucleotide has a sequence of about 4211 nucleic acid residues.

FIGS. 5A–5B show the nucleotide (SEQ ID NO:5) sequence of the replicon on an endogenous plasmid (pADMX6L1), determined by homology of amino acid sequences encoded by the endogenous plasmid to known replication proteins, contained in NRRL Deposit No. B-21627. The nucleotide has a sequence of about 1456 nucleic acid residues.

FIGS. 6A–6B show the nucleotide (SEQ ID NO:6) sequence of the the replicon on an endogenous plasmid (pADMX6L2), determined by homology of amino acid sequences encoded by the endogenous plasmid to known replication proteins, contained in NRRL Deposit No. B-21627. The nucleotide has a sequence of about 2401 nucleic acid residues.

FIGS. 7A–7B show the nucleotide (SEQ ID NO:7) sequence of the the replicon on an endogenous plasmid (pADMX6L3), determined by homology of amino acid sequences encoded by the endogenous plasmid to known replication proteins, contained in NRRL Deposit No. B-21627. The nucleotide has a sequence of about 2029 nucleic acid residues.

FIG. 8 shows the amino acid sequence (SEQ ID NO:8) of a replication protein encoded by an endogenous plasmid (pADMX6L1) determined from the nucleotide sequence of pADMX6L1 contained in NRRL B-21627. The polypeptide has a sequence of about 151 amino acids in length.

FIG. 9 shows the amino acid sequence (SEQ ID NO:9) of a replication protein encoded by an endogenous plasmid (pADMX6L2) determined from the nucleotide sequence of pADMX6L2 contained in NRRL B-21627. The polypeptide has a sequence of about 466 amino acids in length.

FIG. 10 shows the amino acid sequence (SEQ ID NO:10) of a replication protein encoded by an endogenous plasmid (pADMX6L3) determined from the nucleotide sequence of pADMX6L3 contained in NRRL B-21627. The polypeptide has a sequence of about 342 amino acids in length.

DETAILED DESCRIPTION OF THE INVENTION

Unless otherwise indicated, all nucleotide sequences determined by sequencing a DNA molecule herein were determined using an automated DNA sequencer (such as the ABI Prism 3700). Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule.

Unless otherwise indicated, each "nucleotide sequence" set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U) where each thymidine deoxynucleotide (T) in the specified deoxynucleotide sequence in is replaced by the ribonucleotide uridine (U). For instance, reference to an RNA molecule having the sequence of SEQ ID NO:1 set forth using deoxyribonucleotide abbreviations is intended to indicate an RNA molecule having a sequence in which each deoxynucleotide A, G or C of SEQ ID NO:1 has been replaced by the corresponding ribonucleotide A, G or C, and each deoxynucleotide T has been replaced by a ribonucleotide U.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

In another aspect, the invention provides an isolated nucleic acid molecule comprising a polynucleotide which hybridizes under stringent hybridization conditions to a portion of the polynucleotide in a nucleic acid molecule of the invention described above, for instance, in the endogenous plasmids contained in NRRL Deposit No. B-21627. By "stringent hybridization conditions" is intended overnight incubation at 42° C. in a solution comprising: 50% formamide, 5×SSC (150 mM NaCl, 15 mM trisodium citrate), 50 mM sodium phosphate (pH7.6), 5× Denhardt's solution, 10% dextran sulfate, and 20 μg/ml denatured, sheared salmon sperm DNA, followed by washing the filters in 0.1×SSC at about 65° C. By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers.

Of course, polynucleotides hybridizing to a larger portion of the reference polynucleotide (e.g., the deposited endogenous plasmid), for instance, a portion 50–750 nt in length, or even to the entire length of the reference polynucleotide, also useful as probes according to the present invention, as are polynucleotides corresponding to most, if not all, of the nucleotide sequence of the deposited DNA or the nucleotide sequence as shown in FIG. 1 (SEQ ID NO:1). By a portion of a polynucleotide of "at least 20 nt in length," for example, is intended 20 or more contiguous nucleotides from the nucleotide sequence of the reference polynucleotide, (e.g., the deposited DNA or the nucleotide sequence as shown in FIG. 1 (SEQ ID NO:1)). As indicated, such portions are useful diagnostically either as a probe according to conventional DNA hybridization techniques or as primers for amplification of a target sequence by the polymerase chain reaction (PCR), as described, for instance, in Molecular Cloning, A Laboratory Manual, 2nd. edition, edited by Sambrook, J., Fritsch, E. F. and Maniatis, T., (1989), Cold Spring Harbor Laboratory Press, the entire disclosure of which is hereby incorporated herein by reference.

By a polynucleotide having a nucleotide sequence at least, for example, 95% "identical" to a reference nucleotide sequence is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence.

As a practical matter, whether any particular nucleic acid molecule is at least 90%, 95%, 97%, 98% or 99% identical to, for instance, the nucleotide sequence shown in FIG. 1 or to the nucleotide sequence of the deposited endogenous plasmid can be determined conventionally using known computer programs such as the FastA program. FastA does a Pearson and Lipman search for similarity between a query sequence and a group of sequences of the same type nucleic acid. Professor William Pearson of the University of Virginia Department of Biochemistry wrote the FASTA program family (FastA, TFastA, FastX, TFastX and SSearch). In collaboration with Dr. Pearson, the programs were modified and documented for distribution with GCG Version 6.1 by Mary Schultz and Irv Edelman, and for Versions 8 through 10 by Sue Olson.

The present invention provides *Ketogulonigenium,* comprising a transgene (recombinant DNA) comprising an endogenous *Ketogulonigenium* plasmid. Preferably, the endogenous *Ketogulonigenium* plasmid is contained in Deposit No. NRRL B-21627. As used herein, a transgene is defined as a transplanted nucleotide sequence which is exogenous, or non-native, to the host. An exogenous nucleotide sequence, as used in the current context, is a nucleotide sequence which is not found in Deposit No. NRRL B-21627. Thus, the term exogenous nucleotide sequence is meant to encompass a nucleotide sequence that is foreign to Deposit No. NRRL B-21627, as well as a nucleotide sequence endogenous, or native, to Deposit No. NRRL B-21627 that has been modified. Modification of the endogenous nucleotide sequence may include, for instance, mutation of the native nucleotide sequence or any of its regulatory elements. As used herein, mutation is defined as any change in the wild-type sequence of genomic or plasmid DNA. An additional form of modification may also include fusion of the endogenous nucleotide sequence to a nucleotide sequence that is normally not present, in relation to the endogenous nucleotide sequence. The transgene may be regulated by its normal promoter, or more commonly, by a promoter that normally regulates a different gene. The invention also provides a method for producing transformed *Ketogulonigenium,* comprising transforming *Ketogulonigenium* with a transgene, comprising, part or all of an endogenous *Ketogulonigenium* plasmid. Preferably, the endogenous *Ketogulonigenium* plasmid is contained in Deposit No. NRRL B-21627.

The term replicon as used herein is meant to encompass a DNA sequence comprising those genes and gene expression control elements such as promoters and terminators, other DNA sequence features such as short sequence repeats (iterons), origins of plasmid replication (ori or oriV sites), or other DNA sequence features that are required to support the autonomous replication of a circular DNA molecule in a bacterial host (Chapter 122, pp. 2295–2324, in *Escherichia coli and Salmonella: Cellular and Molecular Biology,* $2^{nd}$ Edition, Frederick C. Neidhardt, Ed., ASM Press (1996)). The requirements of a replicon can vary from as little as a short ori sequence in the case of plasmids that do not require their own replication proteins, to larger sequences containing one or more plasmid-borne replication genes.

The definition of a transformed cell, as used herein, is a cell where DNA has been inserted into a bacterial cell. The transformation of *Ketogulonigenium* may be transient or stable. Preferably, the invention provides a method for producing stably transformed *Ketogulonigenium.* As used herein, a stably transformed cell is a cell wherein a transgene is transmitted to every successive generation. A preferred embodiment of the present invention is that *Ketogulonigenium* is transformed via electroporation. An additional preferred embodiment of the present invention is that *Ketogulonigenium* is transformed by the process of conjugation, including, for instance, bi-parental and tri-parental conjugation. Conjugation, as used herein, is the process by which bacteria transfer DNA from a donor cell to a recipient cell through cell-to cell contact.

The present invention relates to a novel genus of bacteria, comprising the ADMX6L strain, designated as *Ketogulonigenium.* The present inventors have discovered novel strains of bacteria, not belonging to any known genera, that produce 2-keto-L-gulonic acid from sorbitol.

*Ketogulonigenium* (Ke.to.gu.lo.ni.gen'.i.um. M.L. n. acidum ketogulonicum ketogulonic acid; Gr. V. gennaio to produce; M.L. n. ketogulonigenium ketogulonic acid producing) is gram negative, facultatively anaerobic, motile or non-motile, has ovoid to rod-shaped cells, 0.8–1.3 μm long, 0.5–0.7 μm in diameter, with tapered ends, occurring as single cells, pairs and occasionally short chains. Some strains form elongated cells (up to 30 μm in length) on TSB. Flagella and fimbrae have been observed. Colonies are tan colored, smooth, circular, entire, raised to convex, 1–2 mm in diameter with a diffusable brown pigment after 48 hrs incubation. Oxidase and catalase reactions are positive. Optimum temperature range is 27 to 31° C., optimum pH range is 7.2 to 8.5 and optimum $Na^+$ concentration is 117–459 mM. Chemoorganotrophic. Carbon sources utilized include arabinose, cellobiose, fructose, glucose, glycerol, inositol, lactose, maltose, mannitol, mannose, rhamnose, sorbitol, sorbose, sucrose, trehalose, pyruvate and succinate. Favored carbon sources are inositol, mannitol, glycerol, sorbitol, lactose and arabinose. All strains examined produce 2-keto-L-gulonic acid from L-sorbose. Major cellular fatty acids are 16:0 and 18:1 ω7c/ω9t/ω12t and the mol % DNA G+C is 52.1 to 54.0 percent. Small subunit rDNA sequence analysis place this genus in the alpha subgroup of the Proteobacteria. All strains isolated in the present study group originated in soil. DNA reassociation studies divide the genus into two species. *K. vulgarae* and *K. robustum,* of which *K. vulgarae* is the designated type species. A group of bacteria having the above-mentioned properties does not belong to any known genera as described in Bergey's Manual of Systematic Bacteriology, and therefore belongs to a new genus.

Strain ADMX6L of *Ketogulonigenium* was isolated and deposited at the Agricultural Research Service Culture Collection (NRRL), 1815 North University Street, Peoria, Ill. 61604, USA, on Oct. 1, 1996, under the provisions of the Budapest Treaty, and assigned accession numbers NRRL B-21627.

The present invention provides a method for conjugative transfer of a vector from *E. coli* to *Ketogulonigenium* comprising culturing the *E. coli* with the *Ketogulonigenium* under such conditions such that the *E. coli* transfers the vector to the *Ketogulonigenium.* The method of conjugative transfer relies on the ability of the vector to replicate in both organisms, and thus requires that the vector contain replicons that are functional in both organisms. A replicon is a nucleotide sequence, typically several hundred to several thousand base pairs long, that is vital to plasmid DNA replication. Preferably, the method comprises using any vector that contains a replicon that is functional in *E. coli,* as well a replicon that is functional in *Ketogulonigenium.* More preferably, the method of the invention comprises the vectors pDELIA8 and pXH2/K5. Given that the preferred method comprises using any vector that contains a replicon that is functional in *E. coli,* as well as a replicon that is functional in *Ketogulonigenium,* it would also be possible to transfer a vector, via conjugation, from *Ketogulonigenium* to *E. coli.*

The present invention also provides a method for transforming *Ketogulonigenium* comprising inserting a vector into the *Ketogulonigenium* through the process of electroporation. Preferably, the vector used in electroporation of *Ketogulonigenium* is pMF1014-α.

The present invention provides isolated or purified nucleic acid molecules comprising the polynucleotides, or their complements, of endogenous plasmids that have been isolated and purified from a strain, NRRL Deposit No. B-21627 (ADMX6L), of this novel genus. Four endogenous plasmids have been isolated from strain NRRL Deposit No. B-21627. The nucleotide sequence shown in FIG. 1 (SEQ ID NO:1) is the nucleotide sequence of plasmid pADMX6L1 as determined by automated sequencing. The nucleotide sequence shown in FIG. 2 (SEQ ID NO:2) is the nucleotide sequence of plasmid pADMX6L2 as determined by automated sequencing. The nucleotide sequence shown in FIG. 3 (SEQ ID NO:3) is the nucleotide sequence of plasmid pADMX6L3 as determined by automated sequencing. The nucleotide sequence shown in FIG. 4 (SEQ ID NO:4) is the nucleotide sequence of plasmid pADMX6L4 as determined by automated sequencing.

The endogenous plasmids contained within NRRL B-21627 (ADMX6L) have been isolated and ligated into pUC19 or pJND1000. Specifically, plasmid pADMX6L1, corresponding to SEQ ID NO:1, and pJND1000 are digested with BamHI and ligated to each other using T4 ligase. The pXB1 plasmid construct was then introduced into *E. coli* DH5αMCR and the culture collection was deposited at the Agricultural Research Service Culture Collection (NRRL), 1815 North University Street, Peoria, Ill. 61604, USA, on Feb. 23, 2001, under the provisions of the Budapest Treaty, and assigned accession numbers NRRLB-30418. Plasmid pADMX6L2, corresponding to SEQ ID NO:2, and pUC19 were digested with HinDIII and ligated to one another using T4 ligase. The pXH2 plasmid construct was then introduced into *E. coli* DH5αMCR and the culture collection was deposited at the Agricultural Research Service Culture Collection (NRRL), 1815 North University Street, Peoria, Ill. 61604, USA, on Feb. 23, 2001, under the provisions of the Budapest Treaty, and assigned accession numbers NRRL B-30419. Plasmid pADMX6L4, corresponding to SEQ ID NO:4, and pUC19 are digested with SspI and SmaI, respectively, and ligated to one another using T4 ligase. The pXB4 plasmid construct was then introduced into *E. coli* DH5αMCR and the culture collection is deposited at the Agricultural Research Service Culture Collection (NRRL), 1815 North University Street, Peoria, Ill. 61604, USA, on Mar. 12, 2001, under the provisions of the Budapest Treaty, and assigned accession number NRRL B-30435.

Unless otherwise indicated, all nucleotide sequences determined by sequencing a DNA molecule herein were determined using an automated DNA sequencer (such as the ABI Prism 3700). Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art.

Unless otherwise indicated, each "nucleotide sequence" set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U) where each thymidine deoxynucleotide (T) in the specified deoxynucleotide sequence is replaced by the ribonucleotide uridine (U). For instance, reference to an RNA molecule having the sequence of SEQ ID NO:1 set forth using deoxyribonucleotide abbreviations is intended to indicate an RNA molecule having a sequence in which each deoxynucleotide A, G or C of SEQ ID NO:1 has been replaced by the corresponding ribonucleotide A, G or C, and each deoxynucleotide T has been replaced by a ribonucleotide U.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

One aspect of the invention provides an isolated or purified nucleic acid molecule comprising a polynucleotide having a nucleotide sequence selected from the group consisting of: (a) a nucleotide sequence in SEQ ID NO:1, SEQ ID NO:2, SEQ ID NO:3, SEQ ID NO:4, SEQ ID NO:5, SEQ ID NO:6, and SEQ ID NO:7; (b) a nucleotide sequence of a plasmid contained in NRRL Deposit No. B-30418, NRRL Deposit No. B-30419, and NRRL Deposit No. B-30435; and (c) a nucleotide sequence complementary to any of the nucleotide sequences in (a) or (b) above.

Further embodiments of the invention include isolated nucleic acid molecules that comprise a polynucleotide having a nucleotide sequence at least 90% identical, and more preferably at least 95%, 97%, 98% or 99% identical, to any of the *Ketogulonigenium* nucleotide sequences in (a), (b) or (c) above, or a polynucleotide which hybridizes under stringent hybridization conditions to a polynucleotide having a nucleotide sequence identical to the *Ketogulonigenium* portion of a nucleotide sequence in (a), (b) or (c), above. The polynucleotide which hybridizes does not hybridize under stringent hybridization conditions to a polynucleotide having a nucleotide sequence consisting of only A residues or of only T residues.

A polynucleotide having a nucleotide sequence at least, for example, 95% "identical" to a reference nucleotide sequence is intended to mean that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence.

Figure 5B:
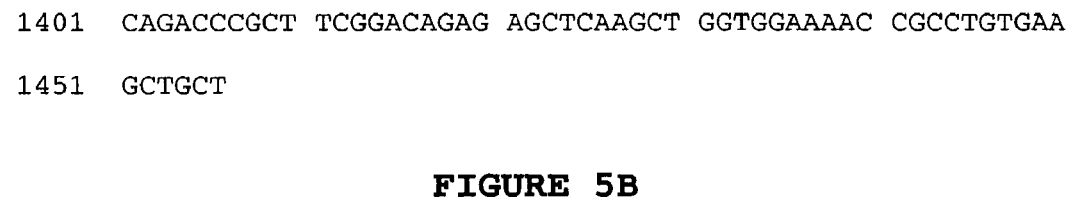

As a practical matter, whether any particular nucleic acid molecule is at least 90%, 95%, 97%, 98% or 99% identical to, for instance, the nucleotide sequences shown in FIG. 1, 2, 3, 4, 5, 6, or 7, or to the nucleotide sequences of the deposited plasmids can be determined conventionally using known computer programs such as the FastA program. FastA does a Pearson and Lipman search for similarity between a query sequence and a group of sequences of the same type nucleic acid. Professor William Pearson of the University of Virginia Department of Biochemistry wrote the FASTA program family (FastA, TFastA, FastX, TFastX and SSearch). In collaboration with Dr. Pearson, the programs were modified and documented for distribution with GCG Version 6.1 by Mary Schultz and Irv Edelman, and for Versions 8 through 10 by Sue Olson.

The present application is directed to nucleic acid molecules at least 95%, 97%, 98% or 99% identical to the nucleic acid sequences shown in FIG. 1 (SEQ ID NO:1), FIG. 2 (SEQ ID NO:2), FIG. 3 (SEQ ID NO:3), and FIG. 4 (SEQ ID NO:4); or to the *Ketogulonigenium* portion of the nucleic acid sequence of the deposited plasmids.

The present application is also directed to nucleic acid molecules at least 95%, 97%, 98% or 99% identical to the nucleic acid sequences shown in FIG. 5 (SEQ ID NO:5), FIG. 6 (SEQ ID NO:6), and FIG. 7 (SEQ ID NO:7).

One aspect of the invention provides an isolated nucleic acid molecule comprising a polynucleotide which hybridizes under stringent hybridization conditions to a portion of the polynucleotide of a nucleic acid molecule of the invention described above, for instance, in the plasmid contained in NRRL B-30418, NRRL B-30419, or NRRL B-30435, or in SEQ ID NO:1, SEQ ID NO:2, SEQ ID NO:3, SEQ ID NO:4, SEQ ID NO:5, SEQ ID NO:6, or SEQ ID NO:7. By "stringent hybridization conditions" is intended overnight incubation at 42° C. in a solution comprising: 50% formamide, 5×SSC (150 mM NaCl, 15 mM trisodium citrate), 50 mM sodium phosphate (pH7.6), 5× Denhardt's solution, 10% dextran sulfate, and 20 μg/ml denatured, sheared salmon sperm DNA, followed by washing the filters in 0.1×SSC at about 65° C. By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers.

Of course, polynucleotides hybridizing to a larger portion of the reference polynucleotides (e.g., the deposited endogenous plasmids), for instance, a portion 15–750 nt in length, or even to the entire length of the reference polynucleotide, are also useful as probes according to the present invention, as are polynucleotides corresponding to most, if not all, of the *Ketogulonigenium* portion of the nucleotide sequence of the deposited DNA or the nucleotide sequence as shown in FIGS. 1 (SEQ ID NO:1), 2 (SEQ ID:NO:2), 3 (SEQ ID NO:3), 4 (SEQ ID NO:4), 5 (SEQ ID NO:5), 6 (SEQ ID NO:6), and 7 (SEQ ID NO:7). A portion of a polynucleotide of, at least 15 nt in length, for example, is intended to mean 15 or more contiguous nucleotides from the nucleotide sequence of the reference polynucleotide, (e.g., the deposited DNA or the nucleotide sequences as shown in FIGS. 1 (SEQ ID NO:1), 2 (SEQ ID:NO:2), 3 (SEQ ID NO:3), 4 (SEQ ID NO:4), 5 (SEQ ID NO:5), 6 (SEQ ID NO:6), 7 (SEQ ID NO:7)). As indicated, such portions are useful diagnostically either as a probe according to conventional DNA hybridization techniques or as primers for amplification of a target sequence by the polymerase chain reaction (PCR), as described, for instance, in *Molecular Cloning, A Laboratory Manual,* 2nd. edition, edited by Sambrook, J., Fritsch, E. F. and Maniatis, T., (1989), Cold Spring Harbor Laboratory Press, the entire disclosure of which is hereby incorporated herein by reference.

One embodiment of the present invention is a vector comprising the nucleic acid molecules contained in the group consisting of SEQ ID NO:1, SEQ ID NO:2, SEQ ID NO:3 and SEQ ID NO:4, corresponding to endogenous plasmids contained in Deposit No. NRRL B-21627 (ADMX6L). A preferred embodiment of the present invention is that polynucleotides of interest can be joined to the nucleic acid molecules of the present invention, which may contain a selectable marker. An additional preferred embodiment is that the vectors comprising the nucleic acid molecules also contain a transcription terminator, a promoter and a polylinker site. As used herein, a polylinker site is defined to be a discrete series of restriction endonuclease sites that occur between the promoter and the terminator. The vector can optionally contain its native expression vector and/or expression vectors which include chromosomal-, and episomal-derived vectors, e.g., vectors derived from bacterial exogenous plasmids, bacteriophage, and vectors derived from combinations thereof, such as cosmids and phagemids.

A DNA insert of interest should be operatively linked to an appropriate promoter, such as its native promoter or a host-derived promoter, the phage lambda $P_L$ promoter, the phage lambda $P_R$ promoter, the *E. coli* lac promoters, such as the lacI and lacZ promoters, trp and tac promoters, the T3 and T7 promoters and the gpt promoter to name a few. Other suitable promoters will be known to the skilled artisan.

The expression constructs will preferably contain sites for transcription initiation, termination and, in the transcribed region, a ribosome binding site for translation. The coding portion of the mature transcripts expressed by the constructs can include a translation initiating codon at the beginning and a termination codon appropriately positioned at the end of the coding sequence to be translated.

As indicated, the expression vectors will preferably include at least one marker capable of being selected or screened for. Preferably the selectable marker comprises a nucleotide sequence which confers antibiotic resistance in a host cell population. Such markers include amikacin, ampicillin, chloramphenicol, erythromycin, gentamicin, kanamycin, penicillin, spectinomycin, streptomycin, or tetracycline resistance genes. Other suitable markers will be readily apparent to the skilled artisan.

The translated polypeptide encoded by the DNA in the vector may be expressed in a modified form, such as a fusion protein, and may include not only secretion signals, but also additional heterologous functional regions. Thus, for instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification.

The translated protein encoded by the DNA contained in the vector can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

The present invention also provides vectors comprising nucleic acid molecules comprising a nucleotide sequence of a replicon found on an endogenous plasmid contained in Deposit No. NRRL B-21627. Preferably, the vector of the present invention comprises a replicon selected from the group of nucleotide sequences comprising SEQ ID NO:5, SEQ ID NO:6 and SEQ ID NO:7. The replicon is a nucleotide sequence that is typically several hundred to several thousand base pairs long and encodes functions controlling the replication of plasmid DNA. The nucleotide sequence in FIG. 5 (SEQ ID NO:5) is the nucleotide sequence comprising a replicon on plasmid pADMX6L1. The nucleotide sequence in FIG. 6 (SEQ ID NO:6) is the nucleotide sequence comprising a replicon on plasmid pADMX6L2. The nucleotide sequence in FIG. 7 (SEQ ID NO:7) is the nucleotide sequence comprising a replicon on plasmid pADMX6L3.

The present invention further provides a vector which has an replicon that is functional in *Escherichia coli* (*E. coli*) as well as a replicon that is functional in *Ketogulonigenium.* The present invention also provides a vector which has a replicon that is functional in *Ketogulonigenium,* as well as a replicon that is functional in any of the genera comprising the group consisting of *Acetobacter, Corynebacterium, Rhodobacter, Paracoccus, Roseobacter, Pseudomonas, Pseudogluconobacter, Gluconobacter, Serratia, Mycobacterium, Streptomyces* and *Bacillus*. Utilizing the fact that the vector comprises a functional replicon in *Ketogulonigenium,* and preferably also comprises a replicon functional in *E. coli,* the present invention provides for a transformed cell of the genus *Ketogulonigenium,* comprising the vector. The present invention also provides for a transformed *E. coli,* comprising the vector. *E. coli* is known to be an efficient host for amplification of a vector DNA and manipulation of recombinant DNA by simple and rapid methods. On the other hand, *Ketogulonigenium* can be used as a host for expression of *Ketogulonigenium* genes. Since the vectors of the present invention are such functional constructs, they enable cloning of certain genes of *Ketogulonigenium* in *E. coli* and thereafter the effective expression of the genes in *Ketogulonigenium.* Furthermore, it is favorable that such functional constructs also contain a DNA region necessary for conjugal transfer (mob site). Hence the vectors of the present invention can first be assembled in *E. coli* and then directly introduced into *Ketogulonigenium* by conjugal mating without isolation of plasmid DNA from *E. coli.*

The present invention further relates to (a) nucleic acid sequences comprising at least 95% functional homology with those encoding polypeptides derived from the four endogenous plasmids from *Ketogulonigenium* strain ADMX6L, and (b) to amino acid sequences comprising at least 95% functional homology with those encoded within the plasmids. The invention also relates to nucleic acid sequences comprising at least 95% functional homology with, pADMX6L1 rep ORF (bases 2255–2710 of FIG. 1 (SEQ ID NO:1), pADMX6L2 rep ORF (reverse compliment of bases 3960–2562 of FIG. 2 (SEQ ID NO:2), and pADMX6L3 rep ORF (reverse compliment of bases 5031–4003 of FIG. 3 (SEQ ID NO:3)). The invention further relates to amino acid sequences comprising at least 95% functional homology with those set forth in FIG. 8, 9 or 10.

Methods used and described herein are well known in the art and are more particularly described, for example, in R. F. Schleif and P. C. Wensink, *Practical Methods in Molecular Biology,* Springer-Verlag (1981); J. H. Miller, *Experiments in Molecular Genetics,* Cold Spring Harbor Laboratory Press, Cold Spring Harbor, N.Y. (1972); J. H. Miller, *A Short Course in Bacterial Genetics,* Cold Spring Harbor Laboratory Press, Cold Spring Harbor, N.Y. (1992); M. Singer and P. Berg, *Genes & Genomes,* University Science Books, Mill Valley, Calif. (1991); J. Sambrook, E. F. Fritsch and T. Maniatis, *Molecular Cloning: A Laboratory Manual,* 2d ed., Cold Spring Harbor Laboratory Press, Cold Spring Harbor, N.Y. (1989); P. B. Kaufman et al., *Handbook of Molecular and Cellular Methods in Biology and Medicine,* CRC Press, Boca Raton, Fla. (1995); *Methods in Plant Molecular Biology and Biotechnology,* B. R. Glick and J. E. Thompson, eds., CRC Press, Boca Raton, Fla. (1993); P. F. Smith-Keary, *Molecular Genetics of Escherichia coli,* The Guilford Press, New York, N.Y. (1989); *Plasmids: A Practical Approach,* 2nd Edition, Hardy, K. D., ed., Oxford University Press, New York, N.Y. (1993); *Vectors: Essential Data,* Gacesa, P., and Ramji, D. P., eds., John Wiley & Sons Pub., New York, N.Y. (1994); *Guide to Electroporation and electrofusions,* Chang, D., et al., eds., Academic Press, San Diego, Calif. (1992); *Promiscuous Plasmids of Gram-Negative Bacteria,* Thomas, C. M., ed., Academic Press, London (1989); *The Biology of Plasmids,* Summers, D. K., Blackwell Science, Cambridge, Mass. (1996); *Understanding DNA and Gene Cloning: A Guide for the Curious,* Drlica, K., ed., John Wiley and Sons Pub., New York, N.Y. (1997); *Vectors: A Survey of Molecular Cloning Vectors and Their Uses,* Rodriguez, R. L., et al., eds., Butterworth, Boston, Mass. (1988); *Bacterial Conjugation,* Clewell, D. B., ed., Plenum Press, New York, N.Y. (1993); Del Solar, G., et al., "Replication and control of circular bacterial plasmids," *Microbiol. Mol. Biol. Rev.* 62:434–464 (1998); Meijer, W. J., et al., "Rolling-circle plasmids from *Bacillus subtilis:* complete nucleotide sequences and analyses of genes of pTA1015, pTA1040, pTA1050 and pTA1060, and comparisons with related plasmids from gram-positive bacteria," *FEMS Microbiol. Rev.* 21:337–368 (1998); Khan, S. A., "Rolling-circle replication of bacterial plasmids," *Microbiol. Mol. Biol. Rev.* 61:442–455 (1997); Baker, R. L., "Protein expression using ubiquitin fusion and cleavage," *Curr. Opin. Biotechnol.* 7:541–546 (1996); Makrides, S. C., "Strategies for achieving high-level expression of genes in *Escherichia coli,*" *Microbiol. Rev.* 60:512–538 (1996); Alonso, J. C., et al., "Site-specific recombination in gram-positive theta-replicating plasmids," *FEMS Microbiol. Lett.* 142:1–10 (1996); Miroux, B., et al., "Over-production of protein in *Escherichia coli:* mutant hosts that allow synthesis of some membrane protein and globular protein at high levels," *J. Mol. Biol.* 260:289–298 (1996); Kurland, C. G., and Dong, H., "Bacterial growth inhibited by overproduction of protein," *Mol. Microbiol.* 21:1–4 (1996); Saki, H., and Komano, T., "DNA replication of IncQ broad-host-range plasmids in gram-negative bacteria," *Biosci. Biotechnol. Biochem.* 60:377–382 (1996); Deb, J. K., and Nath, N., "Plasmids of corynebacteria," *FEMS Microbiol. Lett.* 175:11–20 (1999); Smith, G. P., "Filamentous phages as cloning vectors," *Biotechnol.* 10:61–83 (1988); Espinosa, M., et al., "Plasmid rolling cicle replication and its control," *FEMS Microbiol. Lett.* 130:111–120 (1995); Lanka, E., and Wilkins, B. M., "DNA processing reaction in bacterial conjugation," *Ann. Rev. Biochem.* 64:141–169 (!995); Dreiseikelmann, B., "Translocation of DNA across bacterial membranes," *Microbiol. Rev.* 58:293–316 (1994); Nordstrom, K., and Wagner, E. G., "Kinetic aspects of control of plasmid replication by antisense RNA," *Trends Biochem. Sci.* 19:294–300 (1994); Frost, L. S., et al., "Analysis of the sequence gene products of the transfer region of the F sex factor," *Microbiol. Rev.* 58:162–210 (1994); Drury, L., "Transformation of bacteria by electroporation," *Methods*

*Mol. Biol.* 58:249–256 (1996); Dower, W. J., "Electroporation of bacteria: a general approach to genetic transformation," *Genet. Eng.* 12:275–295 (1990); Na, S., et al., "The factors affecting transformation efficiency of coryneform bacteria by electroporation," *Chin. J. Biotechnol.* 11:193–198 (1995); Pansegrau, W., "Covalent association of the traI gene product of plasmid RP4 with the 5'-terminal nucleotide at the relaxation nick site," *J. Biol. Chem.* 265: 10637–10644 (1990); and Bailey, J. E., "Host-vector interactions in *Escherichia coli*," *Adv. Biochem. Eng. Biotechnol.* 48:29–52 (1993).

EXAMPLES

The following examples are illustrative only and are not intended to limit the scope of the invention as defined by the appended claims.

Example 1

Preparation of Plasmid DNA from *Ketogulonigenium* and *E. coli* Strains

A portion of a frozen culture of *Ketogulonigenium robustum* ADMX6L (NRRL B-12627) was seeded into 10 ml X6L medium (2% mannitol, 1% yeast extract, 1% soytone, 0.5% malt extract, 0.5% NaCl, 0.25% $K_2HPO_4$, pH 7.8) and grown overnight at 30° C. A portion of a frozen culture of *Escherichia coli* transformed with pJND1000 was seeded into 10 ml of Luria Broth (1% tryptone, 0.5% yeast extract, 0.5% NaCl) and grown overnight at 37° C. Both cultures were used to prepare plasmid DNA.

DNA was isolated using the Promega Wizard Plus Midipreps DNA Purification System (Madison, Wis.). The culture was centrifuged at 10,000×g for 10 minutes at 4° C. in a Sorval RC-5B centrifuge using the SS-34 rotor. The pellet was suspend in 3 ml of 50 mM Tris-HCl, pH 7.5, 10 mM EDTA, 100 μg/ml RnaseA. Three ml of cell lysis solution (0.2M NaOH, 1% SDS) was added and mixed by inverting the tube, then three ml of neutralization solution (1.32M potassium acetate, pH4.8) was added and mixed by inverting the tube. The lysate was centrifuged at 14,000×g for 15 minutes at 4° C. in a SS-34 rotor, then the supernatant was carefully decanted to a new centrifuge tube. Ten ml of resuspension resin (40% isopropanol, 4.2M guanidine hydrochloride) was added to the supernatant fluid and mixed by swirling, then the mixture was transferred into the Promega Wizard Midicolumn, which was connected a vacuum manifold. Vacuum was applied to pull the resin/DNA mixture completely into the midicolumn. The column was washed twice with 15 ml of column wash solution (95% ethanol, 80 mM potassium acetate, 8.3 mM Tris-HCl, pH 7.5, 40 μM EDTA. The reservoir was removed from the midicolumn with a scissors, then the column was placed in a microcentrifuge tube and centrifuged at 10,000×g for 2 minutes to remove any residual solution. The midicolumn was transferred to a new microcentrifuge tube and 300 μl of sterile $dH_2O$ was applied. The tube was microcentrifuged at 10,000×g for 20 seconds to elute to the DNA into solution. A similar procedure would be employed for other plasmids from *Ketogulonigenium* or *E. coli,* except that choice and concentration of selective antibiotics would be altered as suitable for the plasmid being isolated.

Example 2

Transformation of a *Ketogulonigenium* Host with a Plasmid Using Electroporation

*Ketoguonigenium robustum* strain ADMX6L (NRRL B-21627) was transformed with plasmid pMF1014-α using the electroporation method. Plasmid pMF1014-α was described in a Ph.D. thesis at MIT (M. T. Follettie, "DNA Technology for *Corynebacterium glutamicum:* Isolation and Characterization of Amino Acid Biosynthetic Genes," Ph.D. Dissertation, Massachusetts Institute of Technology, Cambridge, Mass. (1989)). pMFW1014α encodes kanamycin resistance and can replicate and be maintained in both *E. coli* and in *Ketogulonigenium.*

Competent *Ketogulonigenium* cells were prepared by seeding a single colony of ADMX6L into 10 ml of X6L medium (1% soytone, 1% yeast extract, 0.5% malt extract, 0.5% NaCl, 0.25% $K_2HPO_4$, 2% mannitol, pH 7.8). The culture was shaken at 300 rpm at 30 C until reaching an optical density of 0.8 units at 600 nm wavelength. Five ml of this culture was used to seed 500 ml of fresh X6L medium in a 2 L baffled erlenmeyer flask, which was shaken at 300 rpm at 30° C. until reaching an optical density of 0.8 units. The culture was chilled in an ice-water bath 10 minutes, then transferred to a pre-chilled centrifuge bottle and centrifuged at 5,000 rpm in a Sorvall 5C-RB Refrigerated Centrifuge for 15 minutes at 4° C. Cells were maintained at 2–4° C. for all steps to follow. The supernatent was decanted and the cell pellet suspended in 5 ml ice-cold Milli-Q water, then additional cold Milli-Q water was was added to a volume of 500 ml. The cells were centrifuged as before, then rewashed in 500 ml of Milli-Q water as before and recentrifuged. The twice-washed cell pellet was suspended in 40 ml of ice-cold 10% glycerol then centrifuged again as before. The supernatent was decanted, then the cells were suspended in a volume of chilled 10% glycerol approximately equal to the volume of the cell pellet. The competent *Ketogulonigenium* cells were aliquoted to microcentrifuge tubes (40 μl per tube) and stored at −80° C.

A BioRad "Gene Pulser II" electroporator device was set to 1.5 kV, 25 uF. The pulse controller was set to 200 Ohms. One μl of pMF1014-α DNA prepared as in Example 1 was added to 40 μl of thawed chilled competent *Ketogulonigenium* cells on ice. The cell-DNA mixture was transferred to a pre-chilled electroporation cuvette, which was then transferred to the electroporation device and the pulse was applied. One ml of X6L medium was added to the cuvette, then the mixture was removed, transferred to a 10-ml test tube, and incubated for 2 hours with orbital shaking at 300 rpm and 30° C. The incubated cells (approximately 1.4 ml) were placed in a microcentrifuge tube and spun at 13,000 rpm for 2 minutes, after which 0.9 ml of clear supernatent was carefully removed. The cell pellet was suspended in the remaining supernatent, then the cells were spread onto the surface of an X6L medium agar plate (1.2% Difco Bacto Agar) containing 50 μg/ml of kanamycin, and the plate was incubated for 2–3 days at 30° C. Colonies that formed on this plate were *Ketogulonigenium* transformed with plasmid vector pMF1014-α.

Example 3

Transfer of Plasmids from *E. coli* to *Ketogulonigenium,* Deposit No. NRRL B-21627 by Bi-parental or Tri-parental Mating (A) Bi-parental Mating Plasmid pDELIA8 was transferred into *Ketogulonigenium* from *E. coli* by conjugation. To make pDELIA8, the AflIII-SphI fragment from plasmid pFD288 (GenBank Accession No. U30830), which contains the cloned mob region of plasmid RK2 (GenBank Accession No. L27758), was isolated from agarose gels and ligated to the large AflIII-SphI fragment from plasmid pUC19 (GenBank Accession No. M77789) to make the intermediate plasmid pUC19/oriT. pUC19/oriT DNA was digested with SspI and DraI and the large (2527 bp) fragment was purified from an agarose gel. Plasmid pMF1014-α (M. T. Follettie, "DNA Technology for *Corynebacterium glutamicum:* Isolation and Characterization of Amino Acid Biosynthetic Genes", Ph.D. Dissertation, Massachusetts Institute of Technology, Cambridge, Mass. (1989)) was digested with BamHI and PstI, made blunt ended with Klenow fragment, and the large fragment was isolated from an agarose gel. The gel purified, blunt-ended fragments from pUC19/oriT and pMF1014-α were ligated together to make pDELIA8. pDELIA8 carries a gene for kanamycin resistance, a plasmid replication gene, the replicon that is functional in *E. coli* and in *Ketogulonigenium,* lacZα and a polylinker.

A 5 ml culture of *E. coli* S17-1 (ATCC 47055) was transformed with pDELIA8 using calcium chloride mediated transformation. The S17-7/pDELIA8 strain was grown in Luria Broth containing 50 μg/ml kanamycin at 37° C. overnight. *Ketogulonigenium robustum* strain ADMX6L01 was grown in X6L medium containing 50 μg/ml of nalidixic acid at 30° C. overnight. ADMX6L01 is a nalidixic acid resistant mutant of strain ADMX6L, derived by conventional mutagenesis of ADMX6L followed by selection of strains showing resistance to 50 μg/ml of nalidixic acid.

Fifty microliters of the fresh S17-1/pDELIA8 culture was transferred into 3 ml of Luria Broth containing 50 μg/ml of kanamycin and 5 μg/ml of tetracycline and grown at 37° C. until reaching an $OD_{600}$ of 0.2 to 0.4 absorption units at 600 nm. Two hundred microliters of the fresh ADMX6L01 culture was transferred into 3 ml of X6L medium containing nalidixic acid and grown at 30° C. until reaching an $OD_{600}$ of 0.8 absorption units. 400 μl of S17-1/pDELIA8 culture was placed in a 1.5 ml microcentrifuge tube and microcentrifuged for 2 minutes. The pellet was resuspended in X6L medium without antibiotics and spun down again. This pellet was resuspended in 1 ml of the fresh ADMX6L01 culture to achieve a suspension of mixed cells. The mixed cells were centrifuged to a pellet, resuspended in 1 ml of fresh X6L medium without antibiotics, then pelleted and washed once again in 1 ml of X6L medium. The final pellet of mixed cells was then resuspended in 100 μl of X6L medium without antibiotics and spotted onto a a sterilized GN-6 metrical 0.45 μm×25 mm filter (Gelman Sciences, Product No. 63068) resting on the surface of an X6L agar medium plate without antibiotics, which was then incubated overnight at 30° C. The cell biomass on the filter was resuspended in 3 ml of X6L medium and 50 μl of this suspension was plated onto X6L agar medium containing kanamycin and nalidixic acid at concentration 50 μg/ml each. Colonies that formed on this plate after 2–3 days incubation at 30° C. were *Ketogulonigenium transconjugants* transformed with pDELIA8.

(B) Tri-Parental Mating

A 5 ml culture of *E. coli* HB101 (ATCC33694) harboring plasmid pDELIA8 was grown in Luria Broth (LB) containing 50 μg/ml of kanamycin at 37 degrees overnight. A 5 ml culture of *E. coli* HB101 harboring plasmid RP1 (GenBank Accession No. L27758) was grown in Luria Broth containing 5 μg/ml of tetracycline at 37 degrees overnight. A 5 ml culture of *Ketogulonigenium robustum* ADMX6L01 was grown in X6L medium containing 50 μg/ml of nalidixic acid at 30 degrees overnight. Fifty microliters each of the fresh *E. coli* HB101/pDELIA8 and HB101/RP1 cultures were transferred to 3 ml of LB with 50 μg/ml of kanamycin or 5 μg/ml of tetracycline, respectively, and were grown to an $OD_{600\ nm}$ of 0.2 to 0.4. Two hundred microliters of the fresh *Ketogulonigenium robustum* ADMX6L01 culture was transferred to 3 ml of X6L medium containing 50 μg/ml of nalidixic acid and grown to an $OD_{600\ nm}$ of 0.8. Four hundred microliters each of the *E. coli* cultures was combined and pelleted in a 1.5 ml microfuge tube, then decanted, resuspended in 1 ml of X6L medium without antibiotics and spun down again. The supernatant was removed and the *E. coli* pellet was resuspended in 1 ml of the fresh ADMX6L01 culture. The three-strain mixture was centrifuged to a pellet, then resuspended again 1 ml of X6L medium without antibiotics and recentrifuged. The pellet from this wash was resuspended in 100 μl of X6L medium without antibiotics and spotted onto a sterilized GN-6 metrical 0.45 μm×25 mm filter (Gelman Sciences, Product No. 63068) resting on the surface of an X6L agar medium plate without antibiotics, which was then incubated overnight at 30° C. The cell biomass on the filter was resuspended in 3 ml of X6L medium and 50 μl of this suspension was plated onto X6L agar medium containing kanamycin and nalidixic acid at concentration 50 μg/ml each. Colonies that formed on this plate after 2–3 days incubation at 30° C. were *Ketogulonigenium* transconjugants transformed with plasmid pDELIA8.

Example 4

Construction of Plasmid Vector pJND1000 pJND1000 was constructed from segments of plasmids pUC19 (GenBank Accession No. M77789), pUC4K (GenBank Accession No. X06404), pFD288 (GenBank Accession No. U30830), and pFC5 (David M. Lonsdale et. al., "pFC1 to pFC7: A novel family of combinatorial cloning vectors.", *Plant Molecular Biology Reporter* 13(4):343–345 (1995)).

The ampicillin resistance gene ($amp^R$) was removed from pUC19 by digesting pUC19 DNA with restriction enzymes DraI and SspI, separating the 1748 bp vector fragment from the smaller $amp^R$ fragment and other fragments by gel electrophoresis, then recovering the 1748 bp fragment from a gel slice. A kanamycin resistance gene ($kan^R$) fragment from pUC4K was prepared by digesting pUC4K with restriction enzyme PstI, treating the mixture with Klenow Fragment to produce blunt ends, separating the fragments by gel electrophoresis, then purifying the 1240 bp $kan^R$ fragment from a gel slice. The isolated fragments from pUC19 and pUC4K were mixed and ligated with T4 ligase following the protocol of GibcoBRL technical bulletin 15244-2 (Rockville, Md.) to produce "intermediate p1", an intermediate plasmid carrying pUC19 features and a $kan^R$ gene.

Strain *E. coli* DH5αMCR was transformed with the ligation mixture following an established protocol ("Fresh Competent *E. coli* prepared using $CaCl_2$", pp. 1.82–1.84, in J. Sambrook, E. F. Fritsch and T. Maniatis, *Molecular Cloning: A Laboratory Manual,* 2nd Ed. (1989)). Transformants were selected on Luria Broth plates containing 50 μg/ml of kanamycin.

An oriT site for conjugative transfer was obtained from plasmid pFD288 by restricting it with HaeII, converting the single stranded ends to blunt ends by treating the mixture with Klenow Fragment, separating the fragments by agarose gel electrophoresis, then purifying the 778 bp oriT fragment from a gel slice. The intermediate p1 plasmid was opened at a single site with restriction enzyme SapI, then treated with Klenow Fragment to convert the single stranded ends to blunt ends. The SapI digested, blunt ended p1 intermediate was mixed with the purified oriT fragment, then treated with T4 ligase as above to create "intermediate p2", a plasmid which carries oriT in addition to $kan^R$ and other pUC19-derived features. Strain *E. coli* DH5αMCR was transformed with the ligation mixture as above. Intermediate p2 was confirmed by restriction digestion analysis.

The polylinker in intermediate plasmid p2 was replaced with the polylinker from pFC5. To do this the two plasmids were separately restricted with PvuII, the fragments from each digestion reaction were separated by gel electrophoresis, then the pFC5-derived polylinker fragment (531 bp), and the larger non-polylinker fragment from intermediate p2 were purified from gel slices. The recovered p2 fragment and the pFC5-derived polylinker fragment were mixed and joined using T4 ligase as above to make plasmid pJND1000. The structure of pJND1000 was confirmed by restriction digestion analysis. PJND1000 replicates in *E. coli,* has a functioning kanamycin resistance gene, an RK2-derived oriT site to permit conjugative transfer into *Ketogulonigenium* and other hosts, a polylinker for DNA cloning, forward and reverse M13 primers to facilitate DNA sequencing reactions into the polylinker, and permits screening for cloned inserts by inactivation of lacZα using Xgal indicator plates.

Example 5

Isolation of Plasmid pXB1 Containing Linearized *Ketogulonigenium* Plasmid pADMX6L1

The DNA sequence of plasmid pADMX6L1 (SEQ ID NO: 1) is about 7029 bp long and contains a single BamHI restriction site. The BamHI site was utilized to clone the pADMX6L1 sequence into the *E. coli* vector pJND1000. A DNA prep containing a mixture of the endogenous plasmids from *Ketogulonigenium robustum* ADMX6L, and purified pJND1000 DNA from *E. coli,* were made as in Example A and separately digested with restriction enzyme BamHI. A Wizard DNA Clean-Up kit was used to separate the digested DNA from enzyme and salts in preparation for the next step, with a final DNA suspension volume of 50 μl. DNA from the two digestions (3 μl of pJND1000 DNA and 10 μl of *Ketogulonigenium* plasmid DNA) was mixed and ligated overnight at room temperature using T4 ligase with the protocol of GibcoBRL technical bulletin 15244-2 (Rockville, Md.). Strain *E. coli* DH5αMCR was transformed with the ligation mixture following an established protocol ("Fresh Competent *E. coli* prepared using $CaCl_2$", pp. 1.82–1.84, in J. Sambrook, E. F. Fritsch and T. Maniatis, *Molecular Cloning: A Laboratory Manual,* 2nd Ed. (1989)). Transformants were spread on Luria Broth agar plates containing 50 μg/ml of kanamycin and 40 μg/ml of Xgal and grown at 37 deg C. Colonies that were white, indicating insertion of DNA into the pJND1000 BamHI site, were picked and cultured for further processing. Digestion of plasmid DNA from transformants using BamHI, EcoRV, and XhoI separately, yielded the expected fragment sizes for sucessful cloining of pADMX6L1 into the pJND1000 *E. coli* vector. The identity of the pADMX6L1 insert was further confirmed by partial DNA sequencing into the pADMX6L1 DNA region using the M13 sequencing primer regions of the pJND1000 vector. The chimeric plasmid containing linearized pADMX6L1 cloned into pJND1000 was named pXB1. An *E. coli* host transformed with pXB1 was deposited in the patent collection of the National Regional Research Laboratories in Peoria, Ill., U.S.A. under the terms of the Budapest Treaty as NRRL B-30418.

Example 6

Isolation of Plasmid pXH2 Containing Linearized *Ketogulonigenium* Plasmid pADMX6L2

The DNA sequence of plasmid pADMX6L2 (SEQ ID NO: 2) is about 4005 bp long and contains a single HinDIII restriction site. The HinDIII site was utilized to clone the pADMX6L2 sequence into the *E. coli* vector pUC19. The procedure was the same as in Example 5, except that prior to the ligation step the plasmid DNAs were digested with HinDIII instead of with BamHI, and transformants were plated on LB agar plates containing Xgal and 100 μg/ml of ampicillin instead of the kanamycin. Plasmid DNA from transformants giving white colonies was isolated and digested with HinDIII and NdeI, giving the expected fragment sizes for correct insertion of linearized pADMX6L2 DNA into the pUC19 vector. The identity of the pADMX6L2 insert was further confirmed by partial DNA sequencing into the pADMX6L2 region using the M13 primer regions of pUC19. The chimeric plasmid containing linearized pADMX6L2 cloned into pUC19 was named pXH2. An *E. coli* host transformed with pXH2 was deposited in the patent collection of the National Regional Research Laboratories in Peoria, Ill., U.S.A. under the terms of the Budapest Treaty as NRRL B-30419.

Example 7

Construction of *E. coli/Ketogulonigenium* Shuttle Plasmid pXH2/K5

Since kanamycin resistance can be expressed in *Ketogulonigenium,* it was desireable to replace the ampR resistance gene in pXH2 with a kanamycin resistance gene, thereby allowing the selective isolation of *Ketogulonigenium* strains transformed with a plasmid. In vitro transposition was used to move a kanamycin resistance gene into pXH2 and simultaneously inactivate ampicillin resistance. Insertion of a kanamycin resistance gene into the ampicillin resistance gene of pXH2 was achieved using Epicentre technologies EZ::TN Insertion System (Madison, Wis.). 0.05 pmoles of pXH2 was combined with 0.05 pmoles of the <KAN-1> Transposon, 1 μl of EZ::TN 10×Reaction Buffer, 1 μl of EZ::TN Transposase, and 4 ul of sterile water giving a total volume of 10 μl in the transposition reaction. This mixture was incubated at 37° C. for 2 hours, then stopped by adding 1 μl of EZ::TN 10×Stop Solution, mixing, and incubation at 70° C. in a heat block for 10 minutes. *E. coli* DH5αMCR was transformed with the DNA mixture and transformants were selected on Luria Broth agar plates containing 50 μg/ml of kanamycin. Colonies recovered from these plates were patched onto two LB agar plates, one with 50 μg/ml of kanamycin and the other with 100 μg/ml of ampicillin. Only those that grew on the kanamycin plates were saved. Plasmid DNA from an ampicillin sensitive, kanamycin resistant colony was isolated as "pXH2/K5". The proper insertion of the kanamycin resistance transposon into the vector ampicillin resistance gene was confirmed by analyzing pXH2/K2 DNA with various restriction endonucleases. To demonstrate the viability of pXH2/K5 as an *E. coli/Ketogulonigenium* shuttle vector, *Ketogulonigenium robustum* strain ADMX6L was transformed with pXH2/K5 DNA using the electroporation technique of Example 2. Stable, kanamycin resistant transformants were obtained from which pXH2/K5 DNA can be reisolated.

Example 8

Isolation of Plasmid pXB4 Containing Linearized *Ketogulonigenium* Plasmid pADMX6L4

The DNA sequence of plasmid pADMX6L4 (SEQ ID NO: 4) is about 4211 bp long and contains a single SspI restriction site. The SspI site was utilized to clone the pADMX6L4 plasmid into the *E. coli* vector pUC19. The procedure was the same as in Example 6, except that prior to the ligation step the plasmid DNA from strain ADMX6L was digested with SspI and pUC19 was digested with SmaI. Plasmid DNA from transformants giving white colonies was isolated and double digested with EcoRI and BamHI, and separately with PstI and SphI, in each case giving the expected fragment sizes for correct insertion of linearized pADMX6L4 DNA into pUC19. Partial DNA sequencing into the pADMX6L4 region using the M13 primers of pUC19 further confirmed the identity of the pADMX6L4 insert. The chimeric plasmid containing linearized pADMX6L4 cloned into pUC19 was named pXB4. An *E. coli* host transformed with pXB4 was deposited in the patent collection of the National Regional Research Laboratories in Peoria, Ill., U.S.A. under the terms of the Budapest Treaty as NRRL B-30435.

Example 9

Definition of DNA Sequences Comprising Replication Functions of *Ketogulonigenium* Plasmids Various programs of the Wisconsin Package version 10.1 (Genetics Computer Group, Inc. Madison, Wis.) were used to analyze the DNA sequences of the four endogenous plasmids from *Ketogulonigenium* strain ADMX6L. The analysis revealed multiple open reading frames (ORFs), nucleotide sequences having protein-encoding potential, on each plasmid. The predicted amino acid sequences of these ORFs was obtained, and a similarity search against PIR and SWISS-PROT protein databases was conducted using the GCG implementations of the FASTA (*Proc. Natl. Acad. Sci. USA* 85:2444–2448 (1988)) and BLAST (Altschul et al., *Nucleic Acids Research* 25:3389–3402 (1997)) methods. Based on sequence similarity to known plasmid-encoded replication proteins, plasmids pADMX6L1, pADMX6L2, and pADMX6L3 were found to encode potential plasmid replication proteins. The genes (ORFs) for these functions have the following endpoints:

| | |
|---|---|
| pADMX6L1 rep ORF: | bases 2255-2710 of FIG. 1 (SEQ ID NO:1) |
| pADMX6L2 rep ORF: | reverse compliment of bases 3960-2562 of FIG. 2 (SEQ ID NO:2) |
| pADMX6L3 rep ORF: | reverse compliment of bases 5031-4003 of FIG. 3 (SEQ ID NO:3). |

A region of DNA sequence upstream and downstream of the regions defined by these ORFs, perhaps 500 bp in each direction, is likely to contain transcriptional promoters, terminators, and other sequences required for proper expression of the replication proteins and control of plasmid replication. Therefore a region comprising part or all of the plasmid replicon for these three plasmids could be defined by the following DNA sequences:

| | |
|---|---|
| pADMX6L1 replicon: | bases 1755-3210 of the FIG. 1 sequence, also represented by SEQ ID NO:5 |
| pADMX6L2 replicon: | bases 455-2060 of the FIG. 2 sequence, also represented by SEQ ID NO:6 |
| pADMX6L3 replicon: | bases 3503-5531 of the FIG. 3 sequence, also represented by SEQ ID NO:7 |

All publications mentioned herein above are hereby incorporated in their entirety by reference. All publications cited in the annotations to the Genbank accession numbers or in ATCC strain descriptions cited herein are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. An isolated or purified nucleic acid molecule comprising a polynucleotide comprising a replicon functional in *Ketogulonigenium,* the polynucleotide having a nucleotide sequence at least 95% identical to a sequence selected from the group consisting of:

(a) the nucleotide sequence of SEQ ID NO: 1;

(b) the nucleotide sequence of the *Ketogulonigenium* portion of the plasmid contained in NRRL Deposit No. B-30418;

(c) the nucleotide sequence that is the complement to SEQ ID NO: 1; and (d) the nucleotide sequence that is the complement to the *Ketogulonigenium* portion of the plasmid contained in NRRL Deposit No. B-30418.

2. The isolated or purified nucleic acid molecule of claim 1, wherein said isolated or purified nucleic acid molecule has a nucleotide sequence that is at least 95% identical to that of part (a).

3. The isolated or purified nucleic acid molecule of claim 1, wherein said isolated or purified nucleic acid molecule has a nucleotide sequence that is that of part (a).

4. The isolated or purified nucleic acid molecule of claim 1, wherein said isolated or purified nucleic acid molecule has a nucleotide sequence that is at least 95% identical to that of part (b).

5. The isolated or purified nucleic acid molecule of claim 1, wherein said isolated or purified nucleic acid molecule has a nucleotide sequence that is that of part (b).

6. The isolated or purified nucleic acid molecule of claim 1, wherein said isolated or purified nucleic acid molecule has a nucleotide sequence that is at least 95% identical to that of part (c).

7. The isolated or purified nucleic acid molecule of claim 1, wherein said isolated or purified nucleic acid molecule has a nucleotide sequence that is that of part (c).

8. The isolated or purified nucleic acid molecule of claim 1, wherein said isolated or purified nucleic acid molecule has a nucleotide sequence that is at least 95% identical to that of part (d).

9. The isolated or purified nucleic acid molecule of claim 1, wherein said isolated or purified nucleic acid molecule has a nucleotide sequence that is that of part (d).

10. A vector comprising the nucleic acid molecule of claim 1 and at least one marker gene.

11. A vector comprising:

(a) the nucleic acid molecule of claim 1;

(b) a terminator of transcription;

(c) a promoter; and (d) a discrete series of restriction endonuclease recognition sites, said series being between said promoter and said terminator.

12. An isolated nucleic acid molecule comprising a polynucleotide comprising a replicon functional in *Ketogulonigenium,* wherein the polynucleotide hybridizes under stringent hybridization conditions to a sequence selected from the group consisting of:

(a) the nucleotide sequence of SEQ ID NO: 1;

(b) the nucleotide sequence of the *Ketogulonigenium* portion of the plasmid contained in NRRL Deposit No. B-30418;

(c) the nucleotide sequence that is the complement to SEQ ID NO: 1; and (d) the nucleotide sequence eeniplementaiy that is the complement to the *Ketogulonigenium* portion of the plasmid contained in NRRL Deposit No. B-30418;

wherein said polynucleotide which hybridizes, does not hybridize under stringent hybridization conditions to a polynucleotide having a nucleotide sequence consisting of only A residues or of only T residues.

13. An isolated or purified nucleic acid molecule comprising a polynucleotide comprising a replicon functional in *Ketogulonigenium,* the polynucleotide having a nucleotide sequence at least 95% identical to a *Ketogulonigenium* replicon sequence selected from the group consisting of:

(a) the nucleotide sequence of SEQ ID NO: 5;

(b) the nucleotide sequence that is the complement to SEQ ID NO: 5.

14. The isolated or purified nucleic acid molecule of claim 13, wherein said isolated or purified nucleic acid molecule has a nucleotide sequence that is at least 95% identical to that or part (a).

15. The isolated or purified nucleic acid molecule of claim 13, wherein said isolated or purified nucleic acid molecule has a nucleotide sequence that is that of part (a).

16. The isolated or purified nucleic acid molecule or claim 13, wherein said isolated or purified nucleic acid molecule has a nucleotide sequence that is at least 95% identical to that of part (b).

17. The isolated or purified nucleic acid molecule of claim 13, wherein said isolated or purified nucleic acid molecule has a nucleotide sequence that is that of part (b).

18. An isolated or purified vector comprising the nucleic acid molecule of claim 13.

19. The vector of claim 18, comprising a replicon in an organism of the genus selected from the group consisting of *Acetobacter, Corynebacterium, Rhodobacter, Paracoccus, Roseobacter, Pseudomonas, Pseudogluconobacter, Gluconobacter, Serratia, Mycobacterium, Streptomyces* and *Bacillus.*

20. The vector of claim 18, comprising a replicon functional in *Escherichia coil.*

21. A transformed cell of *Escherichia coil* comprising the vector of claim 20.

22. A transformed cell of the genus *Ketogulonigenium* comprising the vector of claim 20.

23. The vector of claim 20, wherein said *Ketogulonigenium* replicon is SEQ ID NO:5.

24. An isolated nucleic acid molecule comprising a polynucleotide comprising a replicon functional in *Ketogulonigenium,* wherein the polynucleotide hybridizes under stringent hybridization conditions to a sequence selected from the group consisting of:

(a) the nucleotide sequence of SEQ ID NO: 5;

(b) the nucleotide sequence that is the complement to SEQ ID NO: 5;

wherein said polynucleotide which hybridizes, does not hybridize under stringent hybridization conditions to a polynucleotide having a nucleotide sequence consisting of only A residues or of only T residues.

* * * * *

SEQUENCE LISTING

<160> NUMBER OF SEQ ID NOS: 10

<210> SEQ ID NO 1
<211> LENGTH: 7029
<212> TYPE: DNA
<213> ORGANISM: Ketogulonigenium -continued
<220> FEATURE:
<221> NAME/KEY: misc_feature
<223> OTHER INFORMATION: pADMX6L1

<400> SEQUENCE: 1
gccatttctg cgctgcactt cgctaagggt tcaagggaaa cgcagggttc ccttgcccac 60
acaaacgcgc agcgtttgta taagtgggca cttcgtgttt gacacgctat ccactacgcg 120
gcacaaattc aactcttgta acgaggaagg gcggtagaat ggcgcgcacc atcgaccagc 180
agatcgcaga tgcgcaagcg aagctggcgc ggctcaaaac ccgtcagaaa gccagcgaca 240
cccgccgaaa gatcatcgtc ggcgccatcg tcaccaccga ggccctgaaa gaccccaaga 300
tttccaaatg gctggcatct accctgcgca agaacgcaac ccgggacgtg gaccagaagg 360
aaatcgccgg gctgctggcc gacctcgatg ccagggcgca aagcgccggg gcgggtgagg 420
catgagcggc agcaccgatc cgtttctggt tctggtcgat gatattggcg cgctgcgccg 480
ccagatcgag aacctgcaac gcaccagcct cgacagggac gaggccgaac atctcaacgc 540
gaccatcgcc cagagcctcg acaacatggc gcaaaccgga aaacggctgg aacagcgcct 600
tgagggccag ttgcagctcg ccaccgccaa aacccacagg gacgccatag aagccgctca 660
gggggccgcc agagcggcta tcagggaatc ccatgccgag atcctccaaa cggccaggag 720
cctctcacag gccgcaggag aggcccgcag agaggcgtgg cgctggttcg gcgggttctg 780
ggtctggctg gcctcgatcg gggccgcagg ggcgcttgtc ggcgcgctgg ccgtgttctg 840
gctccagggc cgcgccgatg ccaaagcctt cggacagtat cccagcatct actgcaccac 900
cgcaggcggg gcattcgccg atcagcgcga cggaagccga tactgcatct tcatgatttc 960
accgccgaca cagccagacg gggaatgacg gcttacgcgc cgggctggat cgagactttc 1020
agcccgagcg ccttagcgac cttcatcacc gtggacagcg tagggttccc atccccggat 1080
agcgccttgt tcagccccac ccggctcatg ccaacctcac gggccagcgc ggtcatgttc 1140
cgtgcgcggg caaccactcc aagggcgcgg gcaacatagg cgggatcgtc gccgccatct 1200
tccatgaccg cttcgagata ggccgcaata tcttcctcgg tcttgaggta gtcggcggaa 1260
tcgtagcggg cgaatttttc ttccggcatc gcttagccct tccactctgc ggccagcacc 1320
ttggcctgtt tgatgtcttt gctctgcgtg gacttgtcgc cgccacaaag caggatcacg 1380
agaaccggcc cgcgctggat gaaatacacc cggtagcccg gcccgtagtt gatccgcagt 1440
tccgaaacac cctctccgac cggctccaca tcgccggggt tccccgccgc aaggcggtcc 1500
agtctggcag tgatgcgcgc aaccgccctg cgatcccgca aaccggaaag ccaggtatcg 1560
aaggttccgc ttcggattaa ctcgatcatt cgacaactat agttatcatg tgggtgtctg 1620
acaaccagag ttatcacttc cttgttctaa gcaaatccga ggccagccac gggcgtagcc 1680
ggagcatcat ccctcccccg cacccccacc cgtcacgcgc acacatgcgc ggaatcgtcc 1740
actcggccca caaggggcct tgcatccgat ggcaagcaaa aactacccag tccgtccgta 1800 ggcgggggt cgccagccct gtgggtgggc gcttcccccc ggcccgcaag cgggcccgga 1860
atgggcattt tttgcctgcc ctaagatcat aagaagggca aaaaaaacat cgtttcaaaa 1920
cagcgtgtta ccaccccccct ataggacacc agagtccggg gtagaggact ctggtgtcct 1980
cttaggccat ttatgtccaa gaatgtgaca gccagccgag cggaggtaga ggactctggt 2040
gtcctatgct taggccattt atgtccaaaa acttgacaag ggccacattc ctgccaaatc 2100
tgtccagaat ttggaaaaat tcgccggata gtagacagtg gcaaagcctc cccccattcc 2160
cgcaaagcgc ccgctcggca cttgggttca aactgaccgg gaagcccacg aggcgtgggc 2220

-continued

```
gatactggca aaaaagcctg ctgccagcgc tgtgatgcac attctgtgcg ccaacctcgg   2280
tgagcataat gccgtggtca tcagccagga caccatcgcc aagctgtgcg gcctttccac   2340
acggtccgtc aggcgcgcca tcgtcgatct ggccgaaggc cgatggatcg aggttcgcca   2400
acttggcgcg accagccaga ccaatgccta tgtcgtcaac gaccgggtgg catggcaggg   2460
atcacgggac ggactgcgct acagcctgtt tagtgcggct atagtcgtgt ccgaggagga   2520
gcaacccgac cgcgctgaac tcgaccagca agccccccctg cgacacctgc cacgcatcag   2580
cgaggggcag atacccaccg gccccggcct gccgccacct tcgcaaccgt ttctaaaaga   2640
catggagcca gacttgccca ccattgaccg ggcaacatca cccaactttg accagcagga   2700
acaggggtga aaaaggtgga caaactttcc atacgcgagg cggtaaaaca cttcgatgtt   2760
tcccggccaa ccctgcaaaa agcccttaaa tctggcaaga tttcaggtgt tcaggatgga   2820
caaggaacgt ggacaataga cccctcagag atggcaagag tttaccagcc aaggcaagat   2880
gaggtggtaa aggatggtgg ccaagaacat gaaaatttgt ccgccaagaa caccccttta   2940
catggtcaag ttgaggttct gaaagagcgg cttgcagatg ctgaaaaacg ggtggcgata   3000
gccgaggcac tggccgaaga acgtggaaaa cacatcgagg atctacgccg gatgctgcct   3060
gcaccggaag ccggtcagcc ccgccgccgc tggtggccat ggtaaggtca gctatgcggg   3120
accaagccgc agctcgcaag tgcggcaaca gaatcagacc cgcttcggac agagagctca   3180
agctggtgga aaaccgcctg tgaagctgct gggtggcagc cgctttactc agcgaagcag   3240
ccattcgggc ggatcgcagc gagattgccc catccagtcc taagggccgt gtaaacagca   3300
cttagtgcag cagcatcgca ggcgcggaaa tctgcctgcc cttcctcgcc acctctgagg   3360
cgtcagcgat ctgccccaaa cctgcctgcc actttggcgc agcatgttgc ttgagaacac   3420
ggagctgccg atctctgcgc taagcagaat ttcctgataa tacgcacaga tgcaaataat   3480
attgcggcat caatgcgttt ccgtttaccc ctaggcagtt gcctcatcat gctgtcgttc   3540
gctgtccaag ccgcaacgac ctgcgaccga accttcactg catcttactt tcggcccctg   3600
cgttcgcccg tgaccgcagc gcggcccaaa gcgcgaccgc cgccaaggcg ggtaggaaca   3660
gccccattgc catcgggaac gggctgtcgg tcccggccaa ggccacgcag gtcgaaatcg   3720
tgaaggccat cccgaactgc accgcaccca agagtgccga tccagttccg gcggcctcgg   3780
tcgcggcggc catggcaagc gaggtcgcat tggccgaaag cagcccgacc atgccgatcg   3840
cgatccagag cggaatgata aacatccata ccgaacccgt ggcagaggcc aggacggctg   3900
ccagcgccgc aagaccatag aacggcagtc cccggttcag catgtcccgg ggcgtaaagc   3960
ggtccaggag gcggctgttg atctgcgcga agacaaacag cgcggctgcg atgagcgcaa   4020
atatcaaccc gtagttgagt gcgctcatac cgaagaagcc ctggaacacc ccggacgatc   4080
cggtgatgaa ggcgaacatc ccgccctgga ccaaccctgc caccagcacg gggcaaggt    4140
aggcgggctg tctgacaagc cgcaggccgt tccttgtcgc gcttcggaag ggctgcgcga   4200
cacggcgctc tggcgacagc gtctcgggca ccaccagttt cgacaggatg agggcaggca   4260
gaccgaccag caccattgtc acgaagatcg accgccagcc gaaggcctcg agcagcaggc   4320
tgccaagtgt cggcgcgatg accggaccta tggtcatcag catcaccagc aaggtcatca   4380
ccttggccgc cttttgcccc gagtagagat cggcgacgat ggccctgctg acgaccatcc   4440
ccacgcaggc cccgatcgcc tgcaaaaagc gcagcgcgtt gaagacaacg atattgtcga   4500
ccagcggcag cgcaattgat gtgacggtga agatgaagac gccgatcaga agcggccgct   4560
```

-continued

```
tgcgcccgta tccatcggtc agcggcccga cgatcagctg cccgaggcaa aggcccagaa   4620
agaacagcga cagtgaaagc tcggtcgccg catggctggt attcagatcc tcggcgagaa   4680
tgccgatggc cgagagatac atgtcggtcg ccagtggcgg aaagatcgac aaaagggcga   4740
gcacggcgat caaggcaccg gctcgggcag ggatgagggg gcggtccagc atgatatcct   4800
cttggcggga tggtgcgatt ccatttgtag atcgcagtct actaatgtaa aattatactc   4860
aagtctataa ttcaagtcgc ttggccggaa tcgcaggaga agacaggaat gcaggaggta   4920
cggagcggac cgggacggcc aaaagacccc gtggttgccg aagcgatccg caaggcggcc   4980
ctgcggctgg tgcgcgaaag gggataccgg aacgtaagca tcggcgcgat cgcgcaagcc   5040
gctggagtgg cgcggcaaac gctttacaat cgctggcacg cgaaggccga cctcatcctt   5100
gatgccgttt tcgaagagac cgggcggcgc gccgacgatc aattaccgct ggaaacaggg   5160
gacgcgtccc gtgatcggct ggaacggctt cttataggtg tgttcaatca cctccgggcg   5220
gatggcgata cactgcgcgc attgatcgcc gccgcgcagg aggacagcga gtttcgtgag   5280
gccttccggg aacggttcgt cgcaccgcgg gaaaccatcg tcaccgacat tctggccgaa   5340
gccctgcgcc gtggcgagct ttcccgggaa gccgacccgg ataccttgtc gaccatgatc   5400
cacggcgcat tctggtatcg cctcctgaac ggacgcgagc tcgatcatga actcgcccga   5460
tcaatagcgc ggagcgtgtt tccctgagcc aagacgaaac ggaaacggac ccaaatcatc   5520
ggaatgtata aagtcgcgca tcgttaccat cctgaggggg tgatcgctgc ggagcgagac   5580
gaatggcagc taccgggaat gcggccacgc cgcattggtc gaggtcggcc agggcaaagg   5640
gctggccttc acctatacaa gcgacaggcc tgccatgcgg cgccctgccc aagtgtcagc   5700
gatgggctca aaccgtcgat aggccagccc cggcccgctc gttccatcgc gggctgtagg   5760
gtcggggctg gccggatcag tgagtaagcc cgccatcccg gtcgtggtca cgggcttctc   5820
gctcccgcaa ccgttcctgc tgccgctctt gctccttcag gcgttcggcc tcctgcaccc   5880
gctggcgttc ctcggcctcc cggctttcct gcaaccgcgc tgccgcctcg gccagcgtgc   5940
cccggtcgat cccctgcgcc gcctcccgta gccgctcggc caggctgcgg gaggattccg   6000
gttccggggt ttgtccaggt gcagctatgg catcggacgc ggtgcggctc tggcgggcct   6060
cccatgcctc gcgcaaccgc gcggccaggt cctgcctccc ctcccggcca tcccgatccg   6120
cagcgccggc ataagccaga ccctgcgccg ccccctcttg cgtcaacggc ccgaggcgat   6180
ccacagctcg cccgatccag tcgcgcacct gaccggccag aacctccgcc acacgcgcaa   6240
cctcggccgc ctgcgccttg acctcgcgcc acacccggac ggccccgacc tcgataccgc   6300
gttccttcat ctgccacgcc ccggcagaca gttgcggcaa cggatcccgg tccagttcca   6360
ccgcccgcac cgtttgacgc agcgcctcgg cctcgtcgcc gcgatcatgc gccgcgctgg   6420
cccgctcctg cgcctcgatc cgctgcgcct ctagcgtccg gtggtcgatc cgttcctcat   6480
ggccgcatcg ctcaagggcg cggttgctgt cccgcgccca tgcctcacgc catccttcca   6540
gcatctcgac cgcgttccag tcccggttct tcgccccgaa cccctcgggg ccgatttcgc   6600
gggtggtcag caggatatgg gcatggtggt tgcgatcatc gccggtccgt cccggcgcat   6660
gaagggcaat gtcggccacc atgccacggg ccacgaactc gcgctggcag aattcgcgca   6720
ccagctccac gcgctgtccg tggtccagct cggcgggcag agccacccgg atttcgcggg   6780
cgacctgcga attcttccgg gtctctgccg cctcgaccgc gttccacagc gcctcccggt   6840
cctgcaccca tgcgggggcg ttggcagggg cgagggtttc gacgtgatcg acaccgccac   6900
gcgcacggta atcgaaggtc agcccggtgc ggtgatcctc gatccgttcg cccacgcggt   6960
```

-continued

```
aggccgcagc cgccgtggcg ctacgaccgg aagagcgaga tatcatcgtg gcccgaaggt   7020

gatagatcg                                                           7029


<210> SEQ ID NO 2
<211> LENGTH: 4005
<212> TYPE: DNA
<213> ORGANISM: Ketogulonigenium
<220> FEATURE:
<221> NAME/KEY: misc_feature
<223> OTHER INFORMATION: pADMX6L2

<400> SEQUENCE: 2

gcgtctgtgc gcatactatc ctccgtgttc atcaggctca cgcctgatct gattagggct     60

cttgtctctg cttgtatcgt cgccaaacta tactttaagc agcgtctaga gcctgatgaa    120

cgatctaaga agcccgcccc ctgaaaggcg ggcttttttg atctgtgcca gatgttgtta    180

catcggcgct caaaaatcaa gtttttttctt gactttcaat aatttgcatt atgcacatta    240

ttatcgtttg ataataagag ccagaacagc acagaatagt tgtgcgatag ctatgaataa    300

tagcagatcc atccctgttt cctttcttac taaatacaat gcgaaactgc tcgcatctgt    360

tttatttagt tgaatcggaa actccaaatc ggccggattc aaaaaaaata tagactatct    420

ttaaagtagc aacgccgccg ctcgcgcgac ggcattgcgg gaaatgcgat agcaacaaaa    480

ccacttattg tcgtatatcc ccactttcaa gcgaagcgcc ccgcgaagcg atcaaaaaag    540

aaagaaagaa gggggcgctg cccccgtcat gcgcaagcgc atgactcccc cgcccctcac    600

tcaccaaagc agcagctacg aagcaggacg ggatcggcgt ttgtgcatca cgtgctcgca    660

tcaccaacac aaatagacgt atccccatga atggggcccc acgtcgattt gtgttggcgc    720

tactgcgcgc gcaatgccct gcagcctcac ccgaccggct ccgaagcagc agcttttaag    780

acagtgagtg acacaagaaa acatgcgcaa gcgcatgtgt gcatcgcgtg cgcgcgatgc    840

acgggaaggt tgccttcgtt gtatataata atatagcctg cacgctgtgc gcacagcgtg    900

catgagaggc aaaaacatgt caaaaatgtt gactactgca caagttgcac agcgctttgg    960

actgtcacga tcgacagtta gcagagcgct taaaaacggc gacttgcgtg gcatccgcga   1020

caatagaggc gtgtggaaaa ttgccgaaga tgatgcgcat aaatggcgca gcgacgccgt   1080

gcatgaacag cgtgcgcaca gcgtgcatga cagtgcatta cgcacacgtg ctgaagttgc   1140

ggaagctcgt gcaacagcgc tagaaatgca cgtgtctgac ttgcaaagcg agcgtgacga   1200

cttgcgaaag cagcgcgacg agctgcaagc gaagttagac ggtcggcccg tcgaaactgt   1260

cagtatcagc cagcttttcg ggcgcctttt tcggcgctga catggcgcgt agaagcgcga   1320

cagtctcagc tttcgttcgc ttcatctgcg gcatgatctt cacagcatca gtgcgtgctg   1380

cgcgtgtctc ttcgacctct tttctagagc cgagccgcaa tgcaatctga atagatctgc   1440

gtattcgcgg caagctttta cgcacttctg aaatcgcttc atcgagcgac ttcaagcgct   1500

ctacaagaat gccgcgcaag ccagaaactc gcttgcgctc agccctgacg gcttcgacag   1560

cgacagactt ttgacgctca aaatcgactt gtgcagcatc gagctttgca cgctctgcat   1620

cgagctgctc gcgttgtgtt ttaagctctg tgcgctctgt ctcgacagct ttaaaagcct   1680

cagtttctaa gcgatccggc gcgccgtccg acttctcacg cttaggctct agcttgatgt   1740

tattccgacg ctcgaaaaac gcagcaaact cgctttgcag cgcaataccg accgcgcgcg   1800

gcgcgctata gtttggcgct gccccagaat gccgccgctg gatctcttcg cgatgtttat   1860

cggccagctc gcgaccaaat tttgtggcgc tcgaccacat ttcgccaggc tgatccggcg   1920
```

-continued

```
gcgttctttt cgtgcgcttt tcataaactg gcgaagcaaa aacatcgacg atgctctcgc   1980
ccgcctcgtc tctgtctagc ctcgctgcaa agacagcgtt accgccgtgc gtttcgttta   2040
taaactccac tgcttggcgc accatggcgc gctgcagctc ttctttgctt ctgttggttc   2100
ttctctcgtc aagaagctca ggcggaaacc gcactataaa gtgcagaaca ggcttcttcg   2160
ccgctttgtt ttgcctaacg ccttttgtgt gcgcgtcata tgccgaccga aggtctagcg   2220
tcttataaac gagcggagag gcatctctta cgacgcgttt cgcacttgtt ttgtcttgtc   2280
gtttcgcgtg cttttcggct gctgacaatc cagccatatc taacgcacta catctcaccg   2340
ctgctttcat tttcaatccc tcatatatta ccttttctgt tgtttttgcg aaaaacgcaa   2400
aactcgcttt gcgtttttttg ttcggcacct gcggcacctc caaaaaaacac gcttgctctc   2460
cgagggtctg gcaggagcct aagagggggc attctgcccc tgatcgaccc cattgaggct   2520
cgatctaaac agacccccca caggggcgtc tgtgggccgc tagtgcggcc ttccgccatc   2580
ttcgagccat ctgatctctg caattagaga tgcatggcgc atctcccatt ccagctcaga   2640
tatcccgtat ctgtcgatga cggtgtcata caattcgtcg agccttgctt cgcgctcttc   2700
ttttgtcatg ccagttgcat cgcgttcttc catctcctcg ttctcctcta tgatgaaatc   2760
attttcgtcc tcgtcgtttg gcccgctttc tgctgccttg accgcaacag cgcctccgcg   2820
ctctgcggcc tcgagcaagt tcacgcgttt agcgcgcact tgcttccacc cttcattgtc   2880
ccactccgcg acaatttcag ggccgctttg ctctgctgca tcaacttcag ccatagcttc   2940
atcgtcatcc agctcgacca aaccgcattc ttctttcaag ccttggctcc acaccaattg   3000
ccgcctacgc ttgccgctcg ttgcattgaa atattcgagc caaagcccgt catcgcccgc   3060
ctgaagtagc tgccttggcg tgcgtccttt gcgttttccg ctcttcgagc ttgaaagcgt   3120
caactcttcg gcagcgcccc acttcgctac gtagtcgccc gcattggcag ccccgcgaac   3180
gtcaaacgcc gcatcgttgc cccacatgcc ataccccttc agacatgcac gccacgcatc   3240
gcctagacgt tgcatcagat gcagcgcttc gctttcatcg ccagctctta gcaagacaat   3300
ttcgtgaaag tgcgggtgcc acccatttgc atagctatga gtaatttcag ttgatgtgac   3360
tgacccaaca aatggtaaat cgcgccactc gcggcgctga cgcaaccgct gtttcgcctt   3420
cttcatgttt tggagaagat caaaaagcga atcacctgct ttgtgctggg ctgtcagagt   3480
tatgagcacc ggcacaaacc cgttgtcgcg cgcccacgcg agcaagtgat tcatttcaga   3540
acggcgaatt tgcgcgatgc gagcgctaca aactgcgcag ccccacacat tccggcactg   3600
tgctagacct gaaaagaatg cccgacgccc gccatcctcg cccacgtttt gcacgtttag   3660
ctcaactgtc ggagacactt ttacgtgccg acatttcgca acttggtggg gcttgttttt   3720
gttcagattc aacagaatcc gagcggctga acgcagatct gcataaagct gccgcctact   3780
gaataacctg ttgttttctt tgttttttc attcggttga cccccattct ggtcaaccga   3840
tttacggtat ataccaaggg gggtctgccg accccctgaa aaagcgtcat cgccgcgcgc   3900
ctgcgcaccc gcgttcttct tcgatttctg aactgaatgt gatgctagtt tgtgagacat   3960
ggccgcaaac cccgacgggt gcggcgacta ttctcttgat tttct                   4005
```

```
<210> SEQ ID NO 3
<211> LENGTH: 19695
<212> TYPE: DNA
<213> ORGANISM: Ketogulonigenium
<220> FEATURE:
<221> NAME/KEY: misc_feature
<223> OTHER INFORMATION: pADMX6L3
```

-continued

<400> SEQUENCE: 3

```
cactttcgcc acaagatcag gcgcatgatc tttctcagcg ttcaacacac atttgagctc      60
ctgcgcctga tcgtcagtaa ggtaatatcg ttcttgcatc aatttctcct tagttggatt     120
ggttgcactg gatctttgcc ctgacagcct catgcctcga ggcctcggcg atgtcgtggt     180
gcattgtatt ctcgcggcac tgcatcgact tcttctcggt ttccttttgt tcgcactggg     240
tacatggatg tcgttgctgg tcacacacac cagagcacac ctacagctct cccatgcgac     300
cgccttggcc gcaccgagat acatcgcctt gtgtggttcg cgacttcggc agcaatcgcc     360
gtggcagctg gattggagca tcatcaggca agggcttcgc tgacagcgtt cgtcgtgaac     420
gcctaggggc tgtaaaccta aaactgcccc cattgaccgc cgccagaaga atgatccatg     480
tctagggtgc cccatgaatt acccgcgata tccggtgtgc cgtcgcctgc aacagtaggc     540
agaccgctag caggattgat cgagtgtatg ccaccaaatg tgccccctga aatatccagg     600
gtgctcaatt catccattgt atgcgctcca gaggttggga ttgtgctaaa ggattgaaca     660
gtatggtctg gagtacccca ccagttcaga ttcaaaaaac ttcctatcat tttgaacatg     720
attggcttcc ttttcgatta agttttcaac aaacagaatt aatctacggg ccagttgtgt     780
gcagaagagc gacggcaaat tgctgttata gtatttacga aaatggtcgc caaaaaatat     840
ctgtcgatca agtgttttct gtaaccatct gaactttttg ataaatatca aggtgtgagt     900
ggtttatgcg atgctttaca tctgacatct ggtaaccgcc cctgttttct cagggtgtag     960
aatgcagatg acactgaaaa tacaatgaag tgaatgagag ccgttgccct gcccagccaa    1020
ggcgaagatt tcattatccg ctgagcaaat cttgtaccaa agagggcttg cgttcaatga    1080
gggccagtag gacttgagct ggcccttgag gcatacggcg cttttgctcc cagttgagaa    1140
gagtgccctt cgccacgccg atactacgtg caaactccgt ttgagatagg ccggtctggg    1200
cgcgaatgcg cgcgacatct atctcaggca agctgatctc atgcacagcg gcaccggcct    1260
tttgcccagt cgaaaaggcg cgagcttctt ccaagccctg catgatactg tcgaacgcgc    1320
tcattgtttg ttgctccaaa tggcgatgat ctctttgctc atttcgaccg cggccgcctg    1380
ttctgtcggg gttaggttcg ccttttcgtt cttggcgaaa acggtgatca gaaatatcgg    1440
catgtggcgg ccgccaaaca cgtagatcgt tctgaacccc ccactcttgc cggcccctgc    1500
cctaggaatg cggacctttc tcaatccacc acccaaagcg atgccggcct ctggattttc    1560
tgcaatccaa gcaattgcag cgtcacgttc cgcatcggtc atgatcgatc gtgagcggcg    1620
ctggaactct ggcagttcaa ctacggtctg caggcttgtc atttaggtat acttcaatgg    1680
cgcataagtc aatggcgcac tacggcttct tgagctgctc aaggagcgca acagcgtgtt    1740
cgagggtttc accgaggccc caaccgttgg catctgctat tctgtaaaaa gattctatcg    1800
tttcaggcgt cgccttaatg ttgaactgcg cgtttcggcc agtcctacgg cgccgctgcg    1860
gcttggaaac agggggcgat ttaggctccc tgctcacgaa gccagacgcc tctgccgctt    1920
gttcagtgct gcggtcttta ggtgctatct tcggagcagg cgcgaagctg ctaagatcgt    1980
ttagtgcatc accaaaacca aggtttgcgc gttgcttgct catcactgat cctcttggct    2040
acgcttcagc tttccaacca cttcgcccgc aaattgccgc gcgttctcga ttgccttatc    2100
gacgttgctg acctgcgacg gatcaaggtc agacaaggtt ccgccatagt cgaacaagtc    2160
acgataggcc gcacgctcga caatcgatgt ttcgcatata tcgatgccac cgctcatgag    2220
ctgctcgtga acgtttttca gggcgcgtga gcgaaccgcg gcacttgttc gggtcagcac    2280
```

-continued

```
aacgcagtgc ggtatggcac gccgcgccat cttcgcttgg ttgctgatca atcgaatggt   2340
ttttgcgcca cctctcgcat ccatagacga gccctgtatc gggatcagta ccaggtctga   2400
cataccgata gcgtttgcga ccatcaggct cgcagtcccc tctaagtcga cgatcacgaa   2460
ttgagacgtg ccggatgccg cctcaatctg gtcaacaatg ccgtcttctg tcacgccgct   2520
tacgatggaa atattttcag gctttccggg taggctcgcc cattgggaga tccagcgttc   2580
tggatcggcg tcgatgattg tgacgcttgc cccgccctcc gaaagctgcg tggccaagat   2640
caaggctgat gttgtcttcc cagccccacc ctttggattg gcgaatgata tgacaggcat   2700
gtgtgatcgt ctccgcgctt ttaggtacaa tatcagatag ctaacagata tccatatata   2760
agttacagta tctagtagct atcggatatc atacaatact aaaatggtac tatttggtat   2820
catatgccaa atatcttgac ttcatgacca cttggttctg cggcaggtcc gacgaaagag   2880
cccggcgagg acgcttactt tttctttggc tgccattttt ttgcgagctt taaaacgtta   2940
cgacggagct catcgccatc ggggatatgt gggtcgaatg gaccttctac ccattgggtg   3000
agttcctcgt gttcagggtg tgcggcgtcg ccgattgcct cgatgaagtt ttcatatccg   3060
ggcaggccgc cgacgtcctc aggcggacat ctaccgacaa catcgacaag ccgtgggtag   3120
aggttttcgg gaatcggatc gtcgacgctc tccgtctcaa tcagatgaac ccagtaatct   3180
ccgaaatcgt aaacatatcg gatcgggtcc gctacggcag tgttgatgat gtcagctagg   3240
atgtccgctt cggaggtatc ctcgtagacg cggatcagtg cgaaattggc cttgagcgcg   3300
gccttgtcct tcaacttgtc ccgttcaatc actttgcgcg cactggcgct gtttttgccg   3360
tggtggcccg gcccgtcata ttcgatgatg gcgcgcacaa agccgtcctt gctccaaatc   3420
acgaaatccg cgcgctttgc gacaaggccc cgccacagat tgccttgagc ttggatgaag   3480
gcaccgtatg gcacctgcgg cgagagaata agatcaggtc tgttctcgtg ccgccagcgg   3540
ttaagcaggt tatagagccg aaattcactc ttattcatca attgcttgct gctgtagagc   3600
gattttcgcc cttcaacgaa ccagtagaca cccccgacaa gggcgatgac caccagaaat   3660
ccaattatca ttgtgaaatt aatgtcggtc atgactgcac tccctcaagg ccgaagtcag   3720
agattgcatc ttgacgcaga gcgacgagtt caacgccgtc gatgcggttt tgggtggcgg   3780
tagccgggct ggcgcggata cgcctaccgt tggcacggtt tctaggcgac atactgaggc   3840
aaaccggatt tccagtgggc tgcgtgcttt gttgtaagcg cgccatttca tccccccgag   3900
ggcaggggaa cggctcacaa cttccaaagg ccccgaaaaa ttctcgcgat gaccccacca   3960
cgggatttgt gcaacacaat cggcgcgcgg gacaggctca tatcaacttg gataagcgcc   4020
gcgtttttttg caaaatgcga gaaagtgctt atccgcatct ttcacgttga tggccttgtc   4080
atgcacccaa gaacgccact cttcttcaag ggagtaaaca tcccacccag gagcaagttc   4140
acgggcagta tcgcgtgtgt cgggatcgtt gaacggcaag gcctgaaaag tggttgatgc   4200
tatagtttcc accaccttgg gtcggaagac agcgttctct ccttcgatac tcatgctgta   4260
gtcagggaag tggtcgtgcg cggtgtcatc ctcaatgatc ttcgaaagca ggcgacggaa   4320
ctcttttttta gttgagccgg aaccgcactt gtttcgcaag agctccaagc tacacatcca   4380
ttttgactgc gcgccacaat gctttcgccc tatctcatac aaccgccttt cgaggggctt   4440
tctgagcagg aaataccccc ggcttagagt gaggacatgg ttgttctcga tcgcatcaaa   4500
gacccagtca gagagcgtta tttcgacatc aagcattcgg ccgtcgcggg ttacgcgcac   4560
gatctcggct gattcaatca ggccaaatac cttgaagtat tctttcccac cttgacgaat   4620
attcgtttca atttgggttc cctgcagccg ccgaagggca tctttgagca gctgataacc   4680
```

-continued

```
ctgaccggat gtctgacggt tcgttgccac aagcagatca taagccttga aacgcatcga   4740
tctacttatt ttctgcccct cattaatggc cgccatgcac tggctgatgc agtagatcag   4800
cacatcacgg tcatgaacgg tagcaaggcc atagcgtgaa ggggaaacct cgatccaatt   4860
gtcgttgttc tgatagcggc gtggcttcat gtccggcttt gtagacaggg tgaacatagg   4920
gtgctccatc gaagccatat ccccttggg aaccgcatca acgatgtcgc aaacgaaaag   4980
gtctttttgt ggatgacgat ccggcaaaag cggtgatcgt aggttcgtca tttcacacac   5040
tcccgcgcca agtaaaaatt cgtcatttca cacaccgtac aagactatcg tcatttcaca   5100
caccactcgt caaggctcgt catttcacac acccaaggag gctgtggata actcgagccg   5160
ctatcgtcat ttcacacacc atctttcgtc atttcacaca ccatctttcg tcatttcaca   5220
caccaggtgt tatttttttt atagttatat caattgatta cgagctgttt tcggagctgt   5280
aactctattc taactctatt ctaactctca tagcttgcca aaatggcacc tcatatcccg   5340
gatatccggt ttcattatga aaccaatcaa caacatttac ggtgtttttt gaggagcaac   5400
actgtcccaa cgcaggttca aaccgatcac gccgaatctg caaagaaagg ggcagtgcta   5460
tgttcatttg gtcactcgag gatcacccga accacaggta agccctcaca tgctatgttg   5520
atacctccag ggaagtagca aaggtcctca cgaccaccac ctgcaggatc tccatcagcg   5580
aagacaactg tcgcattgaa cgctggcgcc ggcttgtacg tactcggtat gggtgagaag   5640
tcaggcatac ctgggagaac acgacgaagg acaccgtggt tctcgaggat cccgtagaag   5700
atatcgggcg tcccattatc cacataagcc gcaccatagc gatcctcccc gtagagatac   5760
tcacggaaag tttgcatatg ccgccagcga gagcgaaaaa ggggaacccg aatagcgaga   5820
tcctgatcgc ccaaccaaat gtcagccatg atgaacatgg aatattgatt gttccacgac   5880
gacaaagccg caaattccat gaaccgtctg accgcatgca ggtcagagcg ctttggctcc   5940
atacgatgaa gagggtttac atctcgttca acactgcgac gatccgcctt cttcaccgcg   6000
ctcacaaatg gactgcgatg taatcggccc tcaaggtagc cttcaagctg ttccgcatag   6060
gcctcatcac gcttagagac actctccaag aggcagtcag aaacgacctg acgccagtac   6120
ccattcccac gcgctgtgtc gtgacctatg acgggcctct gattgtatcg cagggagagg   6180
tgcgtaaccg gagactcgaa gctctgagac cattcccaga ggctctgagc catgggatcc   6240
cacgaaggaa ggtccgtctc tggttgctct atctcgccaa aacctaaatc ctgcagctgc   6300
acattcgcag gatagacttt gaacatcgtt cgcaccttgc cgaggtcatg aacaaagccc   6360
gcgataaaag ccgcaagatc gcccgcctct gaggggacgg ccttactgaa ctcactgttg   6420
aagaaatcta ccgcaagccc agctgtttcc agggagtgat agaatagccc accggctgtg   6480
cggtggtgat gtgtagatga agctgggagg cacagcatat agtcgtggcc tccgcgcaac   6540
atttgcctca ccaagagtgt ttctttgtga gagaggaagg ggagtttttt gagctgctcc   6600
ttgatcagct gctcatagct tccaaacgtc acatgcgggt gcaatatccg gaactgagcg   6660
ttgcgcaggt agcgcccgta agacaggatg atgcgatcgt cataaaacat tggcggtttc   6720
ctcaatcgat atttgctctt agttggtagg tgcccgtatg ggcgcggcac aggtttctca   6780
gctgtgccag gcggtcagtg cgatagcgga tccaggcgaa gttggcctcg cacagaagca   6840
gttctctacg gatggcgtct ggaaagcgcg cgaagatccg atcgctgtat ttgtactttc   6900
ctgacatgcg gatctgttcg gttggggtga acttgtcacc tcccatccgg tagcgggcct   6960
tgccttggaa tttgacccag taaatgcgcg ggcccaatgt gtcctcgcgg attcgaacga   7020
```

-continued

```
caatgcccaa attcagcgcc tcggcgcccg cgtccatttt gcgataggcc ttcagggctt   7080
cgacagcccg atcctgccaa tagcgcgccc atccttccaa gtcataaccc atcgctggaa   7140
tggatcgcaa aagctcaggc tcccaatcgg agtcgaaatc atgaaagcgc acttcgtgcg   7200
aacagctctc ttgggggtgt tcttcagaca tgctgtgctc cgaccaaatg gcgcgccgac   7260
caaaacaaga aggttgggtt caatgccggg atgtttctgt ctgcgttcag ataaagccca   7320
tgtttcctaa tgtgacggga tggtagctcc gtcacattag gggcgacgc atttgcgcg   7380
gcacatggcg cggagagccc gcaggcaggc ggctggacgg acgaaaatgg gcaggggccg   7440
cgctgagatc ccttgaaagc ccatgggcct aatgaatggc gctcacacag cctgtcatgc   7500
gtgtacttta cggggaggtc tcgcgatgag gtgagcgccc gcggtctctc gtcttggtcg   7560
tgtctgaccg tatgtgtccg tcgaataaac gtcatgatga ggtcctgaga taagaacgaa   7620
caggatcgtt gacggagggc atccgtctga ctgtcgtctg atgttgatgg aaagtcgccg   7680
gctctaggcg gccggtctca atttggtggt gagcagctct ttgcgctggg gggcattacg   7740
atgcagatca gccgtccagt ttaaatcggg aggggtgagg gaggtcgggg cggccgtgca   7800
caagacaatg gcatccgaaa gccggtcaat cattgggcgt atttgtccta cccatctgtg   7860
ccaattcata gcaaaaatcc cgaaccatcc gtttcgtcac acctattggc taggggggagg   7920
tggggatggc cgtcaatgaa aaatatcagg gattgagttt tataattaac tgaaattgct   7980
aaatattttt ggaaggaata ttccttccgt agctcgtcta ctcatttatc ccttttcgaa   8040
aaaagactta acagcgggcc aactgtttcg catgatgcgg acaagaaaaa ttggctatca   8100
tgggagtgtt cgggtggcgc gtgggactaa gacagccaaa agcaaaaatg ctgatccaat   8160
tgtagcagaa tgcttaaaac tgattcgcga agacagtggg tatgagagag atgaattcgc   8220
cgaacttcta ggggtgcagc ataaaacgta tcgcaactac gaaggctgta tatatccgct   8280
accgttaaaa gtggtaaaga cgatacgtga gaagttgggc tatgatcttg cggatcctga   8340
tctgacttca gacgcgatca tcaccaaaat tgcagagcag cgacacgatg ttgcagccgc   8400
tcctgatctt gccgcgacag agcaagtagc gaagggcgtt agttgccctc agaggatacg   8460
tacctgcctt caagctttcc ggcaggaact cattggtgtc cagagcaagc gcaagcatga   8520
tattcgagac gcagtttttg tcggagcagc tgcattgttt gctttctgct tggtggtact   8580
acgcactgaa ccgcaaaata taaggttaga gtctatctat acccttatgc tatccgtgtc   8640
cttcttggtt gcggcgtcaa ttgtcccgtt tcaggctata catatgatcc aagccgccta   8700
tcggtcgcga cgttgaccaa caatactagc cctccccgta tgcccgtctc acagggaggg   8760
ccaaagctac cttggcgaac gactgtcagt gcacgaaacg ggtgattaaa cgcaaagtgc   8820
tgactttttt tcccccgata ccgatggttc atcaaagata tatcgactga gcagatcggt   8880
gtccggggca cgcgtgtgca ttgcttctag gccagaaact gtgaagttct cttccacgtc   8940
ggattccggc acaaggaggt aatgccaggg cttctcaccg ctctttgcac cggcttgcgt   9000
cgcaatatgg caccacaggc ttgccgcatc tgctttacgc agaacctcgg tggcggtcat   9060
ttccgattgg cgttttacct cgatgatcag cttgcctgta tcggtttcga caacgaaatc   9120
gggctgatac ggcgcaccgt gattatcgaa aattttgaac tggttggggc caggtttcat   9180
ccaaaggcgg accgagctgt ctttttcaag gatgatcgcc agcttgcgtt ctggattaga   9240
gtcgaacttc gcatactgat agcagccctt cacgaagcca gtgaagatat acttccggat   9300
ctcctgcttt tgatctggcg gtgttttgaa atcccggatg aagctcgtac cggcggtatc   9360
gaaggtctgc ggacgcagct cgccgaatgc agaggtcaga gaaacacggt agttcgtgtg   9420
```

-continued ctcacgccac atattctgct ttatttgcga gaaaatgctt tcggccatcg ccttcgcatg 9480
cccccggacg acactgcgag tttgctcatc gtcgtccgcg aagcggttgc gggtttgggt 9540
gactgcctgc ccagccagat catacaagat ggcagcatgg gcgtcatagt cgatctcagg 9600
gtagtcgatc agccgcgcga cgatgtaatt ctccagccgg tttgcggtgt ccccccttatc 9660
ctcgctggaa atacgcgatg tcttctctgt acgcagagct tggatcatga gctcattgga 9720
caacggctgg aagttccagc tcttcatgtc caggtcgaag cgcttgaagc cgaaggaaac 9780
ttgttgctgc ggagtgatcg tgagagcagg gatcgcaagg gtccgctcca cgaaattctt 9840
gcacagctcc tgagcgaccg cgacggcctt ttccttcgtg atgctgggaa ggaaaccttc 9900
ttcgggtttc tgtgctgcaa tggctgcttc cgcgatgcgt tcgatcacct tggggtcgtt 9960
gagatcgcgg atcgaggaca cttccttgct gagctggggg atcacaacac tgagcaccgt 10020
gcgggcgacc ttcagctctt caggcgtgct gaagctgaaa ggcgcttggg tcggtgccgc 10080
agacgtcggc ttggcgacta gctgcacagg cgcgtccgaa gctttttcgt catccgcgac 10140
gacgactgtc ggctctgtct tggcctctgc ctgagcaagc atctggtcga ggatggaggg 10200
tgccgagacc gaaacaggct tcgagggcgg cacgtcacca ccctcaccaa tcgtcacctg 10260
cttcagcttg cgcgtgacgc cgttctcttc cttggctttc tcgatcagct cgttgaagcg 10320
ttcgtgggca atcacggtca gcgtgtcaac cacttcgacg ccggttcgct tgccataggg 10380
caggcgcaga ccgcgaccga gcgtctgttc ggttaggatg tccgaggccg aggcgcgcag 10440
cggaacgatg gtgaacaggt tcgagacgtc ccagccttcc ttcagcttgt tgacgtggat 10500
gacgatgtcc gtgtcgccgg ccttctcgat attcagcaaa cgctgtgcgt tctcgtcgct 10560
ttcctcgccg gtcagcttgg agtggatctc ggccacgcgc cccttgtagc gtccgccgaa 10620
gaactcgtcc gactggacga actcattcac ctgccgggca tgggtcgtgt cctgggtaac 10680
aaccagcatg aagggccgca ccaccttcac gtcattctgg cgggcatagg tttccagcgc 10740
caccttgacg tgctcgtggt agtggatgcc gtcttccagc ttgatccgtt ccagcgtgtc 10800
ttcgtcgacg gtcttcgggt tgaagttcgc gcgggtgccg acagccggtt ccttaacata 10860
gccgtcttcc atcgcgtccg gcagatcgta gcggtagacg acgttcttga agggctgcga 10920
gcgcgcgcca acggtcttcg gggtcgccgt cacctcaagg ccgaggatcg gtttcagctc 10980
ggcaatcgcc cgcgccccgg ccgaaccgcg atagcggtgc gcctcgtcca tcagcaggac 11040
caggtcatcc agttcggaga ggtaggagaa gtagctctcg ccgatatatt cctgaaggcg 11100
cttgatccgg ggggcgttgc cgccgcgtgc ttcggagttg atcttcgaga cgttgaagat 11160
gttgatgatc gcgccttctt ggccgaagag gtcggtgcca cgcacaccgc ggccttcctc 11220
gtagttctcg gcgttgacga tcagcggcgc gttatgggca aagacttcga tgccacggaa 11280
gacgtatttc gggctcgacg gctggaagtc ggacagcagc ttttcataga tcgtcaggtt 11340
cggggccaga acgaagaagt tccggctttt gccgatcatg tagaggtagc tgatgaaggc 11400
gcccatcagg cgcgtcttgc ccacgccggt cgccagcgca aagcagacgc tcgggaagtc 11460
gcgctcgaac tcctcgaagg tcgcgtcggc caggtcgcca tagacctcgc gcacggcggc 11520
gcgggccatg tcgatatcgg cttccttcgc ggggccgacg aggtcgacga tgtcatcgag 11580
ccgccgcagc gcctcggcct gcggcttgcg cagcgacagg cgttggttga tctgaaggac 11640
ggcgcgtttc gggtcggtcg tctgcatggc tcagttctcc tctgcgccaa acagatcggg 11700
tgtgtctgcg gctttggcct tggccgattt cttcggcgcg gggtgtctt cgatgtcgtc 11760

-continued

```
cggctcatcc tctgccatcg gcagggcgtt gatcttcaag gaatagtcat cctgccccca  11820
ttcgcagcgg tcaagcacca cgcgcgggat cttcttcagg gtcaggttgc tcaggctttc  11880
gccctgggcc tcataggcca tgcagcagat cagcaggctg cggtcctcgc ccacctcgtc  11940
cgagatggcg cggagctgtt cgatggtcag gctggccgtt gtcacataga tgaaggcgtt  12000
ctccgaagcc tgaccgtgca tccagtaggc ctcggttgag ggcgcgtaga catagttgaa  12060
atgcttgcac atggcctcgg ccagcatctc ggcattgtag tccttggaga tgacccagtt  12120
gccccagaca tccttctgaa gcagagatgg cgcaagacgg aagaaacggt agccgccgcc  12180
gcctctccag tttgtggcct cggtcacgcc gcccttatcg gtgccgttga tgactttttg  12240
cagccgaggc gcgacatggg ttttggcatg gtcccccagc tcgaccatga tccagcggcg  12300
gcccatcttg tgggccactg cacctgtcgt gccagaacca gcgaacgagt ctatgacaag  12360
gtcgcccggt tgagttccta tctgtataat acgctccagc agtttttctg gcttcggtgt  12420
agcgaacgta gcgtctccca aaccaagaag cgtgcgcagg tcattggttg cttcacgggt  12480
tgtaccagct tcttcaccga accaaatgct ctcaggtacg cggccttctt gatcgcagag  12540
atagatcttc cgaagaacac gcgtgtcctc gtttaagaat gtaatttccc cggtctctac  12600
tttgctggca aaggtctcct ttgaccacct ccaccctttc tctggcggcg gaatgatctt  12660
cccagaaggg gtagtaacat cgaacatgag attttctctg tagttcggac tacgtacatc  12720
tcctgctcgc caaggtcctt ttggatcttt gtctggatta ttatagtttt tgttgtgctc  12780
aggctttctg ggcagaaggt tgcgcgagaa cgcctctgtt ttccgatatg ctagaacgta  12840
attatgatgg agactgacgg tcttggcgtc atttttccct tgaacgctat gctgccagat  12900
gatcgagccg aagaagttcg atcggccgaa aatctcgtcg cacataacct tgaggtaatg  12960
cacttcgttg tcgtcaattg tcatccaaat ggagccgtct tcagaaagta ggttccgaag  13020
aatttctaac cgatctcgca tcattgtcag ccaaagcgag tgctccagcc cgtcatcata  13080
atgctcgaag gccgacccgg tgttataggg cgggtcgatg aagatgcact taaccttgcc  13140
ccgcacggca gggtcggttt ccagcgcctt gagtgccagc aggttgtcgc cgtggatcag  13200
catgttgtcg aagatgtcgc cctcgcgccg cgtgctggcg tgatgcgaga attccggttc  13260
ttcgatcaga atgcggggct caagccgcgg gcggttgttc ttgccgatcc aggtcagttc  13320
aagtttggtt ttggcggcca tcaggcaagg gtccatctta cagtgaatag ggtcgtcatt  13380
tcgggggtca ggttcagctg atctgcgatg tcatcaagca tccgctcgcg ctcagcgtcg  13440
atttcgcgca ggcgggtgta aagctggtgc tgaaggtcat ccacctgccg ctgcaaggcc  13500
ttggcctcgc gttgcagggt gaccttttct tccagcccga tcgtggcacg ggccagtttc  13560
ttcttctcgg tcgcttcctt gttcagcgcc ttgatctgct ggtcgaagga caccttggca  13620
tcctcgcgcc aggcatcgag ccgctcttcc tcctcgttga ggaaggagct gagccgatcc  13680
tgtgccatgc cgatgatcgc ggtctggcgc gcgttcaggg tttgggtcag gtcgctttcc  13740
ggcagggtgt ccgcgccaag gccctcggtc gtcgccggga catagagcat ccgagaggcc  13800
gtttccgggt cgatggctgt tccgccgtcg ctgaaggctg cgaagaccag ctcgtcatag  13860
accttggctg gggttttcag tcggacccgc gccacgcgca tccagcccga ctgccccctg  13920
agctgggcca cgtcgcccat gttgccctga taggcgctat agtcgaggcg cagcatggca  13980
gggaccagat cgcgcgactt ggccttctgg accagctgat cggccagccc ctcgtcgcca  14040
aggcggaaga aacgccagcc gcgctcgtca gcctcgggcc attcgctgga ccaggtttcg  14100
cccccgtaat cgaagcgctg cgcatggtcg tcgtggaagc gggcctccgg cagctcggcc  14160
```

-continued

```
cgcgcgacac caaggagggc gcgcttgaag tcaccgatgg cggaatgcac ggcgtctttc  14220
cggccaagaa gccgctcgat caccttgtcg tccatctcgg ccagcagctg atctcggacg  14280
ttcttcttcg cctcgtcgat ctcgacgctg aactcttcct gaaggcggtc gaaggcggcg  14340
tcgatctggt ccgtggtgcg gcaggactgg acgatgtcga ggatgcgccg ctcgatgtcg  14400
acgccggatt caatgacgcc cagaacctcg tcggaggagc cgaacacacc ctcgaaaagc  14460
ttgaacttct gttccagaag ctggtggatg cgcgcttcag cgtggttctt ccggttcagg  14520
aagttgatga cggtcacgtc gatcttctgg ccgtagcgat ggcaccggcc aatgcgctgt  14580
tcgacccgct gcgggttcca gggcaggtcg taattgatca gcagggagca gaactggagg  14640
ttgatgccct cggcgccgga ctcggtcgcg atcagaatgg tgcgatcgtt gcggaaggca  14700
tcgacgatgg cggccttcat atcggcggtc ttggagcccg agaccacatt ggtgtcgccg  14760
tgcttgtcga gccaagcctt gtagagcgct ttgctgtctg cgtccgagtt ggagccattg  14820
aggacgacgg tctgtccctc gaagccgctt tgttcgagca gatcgcgcag ataggtttgc  14880
gtccgcacgg attccgtgaa gatcacggcc ttgcgctggc cgcccttgga gacgatctcg  14940
tcgagcacgt tcggcaggca gtccaggagc gccttgcctt ttgcgttgtc cgagatggat  15000
gcggccagat cgcggtactg ggtgagccgc ttgatttccg cttcgagctg agcgggatcg  15060
acgcgctcag catcttcggt gtcgtcttcg atcgcgtcgg cttccgaacc ggaatccgcc  15120
tcgcgccagt cctcggcttc gtcgctgaaa ccatcaaggt catcgagcgt gtctgccccg  15180
acaacacgct tcgcctcaag cctgcggatc atcttgtcga gggtctgcat cacggcgaag  15240
gaggaagatc cgaggatctt gcgcagcatg agcgtcacaa gatgacgccc gttctgcccc  15300
aaggcgatgg tgctggggtc ttggagatac tcggaaacct tttcgtagag atcggtttcc  15360
agtcgaccag gcgtgaagtc gaaggtcttg gggagacggt tggtatagtt gatcaggcca  15420
gcgcgttgga cttggcggcg cagggttcgt ttgcagatag gctcaagacg tttcgcgagc  15480
agggcctgag aggtcaggcc ttctcgtccg ccaaactcgc ttcggaaggc ttgttctgaa  15540
ccgaagtagg tttcgtcgat gatgctgatg agtccgtaca gctccatcag gttgttctga  15600
agcggagtcg ccgtcagaag gagtttctga cgcccagcca gtgcctttcg cagaaccgaa  15660
gcccgagagt tttcggcggc cttgtagacg ttacgcagct tatgagcttc gtcgaatacc  15720
acgaggctcc aaggcgtgcg tcgcagagtg tctgcaattc gtgcggcgta ctcgtaggag  15780
acgatgataa tgccttctcc gcgccctacc gggtgcggag tgccttcgtt ctcaaggtct  15840
ttgacgcgct tggcatcaag aatgaacgat ggcagcgaga atttttcacg cagctcggtc  15900
gcccactgct tgcgcagaga agcagggacg atgaggagaa tgtttctctc acgttcccac  15960
cagcgctggc taatgaccag cgcagcttcg attgtcttcc ccaagcctac ttcatcggcc  16020
agaagaacgc ccttcgacaa tggtgagcgt agggcaaatg tcgcagcatc cacttggtga  16080
gggttgaggt ccaccttggc tgccgagagg gactgcgtca gagcgtcttc ttcctgaatg  16140
ccttcggatg tcaggtggtg cgcaaagaac tttgattgat attcagaaaa ctggaagagc  16200
aataggtcag gctccaaggc atattagtta agggaaggtt gttctaaatg ctgtcaagtt  16260
atggcctgcg gcttgatcgg ccagcacgaa ggactccctt ctgcccagga tattgggcct  16320
tctcgttatc acgccactga aatgtcacct gtactgcgat accatgcttg tcggctattc  16380
tggaaacttc cttccaagcc tcctgggctg attgcccttg gatagagatg ccgaggtcag  16440
ggtaatatcg gaatccttcc tcttcgtagc acgccgtctt ggtaggaatc tgtatggcct  16500
```

-continued

```
cagctaggtg atctccggat aggcccttag ccttaagaga actcactgcg ccgagaagaa  16560
ttgctgccca gtttggcttg tcgatcttct tgtgatcaac ctccgcagat aagacttttg  16620
taaatgaaag gcctggagtg gatttgaact ccatgaagct gctgatttcc gacgtgggat  16680
caatgctgat ctcgatgtca cgctctaggt caagcgctgc catcttctcc cgtaccagca  16740
gcatgatcgt ttctgatggg gtttctgtcc ccatccaagt cgagatgcac ttcagatcga  16800
caaaagttgg gtcgttcagt ctgactacgg gcataggcgt catccttcta tattcatata  16860
gaatatgtta catattcaat attatggtgt caatgctagc gtttgattgg caacctgtcc  16920
taaaacggtc gtttttgggc atagtgggat gaagtggtca aaatataggc cttgataatt  16980
ttgaacatgc ggctactttt ggacagggtt ttttgacacg gagggccata cattgacaga  17040
gcaaggccgt gtttttgcct atgtacgtgt ctcgacactc gggcagacag tcgctggaca  17100
gatgcaggaa attgcggcgg ctggctttca gcccccagcg tatcgtgtcg tttcggaaac  17160
catctctggc agtgtcccgg cgatgcggcg accagagttc gcgcgcctag ttgatcgctt  17220
ggaacctggc gacattctag tcgtgtcgaa gcttgaccgt ctcggacgcg acgcaatcga  17280
cgttacggag acagtcgctg cgctctcgca gatacctgtc cgagttcatt gcctcgcttt  17340
aggtggcacg gatttgacta gctcgtctgg acagttgacg atgaacgtcc tcagcgccgt  17400
tgcgcaattt gagcgcgatt tactccgtga gcggaccagt gcaggccttg cagctgcaaa  17460
agccaaggga aaacgactag gtcgtcctaa agtgctgacc gaggataacg agagcgaagc  17520
acgagcggct ctcgccagag gggaaactgt ttctgggatt gcaaagcgtt tcaacgtcag  17580
tcgggcgacg atcggccgcc taagagatag ttaggctatc ttgcctatgt cgtcgtgacg  17640
agtcctccaa atacacggat ggcttcacgc tcccatgcac gattaaacca agtaacatgg  17700
cggcttactt ggtccttaat ctcagggcat cccatgatgt ccgctgcctt gtaagcatac  17760
cgcaagaaat ttcggcgttt tccaagatgg gtataacgcg ccaggctttc tcgcttgaat  17820
acttcaaacg acggtacgtt tttcgccttt gcggcgatca tcttggcatg aatgccccgg  17880
cgcatttttc ctcggtaggc atcgagtgac gaaggtcgga tcttcgtttt ctgcccgtcg  17940
aaggtgaaac ccaaatactg gataggtgtg gcagaggcca acagtccgtc cttgaagtcg  18000
gcagtgtctg ttttgtcgat ggacatggaa aggcaaaaat ctgccagcat ttctctact  18060
actgcaacca catgatgcac cttcgcgcct agaggcagag tgaccgcgat gtcatcagag  18120
tatcttcggt aagatccccc tgccctagag caccaagcga tcatttcacg gtcaaaagtt  18180
cgaagataga tatttgcata caggccggac accggggtgc cctgcgggat accgaacgtc  18240
tggtcatgct tccgaatgag gccatccttt cggcctcgga catgatccga aaagtctgaa  18300
ggtgagcata tccttccgtg cccatttcgc tttcgaccaa gaagtttgtc tagatcttca  18360
gtctcaaccc atgagtagcg ggtcacgttt ttccaaacgc ttgcatggtg cccttccagt  18420
cttgtttcgc ctatcaaatc ggcgatctca tcgcggagca aggtgtgatc gagacagtca  18480
aagaatccgg aaatgtccat tgcgaagacc gtgcaatctc cacgagactt aatctcgtcg  18540
aacaacgcct ttgcatggtg aatattagtg ccgcccccac ggcgataggc tagcacggag  18600
tctgatgtgc cgtcgcgcca tagcgcccgc tcgtacattc tattgagatg tcccgcgtag  18660
gcttgcaggt aggctgcatc ctcatgactg gcgaagcgga tcggtcgctc tttcactttt  18720
acctcacggg cgccatcctt gttcctgaca taccttctgt tgacgtcagt aaacccaagt  18780
aaaggtagaa atctgtgagg cttatcttcg accgagaagt caaacgacag ctcccgatcg  18840
actaacggaa gatcgaaatg cttgtatttg cgttccttgg atatggccgg aagcacaaag  18900
```

-continued tcgtcggttg atggatcaaa ctcgttttca gacggcaggt aaaacccggg catagcgact 18960
ccgttcgtca aatgcccggg ctattgaacc tagctcccat caacaggcac cgaggtgccc 19020
tccggtacga gaaaacctgg cgtggtatgt tgtaaccacg atgtgcgaag gatgcgccat 19080
gaccgaaatc acgaccaccc ggtgccgctg ggcgcgggta gcgcttgcgg gccttaacac 19140
tggtcatccg ggtccacgcc ccggggcaaa atatcaatta ggtgctacct aattgaatgc 19200
aaggggacgc accaagaata aaaggacttt ttcagcttta gtggcgcctt atagtggtca 19260
tctggaacca ggacaaagag acaaccttct aggtaagatc ctcgtaagtt cgtatcagtt 19320
acggtgtcag atagtagcag ataacgcacg gcgttctgct ggcggagggc gagagaaatc 19380
tggttcgctg tgagcggtat ttcttgccca caacgcggcc cttattccag tctagtacag 19440
gcttggcagc caattgccgc gactggcata gcatcgtgct ccttgattac atgctaaaga 19500
ggtactttga ggtcttagcg gtcattcgac gattttgctc agataacagc gtaagtaaac 19560
gctgccccaa gtttcaggat ctagcgccca acgatcttat cacaagagac catgttaatg 19620
cgtctattac attaggatgg ttcaaagttg ggttcgggat catctggtat tggggttcca 19680
aagaccaatt cgtgc 19695

<210> SEQ ID NO 4
<211> LENGTH: 4211
<212> TYPE: DNA
<213> ORGANISM: Ketogulonigenium
<220> FEATURE:
<221> NAME/KEY: misc_feature
<223> OTHER INFORMATION: pADMX6L4

<400> SEQUENCE: 4
gcgtggccct tcccgccgag ctggacgccg aagcccaagc ccggcttgtc cgcacctggg 60
cacgggacca cctggccgcc gccggcatcg tcgcggacat cgccattcac gagccgagcc 120
gcgaaggcga cgaccgcaac acccatgccc acatcatgac caccctgcgg cgtttcgacg 180
gggcaaccgt ggacggatgg gcgaagggtg ccgcccgcga cctgaacgac aaggcgttcc 240
tcgagaacct gcgggcatcg tgggagaccg cccagaacgc cgcactggag gccgccgggt 300
caaccgcacg ggttgaccac cgcacccttg ccgcacagca tgaggacgcc ttggccgcag 360
gtgatgactt actggccgcc gtcctcaacc gccccccgga acctcacctg ggcgtgtcgg 420
cccaagcgat tgaccgccgg gccgggcgtc cggtcagcaa ccggggccgg gccttggcgg 480
aggtcaggga gacccgcacc cggctcatga cggcatacga cacggcacgg agggccgccg 540
tgttcatcgc aacgaccacc gccgggcttg ttgaccgggt gtccggtgcc cggtcagaga 600
ccggacaccc cattgcccga atgttcggcc ttggccgtca tgcggcaact gttgccgaca 660
ccgtgccaga accgtcccgc ccatcgccgg acgacgatac cccgtccccg tcctgacccg 720
cctcaaaccg tgccgatgca gcggcctctt taagcccact ctgtgcctct tcggcggccc 780
tgtgctgtct ggccatccag aaatccagaa tggccgcacc acgcatggct tcggcctcgg 840
cgtcccgtgc ctcgtccaga cctgcccgga ccaccaccgc ctcagcggtt ccgtgcatgt 900
ccagatgtgc ggccaccatg tccaacacgg cggccctgac ttcctcgggc gacacctcgg 960
cccccatcca atcgtggccg aacttctcgg ccacgatgcg tgacaccgcc gccttgcaga 1020
aggtccgggc atactgctcc agaccgtatg cagccttgtc ctcgaccgtc cgagcgtcag 1080
gcgccttgat gaccctctga actgccattg atgccccttt ctcgacttcg attagtgccg 1140
caatttgctc gaccatgcta cgaacccaat ggacggtccc cagcagacgc cacgccccat 1200

-continued

```
tccgtgccag acctgcggcc ccggccttct tgtccgattt gggcgaaaac cggaactcaa   1260
cccgcacaag atgcgggtcc gcgtcctcga tggccaactt gccgtccgcc acccgttcaa   1320
ggtctttctg ataaaccttc acggacgcct cacccttgcc ccaatagaag gtccggcccg   1380
tgtcgctctc gatgacacgc ggggccgcca tcttggacgc cttggacatg cggcgggcat   1440
agtccagcaa ggcgtccatc aaaccctctt ggctatggtc catcgacacg tcagcacgag   1500
ccagcaggga gggaccaaag gcgttcaggg cctgcggggc cagcagcgca caacgaccat   1560
caccaccggg tatttcaagg ctcggcatgt ttctggcatg ccctgcccgc accgtagccc   1620
ggcgttcctc atcaatgggt gagtccgcgt aatgcaaggc acccgcgaaa ccgtccgtcc   1680
cgttgcccac gcgttgagtg tgcagaccag ccagcacaga ccagagacaa aaggcatccc   1740
gtgcctctct tgcctcttcc tcgcccatcc tgtcctcgta gtgaatgaca cgcatggcct   1800
caacgcgttc agtgcccgtt aagcgggcag cctcggcaac ctccgacggg tcagccctgc   1860
ggcgttcgcc cttgccgttc cgcccgttag gcaacgtgat tgtgagccag tcgaaaaacc   1920
acgccgtttg cagccatttt tccatgaccg ggctggtttt cttgcccttc cttcgcttct   1980
ccgaaggtgg ggggcacttt ggggcacaaa ccgccggttt tacgccgttc ggggcctgct   2040
tttcacattg aaaatcaggt gtttgccccg aactaccccc cctgttagca tgtggggggt   2100
tttgggcctt gcggcggacc tcatcgagag ccgcgaccgc ctgctgtgaa agggttttac   2160
cgccgtggac catcatcgcg tctcccgttg agggtggacg cggtctcaag catgttgatt   2220
cttgcgaatg acatggctat atctctccaa agttctgagg acgacgcggg gaccgcgaaa   2280
tcacagcgtt cgtccaggtt aagggctccg gttaatcccg gagcctttcc atttcatatg   2340
aacgacatcc ggaaaaatca acatattgat gccgctggac gatgtgcggc caagatgtgc   2400
tgcagtattc ccggcgggcg gaaccgttcc gatatttgaa gtctccacgc ttccgcccgc   2460
ctaatgtcgt tctgtcgttg aactttcata aaggtgaaac cctgctggtt tcccccggcg   2520
gcgaagccgc ctccccccttc ctgcctcaca aaaaaaggga aaaggcccgt ttcaaccgat   2580
cgacgcaatc tcctttcacg gtatccagat accttttctg gtgaagccat ccgaaacaaa   2640
ggccgcgagt cgtcacacct gggcttgacc gacgcgaatc actcggacag tgtccggtca   2700
tggaccacat gctgacccca aaacaggcgg cggcccgtgc gggctgcggg cgttcctcta   2760
tcatgagggc gttaaagtcc caatctttgc ccgctatacg cgataatgag aaccgctggc   2820
agattgaccc ggacgccctt gaccgttggg ccggtcacag gccggacaat gaccggtcta   2880
tgaccgaaca cggaccggcc acaccttcgg acacccaaac ggacaccccg gagaccttgg   2940
cacggctcgc cgttgccgag gcccggttga gtgatgccct gtcccgcgtc gaagatttgc   3000
agagagaacg ggatgaatgg cgggcacagg cacaagcctt gacccgtcag cccggttggc   3060
tggaccgcct actgggtcga acctgacccc ccatcgtcac ctttggcctc accagcggat   3120
tgcttgtgaa ccaaggccag cagttccttg acctgttcca cgctacccgc ttcggcttca   3180
atatcgccca tcttgacgcg gacctttcgg ccttgtctcg cagccaccca tccaccgata   3240
gcaccaatca cagccggacc gagggttgtg gccatcatcg tgaactcacc caaaaaagtg   3300
atgccaccag agccagccga gtccctgatg aacgctcgct ccgaatattt tatgtcctgt   3360
tctttcagga tggtgcggaa ctccccggca tcttctttcg ggaaaaccgc gatttctaaa   3420
tcactcatgg aatgctcctt ttgcccatga ggtaataatg ccctgccaat gagcaccgag   3480
caaatcagcc gggttgctct ttcgaaacgg tctcgggctt tggaagtgtc cacccctcga   3540
```

-continued acagtgcccg gtctctctct ggcatcgagg caatcgccat ccgcagcacc ttgacccatt 3600
gaggatcttt tgcagcttgc ccgataaccg caccgcccag gacgattttc cgccgtgcgt 3660 cctttttttcg gtcctctgcc cgaagttttg ccccggcttg tcgtatctgg gcctctgccc 3720
tcgccttggc ctctttggcc cgctctaact gcctttctac tgaagttctt gccattttcc 3780
gtcctccttc atagggccta tatgaacgga gagggaacga agcaagaagt tctcaagaac 3840
ccgaagggcg cacttacaca aactctgggg agtttgtttc gggcgcccta ccgggggtca 3900
tctcgccgat ggggcgtctc cgacggtaaa aagaggaggg gccgccgtgg cgatatatca 3960
cctgtccgcg tccattatcg ggcgaagcga tggccggtca gccgttgccg cgtcagcata 4020
tcgggccggg gccgacatga ccgacccgga caccgggacg cggcacgact acacccgaaa 4080
gcgaggcgtc cgggcaacct tcatggagtt gcccgaaggt gccccccgatt gggccaccga 4140 ccgcccgagc ctctggaacg ccgtccacgc gaaggagacg cggaagaact cgcggctttc 4200
gcgtgagatc c 4211

<210> SEQ ID NO 5
<211> LENGTH: 1458
<212> TYPE: DNA
<213> ORGANISM: Ketogulonigenium
<220> FEATURE:
<221> NAME/KEY: misc_feature
<223> OTHER INFORMATION: replicon pADMX6L1

<400> SEQUENCE: 5
abgggccttg catccgatgg caagcaaaaa ctacccagtc cgtccgtagg cggggggtcg 60
ccagccctgt gggtgggcgc ttccccccgg cccgcaagcg ggcccggaat gggcattttt 120
tgcctgccct aagatcataa gaagggcaaa aaaaacatcg tttcaaaaca gcgtgttacc 180
acccccctat aggacaccag agtccggggt agaggactct ggtgtcctct taggccattt 240
atgtccaaga atgtgacagc cagccgagcg gaggtagagg actctggtgt cctatgctta 300
ggccatttat gtccaaaaac ttgacaaggg ccacattcct gccaaatctg tccagaattt 360
ggaaaaattc gccggatagt agacagtggc aaagcctccc cccattcccg caaagcgccc 420
gctcggcact tgggttcaaa ctgaccggga agcccacgag gcgtgggcga tactggcaaa 480
aaagcctgct gccagcgctg tgatgcacat tctgtgcgcc aacctcggtg agcataatgc 540
cgtggtcatc agccaggaca ccatcgccaa gctgtgcggc ctttccacac ggtccgtcag 600
gcgcgccatc gtcgatctgg ccgaaggccg atggatcgag gttcgccaac ttggcgcgac 660
cagccagacc aatgcctatg tcgtcaacga ccgggtggca tggcagggat cacgggacgg 720
actgcgctac agcctgttta gtgcggctat agtcgtgtcc gaggaggagc aacccgaccg 780
cgctgaactc gaccagcaag ccccccctgcg acacctgcca cgcatcagcg aggggcagat 840
acccaccggc cccggcctgc cgccaccttc gcaaccgttt ctaaaagaca tggagccaga 900
cttgcccacc attgaccggg caacatcacc caactttgac cagcaggaac aggggtgaaa 960
aaggtggaca aactttccat acgcgaggcg gtaaaacact tcgatgtttc ccggccaacc 1020
ctgcaaaaag cccttaaatc tggcaagatt tcaggtgttc aggatggaca aggaacgtgg 1080
acaatagacc cctcagagat ggcaagagtt taccagccaa ggcaagatga ggtggtaaag 1140
gatggtggcc aagaacatga aaatttgtcc gccaagaaca cccctttaca tggtcaagtt 1200
gaggttctga aagagcggct tgcagatgct gaaaaacggg tggcgatagc cgaggcactg 1260
gccgaagaac gtggaaaaca catcgaggat ctacgccgga tgctgcctgc accggaagcc 1320

-continued

```
ggtcagcccc gccgccgctg gtggccatgg taaggtcagc tatgcgggac caagccgcag   1380

ctcgcaagtg cggcaacaga atcagacccg cttcggacag agagctcaag ctggtggaaa   1440

accgcctgtg aagctgct                                                 1458

<210> SEQ ID NO 6
<211> LENGTH: 2401
<212> TYPE: DNA
<213> ORGANISM: Ketogulonigenium

<400> SEQUENCE: 6

caccatggcg cgctgcagct cttctttgct tctgttggtt cttctctcgt caagaagctc     60

aggcggaaac cgcactataa agtgcagaac aggcttcttc gccgctttgt tttgcctaac    120

gccttttgtg tgcgcgtcat atgccgaccg aaggtctagc gtcttataaa cgagcggaga    180

ggcatctctt acgacgcgtt tcgcacttgt tttgtcttgt cgtttcgcgt gcttttcggc    240

tgctgacaat ccagccatat ctaacgcact acatctcacc gctgctttca ttttcaatcc    300

ctcatatatt accttttctg ttgtttttgc gaaaaacgca aaactcgctt tgcgtttttt    360

gttcggcacc tgcggcacct ccaaaaaaca cgcttgctct ccgagggtct ggcaggagcc    420

taagaggggg cattctgccc ctgatcgacc ccattgaggc tcgatctaaa cagacccccc    480

acaggggcgt ctgtgggccg ctagtgcggc cttccgccat cttcgagcca tctgatctct    540

gcaattagag atgcatggcg catctcccat tccagctcag atatcccgta tctgtcgatg    600

acggtgtcat acaattcgtc gagccttgct tcgcgctctt cttttgtcat gccagttgca    660

tcgcgttctt ccatctcctc gttctcctct atgatgaaat cattttcgtc ctcgtcgttt    720

ggcccgcttt ctgctgcctt gaccgcaaca gcgcctccgc gctctgcggc ctcgagcaag    780

ttcacgcgtt tagcgcgcac ttgcttccac ccttcattgt cccactccgc gacaatttca    840

gggccgcttt gctctgctgc atcaacttca gccatagctt catcgtcatc cagctcgacc    900

aaaccgcatt cttctttcaa gccttggctc cacaccaatt gccgcctacg cttgccgctc    960

gttgcattga aatattcgag ccaaagcccg tcatcgcccg cctgaagtag ctgccttggc   1020

gtgcgtcctt tgcgttttcc gctcttcgag cttgaaagcg tcaactcttc ggcagcgccc   1080

cacttcgcta cgtagtcgcc cgcattggca gccccgcgaa cgtcaaacgc cgcatcgttg   1140

ccccacatgc catacccctt cagacatgca cgccacgcat cgcctagacg ttgcatcaga   1200

tgcagcgctt cgctttcatc gccagctctt agcaagacaa tttcgtgaaa gtgcgggtgc   1260

cacccatttg catagctatg agtaatttca gttgatgtga ctgacccaac aaatggtaaa   1320

tcgcgccact cgcggcgctg acgcaaccgc tgtttcgcct tcttcatgtt ttggagaaga   1380

tcaaaaagcg aatcacctgc tttgtgctgg gctgtcagag ttatgagcac cggcacaaac   1440

ccgttgtcgc gcgcccacgc gagcaagtga ttcatttcag aacggcgaat ttgcgcgatg   1500

cgagcgctac aaactgcgca gccccacaca ttccggcact gtgctagacc tgaaaagaat   1560

gcccgacgcc cgccatcctc gcccacgttt tgcacgttta gctcaactgt cggagacact   1620

tttacgtgcc gacatttcgc aacttggtgg ggcttgtttt tgttcagatt caacagaatc   1680

cgagcggctg aacgcagatc tgcataaagc tgccgcctac tgaataacct gttgttttct   1740

ttgttttttt cattcggttg acccccattc tggtcaaccg atttacggta tataccaagg   1800

ggggtctgcc gacccccctga aaaagcgtca tcgccgcgcg cctgcgcacc cgcgttcttc   1860

ttcgatttct gaactgaatg tgatgctagt ttgtgagaca tggccgcaaa ccccgacggg   1920

tgcggcgact attctcttga ttttctgcgt ctgtgcgcat actatcctcc gtgttcatca   1980
```

-continued

```
ggctcacgcc tgatctgatt agggctcttg tctctgcttg tatcgtcgcc aaactatact   2040
ttaagcagcg tctagagcct gatgaacgat ctaagaagcc cgccccctga aaggcgggct   2100
tttttgatct gtgccagatg ttgttacatc ggcgctcaaa aatcaagttt tttcttgact   2160
ttcaataatt tgcattatgc acattattat cgtttgataa taagagccag aacagcacag   2220
aatagttgtg cgatagctat gaataatagc agatccatcc ctgtttcctt tcttactaaa   2280
tacaatgcga aactgctcgc atctgtttta tttagttgaa tcggaaactc caaatcggcc   2340
ggattcaaaa aaaatataga ctatctttaa agtagcaacg ccgccgctcg cgcgacggca   2400
t                                                                   2401
```

```
<210> SEQ ID NO 7
<211> LENGTH: 2029
<212> TYPE: DNA
<213> ORGANISM: Ketogulonigenium
<220> FEATURE:
<221> NAME/KEY: misc_feature
<223> OTHER INFORMATION: replicon pADMX6L3

<400> SEQUENCE: 7
```

```
agagaataag atcaggtctg ttctcgtgcc gccagcggtt aagcaggtta tagagccgaa     60
attcactctt attcatcaat tgcttgctgc tgtagagcga ttttcgccct tcaacgaacc    120
agtagacacc cccgacaagg gcgatgacca ccagaaatcc aattatcatt gtgaaattaa    180
tgtcggtcat gactgcactc cctcaaggcc gaagtcagag attgcatctt gacgcagagc    240
gacgagttca acgccgtcga tgcggttttg ggtggcggta gccgggctgg cgcggatacg    300
cctaccgttg gcacggtttc taggcgacat actgaggcaa accggatttc cagtgggctg    360
cgtgctttgt tgtaagcgcg ccatttcatc cccccgaggg caggggaacg gctcacaact    420
tccaaaggcc ccgaaaaatt ctcgcgatga ccccaccacg ggatttgtgc aacacaatcg    480
gcgcgcggga caggctcata tcaacttgga taagcgccgc gttttttgca aaatgcgaga    540
aagtgcttat ccgcatcttt cacgttgatg gccttgtcat gcacccaaga acgccactct    600
tcttcaaggg agtaaacatc ccacccagga gcaagttcac gggcagtatc gcgtgtgtcg    660
ggatcgttga acggcaaggc ctgaaaagtg gttgatgcta tagtttccac caccttgggt    720
cggaagacag cgttctctcc ttcgatactc atgctgtagt cagggaagtg gtcgtgcgcg    780
gtgtcatcct caatgatctt cgaaagcagg cgacggaact cttttttagt tgagccggaa    840
ccgcacttgt ttcgcaagag ctccaagcta cacatccatt ttgactgcgc gccacaatgc    900
tttcgcccta tctcatacaa ccgcctttcg aggggctttc tgagcaggaa atacccccgg    960
cttagagtga ggacatggtt gttctcgatc gcatcaaaga cccagtcaga gagcgttatt   1020
tcgacatcaa gcattcggcc gtcgcgggtt acgcgcacga tctcggctga ttcaatcagg   1080
ccaaatacct tgaagtattc tttcccacct tgacgaatat tcgtttcaat ttgggttccc   1140
tgcagccgcc gaagggcatc tttgagcagc tgataaccct gaccggatgt ctgacggttc   1200
gttgccacaa gcagatcata agccttgaaa cgcatcgatc tacttatttt ctgcccctca   1260
ttaatggccg ccatgcactg gctgatgcag tagatcagca catcacggtc atgaacggta   1320
gcaaggccat agcgtgaagg ggaaacctcg atccaattgt cgttgttctg atagcggcgt   1380
ggcttcatgt ccggctttgt agacagggtg aacatagggt gctccatcga agccatatcc   1440
cccttgggaa ccgcatcaac gatgtcgcaa acgaaaaggt ctttttgtgg atgacgatcc   1500
ggcaaaagcg gtgatcgtag gttcgtcatt tcacacactc ccgcgccaag taaaaattcg   1560
```

-continued

```
tcatttcaca caccgtacaa gactatcgtc atttcacaca ccactcgtca aggctcgtca   1620

tttcacacac ccaaggaggc tgtggataac tcgagccgct atcgtcattt cacacaccat   1680

ctttcgtcat ttcacacacc atctttcgtc atttcacaca ccaggtgtta ttttttttat   1740

agttatatca attgattacg agctgttttc ggagctgtaa ctctattcta actctattct   1800

aactctcata gcttgccaaa atggcacctc atatcccgga tatccggttt cattatgaaa   1860

ccaatcaaca acatttacgg tgtttttga ggagcaacac tgtcccaacg caggttcaaa   1920

ccgatcacgc cgaatctgca aagaaagggg cagtgctatg ttcatttggt cactcgagga   1980

tcacccgaac cacaggtaag ccctcacatg ctatgttgat acctccagg              2029
```

```
<210> SEQ ID NO 8
<211> LENGTH: 151
<212> TYPE: PRT
<213> ORGANISM: Ketogulonigenium

<400> SEQUENCE: 8

Met His Ile Leu Cys Ala Asn Leu Gly Glu His Asn Ala Val Val Ile
1               5                   10                  15

Ser Gln Asp Thr Ile Ala Lys Leu Cys Gly Leu Ser Thr Arg Ser Val
            20                  25                  30

Arg Arg Ala Ile Val Asp Leu Ala Glu Gly Arg Trp Ile Glu Val Arg
        35                  40                  45

Gln Leu Gly Ala Thr Ser Gln Thr Asn Ala Tyr Val Val Asn Asp Arg
    50                  55                  60

Val Ala Trp Gln Gly Ser Arg Asp Gly Leu Arg Tyr Ser Leu Phe Ser
65                  70                  75                  80

Ala Ala Ile Val Val Ser Glu Glu Glu Gln Pro Asp Arg Ala Glu Leu
                85                  90                  95

Asp Gln Gln Ala Pro Leu Arg His Leu Pro Arg Ile Ser Glu Gly Gln
            100                 105                 110

Ile Pro Thr Gly Pro Gly Leu Pro Pro Pro Ser Gln Pro Phe Leu Lys
        115                 120                 125

Asp Met Glu Pro Asp Leu Pro Thr Ile Asp Arg Ala Thr Ser Pro Asn
    130                 135                 140

Phe Asp Gln Gln Glu Gln Gly
145                 150


<210> SEQ ID NO 9
<211> LENGTH: 466
<212> TYPE: PRT
<213> ORGANISM: Ketogulonigenium

<400> SEQUENCE: 9

Met Ser His Lys Leu Ala Ser His Ser Val Gln Lys Ser Lys Lys Asn
1               5                   10                  15

Ala Gly Ala Gln Ala Arg Gly Asp Asp Ala Phe Ser Gly Gly Arg Gln
            20                  25                  30

Thr Pro Leu Gly Ile Tyr Arg Lys Ser Val Asp Gln Asn Gly Gly Gln
        35                  40                  45

Pro Asn Glu Lys Asn Lys Glu Asn Asn Arg Leu Phe Ser Arg Arg Gln
    50                  55                  60

Leu Tyr Ala Asp Leu Arg Ser Ala Ala Arg Ile Leu Leu Asn Leu Asn
65                  70                  75                  80

Lys Asn Lys Pro His Gln Val Ala Lys Cys Arg His Val Lys Val Ser
```

-continued

```
                85                  90                  95

Pro Thr Val Glu Leu Asn Val Gln Asn Val Gly Glu Asp Gly Gly Arg
            100                 105                 110

Arg Ala Phe Phe Ser Gly Leu Ala Gln Cys Arg Asn Val Trp Gly Cys
        115                 120                 125

Ala Val Cys Ser Ala Arg Ile Ala Gln Ile Arg Arg Ser Glu Met Asn
    130                 135                 140

His Leu Leu Ala Trp Ala Arg Asp Asn Gly Phe Val Pro Val Leu Ile
145                 150                 155                 160

Thr Leu Thr Ala Gln His Lys Ala Gly Asp Ser Leu Phe Asp Leu Leu
                165                 170                 175

Gln Asn Met Lys Lys Ala Lys Gln Arg Leu Arg Gln Arg Arg Glu Trp
            180                 185                 190

Arg Asp Leu Pro Phe Val Gly Ser Val Thr Ser Thr Glu Ile Thr His
        195                 200                 205

Ser Tyr Ala Asn Gly Trp His Pro His Phe His Glu Ile Val Leu Leu
    210                 215                 220

Arg Ala Gly Asp Glu Ser Glu Ala Leu His Leu Met Gln Arg Leu Gly
225                 230                 235                 240

Asp Ala Trp Arg Ala Cys Leu Lys Gly Tyr Gly Met Trp Gly Asn Asp
                245                 250                 255

Ala Ala Phe Asp Val Arg Gly Ala Ala Asn Ala Gly Asp Tyr Val Ala
            260                 265                 270

Lys Trp Gly Ala Ala Glu Glu Leu Thr Leu Ser Ser Ser Lys Ser Gly
        275                 280                 285

Lys Arg Lys Gly Arg Thr Pro Arg Gln Leu Leu Gln Ala Gly Asp Asp
    290                 295                 300

Gly Leu Trp Leu Glu Tyr Phe Asn Ala Thr Ser Gly Lys Arg Arg Arg
305                 310                 315                 320

Gln Leu Val Trp Ser Gln Gly Leu Lys Glu Glu Cys Gly Leu Val Glu
                325                 330                 335

Leu Asp Asp Asp Glu Ala Met Ala Glu Val Asp Ala Ala Glu Gln Ser
            340                 345                 350

Gly Pro Glu Ile Val Ala Glu Trp Asp Asn Glu Gly Trp Lys Gln Val
        355                 360                 365

Arg Ala Lys Arg Val Asn Leu Leu Glu Ala Ala Glu Arg Gly Gly Ala
    370                 375                 380

Val Ala Val Lys Ala Ala Glu Ser Gly Pro Asn Asp Glu Asp Glu Asn
385                 390                 395                 400

Asp Phe Ile Ile Glu Glu Asn Glu Glu Met Glu Glu Arg Asp Ala Thr
                405                 410                 415

Gly Met Thr Lys Glu Glu Arg Glu Ala Arg Leu Asp Glu Leu Tyr Asp
            420                 425                 430

Thr Val Ile Asp Arg Tyr Gly Ile Ser Glu Leu Glu Trp Glu Met Arg
        435                 440                 445

His Ala Ser Leu Ile Ala Glu Ile Arg Trp Leu Glu Asp Gly Gly Arg
    450                 455                 460

Pro His
465
```

<210> SEQ ID NO 10
<211> LENGTH: 342
<212> TYPE: PRT
<213> ORGANISM: Ketogulonigenium -continued

<400> SEQUENCE: 10

```
Met Thr Asn Leu Arg Ser Pro Leu Leu Pro Asp Arg His Pro Gln Lys
1               5                   10                  15

Asp Leu Phe Val Cys Asp Ile Val Asp Ala Val Pro Lys Gly Asp Met
            20                  25                  30

Ala Ser Met Glu His Pro Met Phe Thr Leu Ser Thr Lys Pro Asp Met
        35                  40                  45

Lys Pro Arg Arg Tyr Gln Asn Asn Asp Asn Trp Ile Glu Val Ser Pro
    50                  55                  60

Ser Arg Tyr Gly Leu Ala Thr Val His Asp Arg Asp Val Leu Ile Tyr
65                  70                  75                  80

Cys Ile Ser Gln Cys Met Ala Ala Ile Asn Glu Gly Gln Lys Ile Ser
                85                  90                  95

Arg Ser Met Arg Phe Lys Ala Tyr Asp Leu Leu Val Ala Thr Asn Arg
            100                 105                 110

Gln Thr Ser Gly Gln Gly Tyr Gln Leu Leu Lys Asp Ala Leu Arg Arg
        115                 120                 125

Leu Gln Gly Thr Gln Ile Glu Thr Asn Ile Arg Gln Gly Gly Lys Glu
    130                 135                 140

Tyr Phe Lys Val Phe Gly Leu Ile Glu Ser Ala Glu Ile Val Arg Val
145                 150                 155                 160

Thr Arg Asp Gly Arg Met Leu Asp Val Glu Ile Thr Leu Ser Asp Trp
                165                 170                 175

Val Phe Asp Ala Ile Glu Asn Asn His Val Leu Thr Leu Ser Arg Gly
            180                 185                 190

Tyr Phe Leu Leu Arg Lys Pro Leu Glu Arg Arg Leu Tyr Glu Ile Gly
        195                 200                 205

Arg Lys His Cys Gly Ala Gln Ser Lys Trp Met Cys Ser Leu Glu Leu
    210                 215                 220

Leu Arg Asn Lys Cys Gly Ser Gly Ser Thr Lys Lys Glu Phe Arg Arg
225                 230                 235                 240

Leu Leu Ser Lys Ile Ile Glu Asp Asp Thr Ala His Asp His Phe Pro
                245                 250                 255

Asp Tyr Ser Met Ser Ile Glu Gly Glu Asn Ala Val Phe Arg Pro Lys
            260                 265                 270

Val Val Glu Thr Ile Ala Ser Thr Thr Phe Gln Ala Leu Pro Phe Asn
        275                 280                 285

Asp Pro Asp Thr Arg Asp Thr Ala Arg Glu Leu Ala Pro Gly Trp Asp
    290                 295                 300

Val Tyr Ser Leu Glu Glu Glu Trp Arg Ser Trp Val His Asp Lys Ala
305                 310                 315                 320

Ile Asn Val Lys Asp Ala Asp Lys His Phe Leu Ala Phe Cys Lys Lys
                325                 330                 335

Arg Gly Ala Tyr Pro Ser
            340
```